(12) United States Patent
McMahan et al.

(10) Patent No.: US 10,982,219 B2
(45) Date of Patent: Apr. 20, 2021

(54) GUAYULE WITH INCREASED RUBBER PRODUCTION AND YIELD

(71) Applicant: The United States of America, as represented by the Secretary of Agriculture, Washington, DC (US)

(72) Inventors: Colleen M. McMahan, Sausalito, CA (US); Maureen C. Whalen, Silver Spring, MD (US); Dante Placido, Oakland, CA (US); Niu Dong, San Pablo, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 224 days.

(21) Appl. No.: 15/975,851

(22) Filed: May 10, 2018

(65) Prior Publication Data
US 2018/0327765 A1   Nov. 15, 2018

Related U.S. Application Data

(60) Provisional application No. 62/504,762, filed on May 11, 2017.

(51) Int. Cl.
| | | |
|---|---|---|
| C12N 15/82 | (2006.01) | |
| C12N 15/113 | (2010.01) | |
| C12N 9/88 | (2006.01) | |
| C07K 14/415 | (2006.01) | |
| C08L 7/02 | (2006.01) | |

(52) U.S. Cl.
CPC ........ *C12N 15/8243* (2013.01); *C07K 14/415* (2013.01); *C12N 9/88* (2013.01); *C12N 15/1137* (2013.01); *C12N 15/8218* (2013.01); *C12N 15/8251* (2013.01); *C12N 15/8261* (2013.01); *C12Y 402/01092* (2013.01); *C08L 7/02* (2013.01); *C12N 2310/11* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 5,633,433 A | 5/1997 | Backhaus et al. | |
| 6,132,711 A | 10/2000 | Backhaus et al. | |
| 6,541,682 B1 | 4/2003 | Nehra et al. | |
| 7,129,392 B2 | 10/2006 | Hahn et al. | |
| 9,018,449 B2 | 4/2015 | Dong et al. | |
| 9,523,097 B2 | 12/2016 | Kang et al. | |
| 9,574,203 B1 | 2/2017 | Dong et al. | |
| 2003/0150008 A1 | 8/2003 | Karunanandaa et al. | |
| 2003/0217388 A1* | 11/2003 | Feyereisen | C12N 9/88 800/286 |
| 2006/0217512 A1 | 9/2006 | Mau et al. | |
| 2006/0218660 A1 | 9/2006 | Dong et al. | |
| 2014/0325699 A1 | 10/2014 | Kang et al. | |
| 2018/0127767 A1* | 5/2018 | Scheller | C08L 7/02 |

FOREIGN PATENT DOCUMENTS

EP       0675202 A1     10/1995

OTHER PUBLICATIONS

Stonebloom, et al. (BMC plant biology 19.1 (2019): 71). (Year: 2019).*
Van Beilen, Jan B. et al., "Guayule and Russian Dandelion as Alternative Sources of Natural Rubber," Critical Reviews in Biotechnology, (2008), 27(4):217-231.
Wang, Cunxi et al., "Overexpression of a cytoplasm-localized allene oxide synthase promotes the wound-induced accumulation of jasmonic acid in transgenic tobacco," Plant Molecular Biology, (1999), 40:783-793.
Archer, Bernard L. et al., "New aspects of rubber biosynthesis," Botanical Journal of the Linnean Society, (1987), 94:181-196 with 6 figures.
Backhaus, Ralph A. et al., "Purification and Characterization of an Abundant Rubber Particle Protein From Guayule," Phytochemistry, (1991), 30(8):2493-2497.
Cornish, Katrina et al., "Effect of Different Allylic Diphosphates on the Initiation of New Rubber Molecules and on Cis-1,4-polyisoprene Biosynthesis in Guayule (Parthenium argentatum Gray)," J. Plant Physiol., (1995), 141:301-305.
Da Costa, Bernard M.T. et al., "Magnesium ion regulation of in vitro rubber biosynthesis by Parthenium argentatum Gray," Phytochemistry, (2006), 67:1621-1628.
De Luna, Phil et al., "A Molecular Dynamics Examination on Mutation-Induced Catalase Activity in Coral Allene Oxide Synthase," The Journal of Physical Chemistry, (2013), 117:14635-14641.
Gao, Benlian et al., "Role of the conserved distal heme asparagine of coral allene oxide synthase (Asn137) and human catalase (Asn148): mutations affect the rate but not the essential chemistry of the enzymatic transformations," NIH Public Access, Author Manuscript, Arch Biochem Biophys, (2008), 477(2):285-290.
Harms, Karsten et al., "Expression of a Flax Allene Oxide Synthase cDNA Leads to Increased Endogenous Jasmonic Acid (JA) Levels in Transgenic Potato Plants but Not to a Corresponding Activation of JA-Responding Genes," The Plant Cell, (1995), 7:1645-1654.

(Continued)

*Primary Examiner* — Charles Logsdon
(74) *Attorney, Agent, or Firm* — John Fado; Ariel Atkinson

(57) ABSTRACT

Altered guayule that produce more rubber than the amount of rubber produced by non-altered guayule are provided. The alterations may include (i) a reduction in amount of functional PaAos produced by the altered guayule, (ii) an increase in amount of a transcription factor produced by the altered guayule, (iii) an increase in amount of salicylic acid within the altered guayule, (iv) exposure of the altered guayule to cold temperature, and (v) a combination thereof. Methods of producing the altered guayule and methods of increasing the amount of rubber produced by a guayule are also provided.

10 Claims, 17 Drawing Sheets

Specification includes a Sequence Listing.

(56) References Cited

OTHER PUBLICATIONS

Macrae, Sharmane et al., "Rubber Production in Guayule: Determination of Rubber Producing Potential," Plant Physiol., (1986), 81:1027-1032.
Mooibroek, H. et al., "Alternative sources of natural rubber," Appl Microbiol Biotechnol, (2000), 53:355-365.
Nawamawat, Kanjanee et al., "Surface nanostructure of Hevea brasiliensis natural rubber latex particles," Colloids and Surfaces A: Physicochemical and Engineering Aspects, (2011), 390:157-166.
Oldham, Michael L., et al., "The structure of coral allene oxide synthase reveals a catalase adapted for metabolism of a fatty acid hydroperoxide," PNAS, (2005), 102(2):297-302.
Ohya, Norimasa et al., "Activity of Rubber Transferase and Rubber Particle Size in Hevea Latex," J. Rubb. Res., (2000), 3(4):214-221.
Rojruthai, Porntip et al., "In vitro synthesis of high molecular weight rubber by Hevea small rubber particles," Journal of Bioscience and Bioengineering, (2010), 109(2):107-114.
Sakdapipanich, J. T. et al., "Structural Characterisation of the Small Rubber Particles in Fresh Hevea Latex," Journal of Rubber Research, (1999), 2(3):160-168.
Sansatsadeekul, Jitlada et al., "Characterization of associated proteins and phospholipids in natural rubber latex," Journal of Bioscience and Bioengineering, (2011), 111(6):628-634.
Hirschey, Matthew D. et al.,, Sirtuins: Methods and Protocals, Methods in Molecular Biology, 1077:1-311.
Tosha, Takehiko et al., "On the Relationship of Coral Allene Oxide Synthase to Catalase—A Single Active Site Mutation That Induces Catalase Activity in Coral Allene Oxide Synthase," The Journal of Biological Chemistry, (2006), 281(18): 12610-12617.
Van Beilen, Jan B. et al., "Establishment of new crops for the production of natural rubber," Trends in Biotechnology, (2007), 25(11):522-529.
Kim, Jeong et al., "A novel cDNA from Parthenium argentatum Gray enhances the rubber biosynthetic activity in vitro", (2004) Journal of Experimental Botany 55(396):377-385.
Pan, Zhigiang et al., "The Major Protein of Guayule Rubber Particles is a Cytochrome P450", (1995) The Journal of Biological Chemistry 270(15):8487-8494.

* cited by examiner

FIG. 2

| Amplicon Name | Forward primer (5' to 3') | Reverse primer (5' to 3') | Annealing Temperature (°C) | Product Size (bp) |
|---|---|---|---|---|
| *PaAOS*<sub>OE</sub> | cttaagaggtggtATGGACCCATCGTCTAAACCC SEQ ID NO: 1 | ggatccTCATATACTAGCTCTCTTCAGGG SEQ ID NO: 2 | 70 | 1,422 |
| *PaAOS*<sub>RNAi</sub> | ATGAGCCCAGAACGACGGCCCGGGCC SEQ ID NO: 3 | GATCTCGGTGACGGGCAGGACCGG SEQ ID NO: 4 | 72 | 551 |
| *18S* | CAACAAACCCCGACTTCTGG SEQ ID NO: 5 | CACCCGTCACCACCATAGTA SEQ ID NO: 6 | 60 | 190 |
| *PaAOS* | AACCGGAAGAGAAACCAAACT SEQ ID NO: 7 | CGCAACCGACTGGAAATAAT SEQ ID NO: 8 | 56 | 195 |

FIG. 3

| P. argentatum Genotypes | Height (cm) | | | Width (cm) | | | Shoot Biomass (g) | | | Root Biomass (g) | |
|---|---|---|---|---|---|---|---|---|---|---|---|
| | 27°C (16h) / 25°C (8h) | 27°C (16h) / 10°C (8h) | | 27°C (16h) / 25°C (8h) | 27°C (16h) / 10°C (8h) | | 27°C (16h) / 25°C (8h) | 27°C (16h) / 10°C (8h) | | 27°C (16h) / 25°C (8h) | 27°C (16h) / 10°C (8h) |
| G7-11.1 | 21.0 ± 3.8 | 23.3 ± 0.2 | | 24.1 ± 5.1 | 24.3 ± 2.1 | | 6.3 ± 1.4 | 4.0 ± 0.7 | | 1.2 ± 0.2 | 0.8 ± 0.1 |
| G7-11.2 | 25.0 ± 1.2 | 22.3 ± 0.6 | | 22.3 ± 3.1 | 21.3 ± 2.1 | | 4.6 ± 0.1 | 5.5 ± 0.9 | | 1.1 ± 0.1 | 1.0 ± 0.03 |
| pND6-10 | 25.5 ± 2.3 | 23.7 ± 2.8 | | 28.7 ± 3.6 | 25.7 ± 1.2 | | 5.7 ± 1.4 | 5.4 ± 0.6 | | 1.0 ± 0.3 | 1.1 ± 0.1 |
| pND6-12 | 25.0 ± 3.6 | 23.3 ± 2.1 | | 24.0 ± 3.6 | 23.0 ± 2.6 | | 6.1 ± 1.4 | 3.6 ± 1.0 | | 0.9 ± 0.1 | 0.9 ± 0.2 |
| pND6-35 | 22.7 ± 3.3 | 23.9 ± 1.0 | | 29.2 ± 4.3 | 27.0 ± 1.7 | | 5.7 ± 0.1 | 5.2 ± 0.7 | | 1.2 ± 0.1 | 1.1 ± 0.05 |
| pND6-AosiL$_{7-2}$ | 31.5 ± 0.4** | 31.3 ± 2.5** | | 31.8 ± 1.4* | 31.0 ± 1.7** | | 17.5 ± 5.5** | 15.8 ± 2.8** | | 2.8 ± 0.9** | 2.5 ± 0.7*** |
| pND6-AosiL$_{8-1}$ | 33.8 ± 2.4** | 30.8 ± 2.8* | | 33.3 ± 1.5** | 31.5 ± 1.3** | | 11.6 ± 2.7** | 9.7 ± 1.5** | | 2.7 ± 0.9** | 2.7 ± 0.1*** |
| pND6-AosiL$_{9-16}$ | 34.0 ± 1.7** | 31.3 ± 1.2** | | 31.2 ± 0.8* | 32.0 ± 2.6** | | 10.7 ± 0.9** | 11.2 ± 1.6** | | 2.4 ± 0.8** | 2.3 ± 0.5*** |
| pND6-AosiL$_{12-1}$ | 30.2 ± 0.2** | 30.5 ± 3.7* | | 33.4 ± 4.1* | 37.2 ± 3.0** | | 9.5 ± 0.9** | 10.5 ± 2.5** | | 2.4 ± 0.4** | 2.4 ± 0.2*** |
| pND6-Aos$_{E4-2}$ | 24.3 ± 1.5 | 22.0 ± 2.6 | | 24.2 ± 0.2 | 20.5 ± 1.8 | | 4.0 ± 1.0 | 5.3 ± 0.8 | | 0.9 ± 0.4 | 1.2 ± 0.3 |
| pND6-Aos$_{8-2}$ | 25.8 ± 1.8 | 23.5 ± 1.3 | | 27.2 ± 1.6 | 22.3 ± 0.6 | | 4.6 ± 0.3 | 6.1 ± 0.4 | | 1.1 ± 0.1 | 1.0 ± 0.04 |
| pND6-Aos$_{5-1}$ | 25.3 ± 1.5 | 21.0 ± 1.0 | | 25.3 ± 1.0 | 23.5 ± 0.5 | | 7.3 ± 0.2 | 4.3 ± 1.0 | | 1.0 ± 0.4 | 1.4 ± 0.05 |
| pND6-Aos$_{7-1}$ | 24.3 ± 2.1 | 21.2 ± 2.0 | | 24.2 ± 0.2 | 20.5 ± 1.8 | | 5.2 ± 1.4 | 4.4 ± 0.8 | | 0.9 ± 0.3 | 0.8 ± 0.2 |

FIG. 5

| Condition | 27°C (16h) / 25 °C (8h) | | | | 27°C (16h) / 10°C (8h) | | | |
|---|---|---|---|---|---|---|---|---|
| *P. argentatum* Genotypes | Number of branches per plant | | | | Number of branches per plant | | | |
| | Plant 1 | Plant 2 | Plant 3 | Plant 4 | Plant 1 | Plant 2 | Plant 3 | Plant 4 |
| *G7-11.1* | 1 | 2 | 4 | - | 3 | 4 | 4 | - |
| *G7-11.2* | 1 | 2 | 3 | 4 | 1 | 1 | 3 | 5 |
| *pND6-10* | 1 | 3 | 4 | 0 | 3 | 4 | 5 | - |
| *pND6-12* | 2 | 3 | 4 | - | 2 | 3 | 3 | - |
| *pND6-35* | 1 | 2 | 3 | 3 | 1 | 1 | 4 | 1 |
| *pND6-AosiL$_{7-2}$* | 6 | 8 | - | - | 8 | 8 | 9 | 10 |
| *pND6-AosiL$_{8-1}$* | 7 | 8 | 9 | 10 | 8 | 8 | 10 | 11 |
| *pND6-AosiL$_{9-16}$* | 5 | 8 | 10 | - | 8 | 8 | 9 | 10 |
| *pND6-AosiL$_{12-1}$* | 4 | 5 | 6 | - | 5 | 6 | 6 | 6 |
| *pND6-Aos4-1* | 3 | 3 | 3 | - | 4 | 4 | 5 | - |
| *pND6-Aos4-2* | 1 | 3 | 3 | - | 1 | 3 | 3 | 5 |
| *pND6-Aos5-1* | 2 | 3 | 4 | 5 | 3 | 5 | 5 | - |
| *pND6-Aos7-1* | 3 | 3 | 4 | - | 3 | 3 | 4 | 4 |

| *P. argentatum* Genotypes | Stem Diameter (mm) | |
|---|---|---|
| | 27°C (16h) / 25 °C (8h) | 27°C (16h) / 10°C (8h) |
| *G7-11.1* | 0.8 ± 0.3 | 0.9 ± 0.01 |
| *G7-11.2* | 1.3 ± 0.2 | 1.3 ± 0.2 |
| *pND6-10* | 1.2 ± 0.3 | 0.9 ± 0.3 |
| *pND6-12* | 0.7 ± 0.1 | 1.1 ± 0.03 |
| *pND6-35* | 1.1 ± 0.1 | 1.2 ± 0.1 |
| *pND6-AosiL$_{7-2}$* | 2.4 ± 0.7* | 1.7 ± 0.2 |
| *pND6-AosiL$_{8-1}$* | 2.0 ± 0.3* | 2.1 ± 0.2** |
| *pND6-AosiL$_{9-16}$* | 1.8 ± 0.01* | 1.7 ± 0.1*** |
| *pND6-AosiL$_{12-1}$* | 1.6 ± 0.1* | 2.2 ± 0.2*** |
| *pND6-Aos4-1* | 1.0 ± 0.2 | 1.3 ± 0.1 |
| *pND6-Aos4-2* | 1.1 ± 0.1 | 1.3 ± 0.04 |
| *pND6-Aos5-1* | 1.0 ± 0.01 | 1.4 ± 0.0004 |
| *pND6-Aos7-1* | 1.1 ± 0.2 | 0.9 ± 0.1 |

PaAOS relative expression and rubber content analyzed by ASE in one month old soil-grown G7-11 plants treated with salicylic acid for 2 months and grown in greenhouse settings.

| Treatment (Nov 2016-Jan 2017) | Height (cm) | Stembark diameter (mm) | PaAOS relative expression | % rubber content |
|---|---|---|---|---|
| Mock (water + 0.0005% EtOH) | 18.9±2.3 | 37.0±7.4 | 2.46±1.67 | 0.63±0.12 |
| Salicylic acid (10 nM) | 25.0±2.4* | 3.071±0.422 | 0.44±0.07* | 0.91±0.04* |

FIG 9A

Single Nucleotide Polymorphisms in the PaAos coding sequence.

```
W6549    ATGGACCCATCGTCTAAACCCCTCCGTGAAATCCCCGGCTCTTATGGCATTCCTTCTTCTTCAACCGATAAAAGACCGATT    SEQ ID NO. 12
G711     ATGGACCCATCGTCTAAACCCCTCCGTGAAATCCCCGGCTCTTATGGCATTCCTTCTTCTTCAACCGATAAAAGACCGATT    SEQ ID NO. 9
478652   ATGGACCCATCGTCGTTAAACCCCTCGTGAAATCCCCGGCTCTTATGGCATTCCTTCTTCTTCAACCGATAAAAGACCGATT    SEQ ID NO. 14
         ************** ****************************************************************

W6549    GGAGTATTTTACGGGACCGGAGGTGAGACGAGTACTTCCGGTCCCGCATGCAAAATACCAATCCACGGTATTTCGAAG      SEQ ID NO. 12
G711     GGAGTATTTTACGGGACCGGAGGTGAGACGAGTACTTCCGGTCCCGCATGCAAAATACCAATCCACGGTATTTCGAAG      SEQ ID NO. 9
478652   GGAGTATTTTACGGGACCGGAGGTGAGACGAGTACTTCCGGTCCCGCATGCAAAATACCAATCCACGGTATTTCGAAG      SEQ ID NO. 14
         ****************************************************************************

W6549    CCAACATGCCACCGGGCCCTTTCGTAAGCAGCAACCGAAGGTCATCGTCCTACTCGACGTCGACGCCAA GCTTTCCGATACTC    SEQ ID NO. 12
G711     CCAACATGCCACCGGGCCCTTTCGTAAGCAGCAACCGAAGGTCATCGTCCTACTCGACGTCGACGCCAA GCTTTCCGATACTC    SEQ ID NO. 9
478652   CCAACATGCCACCGGGCCCTTTCGTAAGCAGCAACCGAAGGTCATCGTCCTACTCGACGTCGACGCCAA GCTTTCCGATACTC    SEQ ID NO. 14
         ********************************************************************  **********

W6549    TTTGATGTATCCAAAGTCGAGAAGAAAGATTTGTTCACCGGAACTTACATGCCGTCAACCAAACTCACTGGCGGCTACCG    SEQ ID NO. 12
G711     TTTGATGTATCCAAAGTCGAGAAGAAAGATTTGTTCACCGGAACTTACATGCCGTCAACCAAACTCACTGGCGGCTACCG    SEQ ID NO. 9
478652   TTTGATGTATCCAAAGTCGAGAAGAAAGATTTGTTCACCGGAACTTACATGCCGTCAACCAAACTCACTGGCGGCTACCG    SEQ ID NO. 14
         ****************************************************************************

W6549    CGTACTTCGTACTTCGACCATTCCGAACCTAGACATGCTC G AGAACCTTCTTGTTCTTCATGCTTAAAATTCAA         SEQ ID NO. 12
G711     CGTACTTCGTACTTCGACCATTCCGAACCTAGACATGCTC G AGAACCTTCTTGTTCTTCATGCTTAAAATTCAA         SEQ ID NO. 9
478652   CGTACTTCGTACTTCGACCATTCCGAACCTAGACATGCTC A AGAACCTTCTTGTTCTTCATGCTTAAAATTCAA         SEQ ID NO. 14
         ********************************************  ******************************

W6549    GCAACCGAGTCATTCCTCAGTTCGAAACCACTTACACCGAACTCTTTGAAGGTCTTGAAGCGAGCTAGCCAAAAACGGG    SEQ ID NO. 12
G711     GCAACCGAGTCATTCCTCAGTTCGAAACCACTTACACCGAACTCTTTGAAGGTCTTGAAGCGAGCTAGCCAAAAACGGG    SEQ ID NO. 9
478652   GCAACCGAGTCATTCCTCAGTTCGAAACCACTTACACCGAACTCTTTGAAGGTCTTGAAGCGAGCTAGCCAAAAACGGG    SEQ ID NO. 14
         ****************************************************************************
```

FIG. 9B

```
W6549   AAAGCCGCGTTCAACGATGTTGGTGAACAAGCGGCTTTCCGGTTTTTGGGCAGGGCTTATTTAACTGAACCCGGAAGA   SEQ ID NO. 12
G711    AAAGCCGCGTTCAACGATGTTGGTGAACAAGCGGCTTTCCGGTTTTTGGGCAGGGCTTATTTAACTGAACCCGGAAGA   SEQ ID NO. 9
478652  AAAGCCGCGTTCAACGATGTTGGTGAACAAGCGGCTTTCCGGTTTTTGGGCAGGGCTTATTTAACTGAACCCGGAAGA   SEQ ID NO. 14
        ******************************************************************************

W6549   AACCAAACTAGGAACTAGTGCGCCTACGTTAATTAGCTCGTGGGTGTTATTTAATCTTGCCCCACGCTCGACTCGGAC   SEQ ID NO. 12
G711    AACCAAACTAGGAACTAGTGCGCCTACGTTAATTAGCTCGTGGGTGTTATTTAATCTTGCCCCACGCTCGACTCGGAC   SEQ ID NO. 9
478652  AACCAAACTAGGAACTAGTGCGCCTACGTTAATTAGCTCGTGGGTGTTATTTAATCTTGCCCCACGCTCGACTCGGAC   SEQ ID NO. 14
        ******************************************************************************

W6549   TTCCGTGGTTCTTGCAGGAACCTCTTCTACACACTTTCCGACTGCCGGCGTTCCTGATTAAGAGTACTTACAACAAACTT   SEQ ID NO. 12
G711    TTCCGTGGTTCTTGCAGGAACCTCTTCTACACACTTTCCGACTGCCGGCGTTCCTGATTAAGAGTACTTACAACAAACTT   SEQ ID NO. 9
478652  TTCCGTGGTTCTTGCAGGAACCTCTTCTACACACTTTCCGACTGCCGGCGTTCCTGATTAAGAGTACTTACAACAAACTT   SEQ ID NO. 14
        ********************************************************************************

W6549   TACGATTATTTCCAGTCGGTTGCGACTCCGGTTATGGAACAAGCAGAAAATTAGGGTTCCGAAGGATGAAGCTGTGCA   SEQ ID NO. 12
G711    TACGATTATTTCCAGTCGGTTGCGACTCCGGTTATGGAACAAGCAGAAAATTAGGGTTCCGAAGGATGAAGCTGTGCA   SEQ ID NO. 9
478652  TACGATTATTTCCAGTCGGTTGCGACTCCGGTTATGGAACAAGCAGAAAATTAGGGTTCCGAAGGATGAAGCTGTGCA   SEQ ID NO. 14
        ******************************************************************************

W6549   CAATATCTTATTCGCGGTTTGCTTCAATACTTTTGGTGGTG[A]AGATCCTCTTCCGAATACACTCAAATGGATCGGAC   SEQ ID NO. 12
G711    CAATATCTTATTCGCGGTTTGCTTCAATACTTTTGGTGGTG[A]AGATCCTCTTCCGAATACACTCAAATGGATCGGAC   SEQ ID NO. 9
478652  CAATATCTTATTCGCGGTTTGCTTCAATACTTTTGGTGGTG[T]AGATCCTCTTCCGAATACACTCAAATGGATCGGAC   SEQ ID NO. 14
        *****************************************  ***********************************

W6549   TTGCTGGTGAGAATTTGCATACCCAATTGGCGGAAGAGATTAGAGGTGCTATAAAATCATACGGGGACGGTAACGTGACG   SEQ ID NO. 12
G711    TTGCTGGTGAGAATTTGCATACCCAATTGGCGGAAGAGATTAGAGGTGCTATAAAATCATACGGGGACGGTAACGTGACG   SEQ ID NO. 9
478652  TTGCTGGTGAGAATTTGCATACCCAATTGGCGGAAGAGATTAGAGGTGCTATAAAATCATACGGGGACGGTAACGTGACG   SEQ ID NO. 14
        ********************************************************************************
```

FIG. 9C

```
W6549    CTGGAAGCAATCGAGCAGATGCCGTTGACGACGAAGTCAGTGGTGTACGAGTCCCTCAGGATTGAACCACCAGTGCCTCCGCA    SEQ ID NO. 12
G711     CTGGAAGCAATCGAGCAGATGCCGTTGACGACGAAGTCAGTGGTGTACGAGTCCCTCAGGATTGAACCACCAGTGCCTCCGCA    SEQ ID NO. 9
478652   CTGGAAGCAATCGAGCAGATGCCGTTGACGACGAAGTCAGTGGTGTACGAGTCCCTCAGGATTGAACCACCAGTGCCTCCGCA    SEQ ID NO. 14
         ********************************************************************************

W6549    ATATGGAAAAGCCAAAAGCAACTTTACCATAGAGTCACACGACGCCACTTTCGAAGTCAAAAAAGGAGAAATGTTATTCG    SEQ ID NO. 12
G711     ATATGGAAAAGCCAAAAGCAACTTTACCATAGAGTCACACGACGCCACTTTCGAAGTCAAAAAAGGAGAAATGTTATTCG    SEQ ID NO. 9
478652   ATATGGAAAAGCCAAAAGCAACTTTACCATAGAGTCACACGACGCCACTTTCGAAGTCAAAAAAGGAGAAATGTTATTCG    SEQ ID NO. 14
         ********************************************************************************

W6549    GGTACCAACCGTTTGCAACCAAGGACCCAAAAGTATTTGACCGACCCGAGGAATATGTCCCTGATCGGTTCGTTGGGGAT    SEQ ID NO. 12
G711     GGTACCAACCGTTTGCAACCAAGGACCCAAAAGTATTTGACCGACCCGAGGAATATGTCCCTGATCGGTTCGTTGGGGAT    SEQ ID NO. 9
478652   GGTACCAACCGTTTGCAACCAAGGACCCAAAAGTATTTGACCGACCCGAGGAATATGTCCCTGATCGGTTCGTTGGGGAT    SEQ ID NO. 14
         ********************************************************************************

W6549    GGCGAGGCATTGTTGAAGTACAATGGTGTTAATGGGCCGGAGACAGAGAGTCCGACAGTTGAAGATAAACAATGTGC    SEQ ID NO. 12
G711     GGCGAGGCATTGTTGAAGTACAATGGTGCCTAATGGGCCGGAGACAGAGAGTCCGACAGTTGAAGATAAACAATGTGC    SEQ ID NO. 9
478652   GGCGAGGCATTGTTGAAGTACGATGGTGTTTAATGGGCCGGAGACAGAGAGTCCGACAGTTGAAGATAAACAATGTGC    SEQ ID NO. 14
         ********************************************************************************

W6549    CGGAAAAGACTTTGTTTGCTTATAACGAGGTTGTTGTTTGTCATTGAACTTTTCCGGCGATATGACTCTTGAAATCGAAT    SEQ ID NO. 12
G711     CGGAAAAGACTTTGTTTGCTTATAACGAGGTTGTTGTTTGTCATTGAACTTTTCCGGCGATATGACTCTTGAAATCGAAT    SEQ ID NO. 9
478652   CGGAAAAGACTTTGTCTGCTTATAACGAGGTTGTTGTTTGTCATTGAACTTTTCCGGCGATATGACTTTTGAAATCGAAT    SEQ ID NO. 14
         ********************************************************************************

W6549    TAGGCGAGTCTCCTTGGTGCAGCTGTCACACTTACGTCCCTGAAGAGAGCTAGTATATGA    SEQ ID NO. 12
G711     TAGGCGAGTCTCCTTGGTGCAGCTGTCACACTTACGTCCCTGAAGAGAGCTAGTATATGA    SEQ ID NO. 9
478652   TAGGCGAGTCTCCTTGGTGCAGCTGTCACACTTACGTCCCTGAAGAGAGCTAGTATATGA    SEQ ID NO. 14
         ************************************************************
```

FIG. 10

Protein mutations arising from Single Nucleotide Polymorphisms in the PaAos coding sequence.

```
W6549    MDPSSKPLREIPGSYGIPFFQPIKDRLEYFYGTGGRDEYFRSRMQKYQSTVFRAWMPPGPFVSSNPKVIVLLDAKSFPIL    SEQ ID NO. 13
G711     MDPSSKPLREIPGSYGIPFFQPIKDRLEYFYGTGGRDEYFRSRMQKYQSTVFRAWMPPGPFVSSNPKVIVLLDAKSFPIL    SEQ ID NO. 10
478652   MDPSSKPLREIPGSYGIPFFQPIKDRLEYFYGTGGRDEYFRSRMQKYQSTVFRAWMPPGPFVSSNPKVIVLLDAKSFPIL    SEQ ID NO. 15
         ********************************************************************************

W6549    FDVSKVEKKDLFTGTYMPSTKLTGGYRVLSYLDPSEPRHAQLKNLLFFMLKNSSNRVIPQFETTYTELFEGLEAELAKNG    SEQ ID NO. 13
G711     FDVSKVEKKDLFTGTYMPSTKLTGGYRVLSYLDPSEPRHAQLKNLLFFMLKNSSNRVIPQFETTYTELFEGLEAELAKNG    SEQ ID NO. 10
478652   FDVSKVEKKDLFTGTYMPSTKLTGGYRVLSYLDPSEPRHAQLKNLLFFMLKNSSNRVIPQFETTYTELFEGLEAELAKNG    SEQ ID NO. 15
         ********************************************************************************

W6549    KAAFNDVGEQAAFRFLGRAYFNSNPEETKLGTSAPTLISSWLFNLAPTLDLGLPWFLQEPLLHTFRLPAFLIKSTYNKL    SEQ ID NO. 13
G711     KAAFNDVGEQAAFRFLGRAYFNSNPEETKLGTSAPTLISSWLFNLAPTLDLGLPWFLQEPLLHTFRLPAFLIKSTYNKL    SEQ ID NO. 10
478652   KAAFNDVGEQAAFRFLGRAYFNSNPEETKLGTSAPTLISSWLFNLAPTLDLGLPWFLQEPLLHTFRLPAFLIKSTYNKL    SEQ ID NO. 15
         *******************************************************************************

W6549    YDYFQSVATPVMEQAEKLGVPKDEAVHNILFAVCFNTFGGVKILFPMTLKWIGLAGENLHTQLAEEIRGAIKSYGDCVT    SEQ ID NO. 13
G711     YDYFQSVATPVMEQAEKLGVPKDEAVHNILFAVCFNTFGGVKILFPMTLKWIGLAGENLHTQLAEEIRGAIKSYGDCVT    SEQ ID NO. 10
478652   YDYFQSVATPVMEQAEKLGVPKDEAVHNILFAVCFNTFGGVKILFPNTLKWIGLAGENLHTQLAEEIRGAIKSYGDCVT    SEQ ID NO. 15
         ***********************************************************************  *

W6549    LEAIEQMPLIKSVVYESLRIEPPVPPQYGKAKSNFTIESHDATFEVKKGEMLFGYQPFATKDPKVFDRPEEYVPDRFVGD    SEQ ID NO. 13
G711     LEAIEQMPLIKSVVYESLRIEPPVPPQYGKAKSNFTIESHDATFEVKKGEMLFGYQPFATKDPKVFDRPEEYVPDRFVGD    SEQ ID NO. 10
478652   LEAIEQMPLIKSVVYESLRIEPPVPPQYGKAKSNFTIESHDATFEVKKGEMLFGYQPFATKDPKVFDRPEEYVPDRFVGD    SEQ ID NO. 15
         ********************************************************************************

W6549    GEALLKYIWENGPETESPTVENKQCAGKDFWLITRLFVIELFRRYDSFEIELGESPLGAAVTLTSLKRASI    SEQ ID NO. 13
G711     GEALLKYIWPNGPETESPTVENKQCAGKDFWLITRLFVIELFRRYDSFEIELGESPLGAAVTLTSLKRASI    SEQ ID NO. 10
478652   GEALLKYWWSNGPETESPTVENKQCAGKDFWLITRLFVIELFRRYDSFEIELGESPWGAAVTLTSLKRASI    SEQ ID NO. 15
         *******  ***********************************************  ***********
```

FIG. 11A

AATCCAGCTAAGTCTAACTGTAATATTCAACTAAGTAAATTAGTTATGTTTGTAGGAAAGTAACATAAATTGCC

GGGTGTCACATCTTATGTCCGATTAACCCCTTACTCAACCCAATACTAGCCATTGATAACCTTATCTAATCTCCTTCC
WRKY71

TGTAATTGTCATTCATTGAAACATGAAACACGGATCTATTTCATTCTCATGTTGTTCAATTATTCTTTCTCGTTATATGA
WRKY71

TTCAAAGAGGTCAAACTTCTCTAAGTTTGAGTGTGGCCACGCATTACACCAGTTGGATCAACGAGGGTCCAGAATA
WRKY71

CACAACTTTTTATAATAAAGAAGAACAGAATTCCTTGACAACATACAACTCCCACTTAACCTTAGGTATGCTCCAA
WRKY71

CCAAATACCCTATTGTTGTCTTTTCACGATACAGTGTTAGGAAAGATTAAAGAACAAACTTTAGGCAAATGTTAGTTC

CAATATGTCTCTCAGTTCAAAGGACATTTAGATCATATCAATTTCAAAATATCACATGACTTTGATCTTTAGAGATCATT
WRKY71

TAGAAACGAGTTAGTCAAATATCACTCCTAATGTATATCAGTGAACTGGCCCTCAACACCTTTAGATTTCATCTCAT
WRKY71

GAACAAACAATCACTCACATAGTCATAATTGAATTGATTCCCTTGAATTGACTACGGACATTTGAATACTTT
WRKY71

TATTCATGTATACTTAAACGTACAAAATTGAACATAGCAACACAATTTATAATGCATTCAACCTTTAAATTAAAATAA

AGAAATGTAGCTATCAATTGTTCAAAGCACCAAATACTAATAGATCAAACCACTCTCTAGCATTCCTTAACCCTATACG

FIG. 11B

AGGCGTATAGGTACAAACCAATGCACTTATTATGCAGACATGGAAATTGTGAACGTAACACGACTGTATAGGCAA

TACGAGATGTATCTGGGGCGTGTAAATAACGATTGAGGGTGTGGAAATATTATGGCCCTTAAATTAAGGGATATTCAT

TGCCTATAAATTATCGCAAAGCGGGTATATATTAAATACTTTCTATATTGTACCATCACTATATATATATATATATAT

ATATATATATATATATATATATATATATATATATAACCTACACATGAAAATATATAAGCAGGTATCTTTAAATTTTATAAAACT

GCTTCAAAATTCAGGCATAACGAGCATAACGAAACTTTATAAGATTTATGTATGATTCATAACGAATCTCTATCAAAAA

CATATTCAATCAAGACAATGTGTAGCATATGGGTTAATTACATGCACATACACTTCTTCATAACATTAAAATTTAAAT

TTAATATTATTTTATAATGCGTGTACAAATCAAACATTGTTTAAGTTCTTTTATAGCAACTGTCACGTTTAAAATTTGCT
                                                                    WRKY71

CACCGTAATCAGTAGGAAAATATTAAAAGATTATAAAACGAAGTAAACAATGTATAAAAAATAAAAAGACTAGAA

CCTAAGGGCCGTCAGCTCGTCTTTATATACAGTAGTTCATTCATCAAATACGCACCATTTCTCACACTCAACATTT
         WRKY71

TCTCACACAAACATGGATCCATCATCTGAAGCCCTCCGTGAAATCCTGGTTCATACGGCATTCCTTTATCCAACC
                                                                    MYBS3

GATCAAAGACCGGTTGGAGTATTTTTACGGGACCGGAGGCCCAGATGGGTTCTTCCAGTCCCGGTTCAAAATACCAA

FIG. 11C

```
TCCACTGTGTTCCGAACCAATATGCCACCCGGCCCTTTATAAGCAGCAACCCAAAAGTCATTGTCCTCTTAGAGCGCCA
                                                                  WRKY71
AAAGCTTCCCGTATTGTTTGATGTTTCTAAAGTCGAGAAGAAAGATTTATTACCGAACTTATATGCCGTCAACTAAC
                                                                           WRKY71
CTCACTGGCGGCTACCGCGTACTCTCGTACATGACCATCCAAACAACTAGACATGCTCAACTAAGAACCTCTGTCTT
                                  CBF
CATGCTTAAAAATTCAAGCAACCGAGTCATTCCTCAGTTCCAAACAACTTACACCGAACTCTTTGAAGGTCTTGAAACC
                                     WRKY71
GAATTGGCCAAAAATGGGAAGCCCGGTTCAACGACGTTGGTGAACAAGCGGCTTTCCGGTTTTTGGGCCCGGGCTTATT
             FLC
TCAACTCTAACCCGGAGAAACCAAACTAGGAACTAGTGCCGGCCGAAGTTAATTACCACGTGGGTGTGTTCAATCTTAG
                                                                              CBF
CCCGATAGGCACTGCTGGACTTCCGTGGTTCTTGGAGGACCCTCTTATCCACACTTTCCGACTGCCGTCGTTCTGGTAA
                                                  MYBS3
AGAGTAACTACAACAAGCTTTACGATTATTTGAGTCGGCTGCGACTCAGGTTGTGGAGCAAGCAGAAATATTAGGGG
                                       CBF
TTCCGAAAGATGAAGCTTTTGCACATATCTTATTCGCGGTTGCTTCAATACTTTGAAAATACGCAAAAGTAAAA

AATAAAATAAAAGAACCTAAGGTACATCCTCGTCTATATATACACTTGTTTTTATTCATCCAAAATAAACACACCATC

TTCTCACTCAAAACAGTCAAAAC              SEQ ID NO: 18
     WRKY71
```

FIG. 12

| Primer Name | Forward primer (5' to 3') | Reverse primer (5' to 3') | Annealing Temp. (°C) | Product Size (bp) |
|---|---|---|---|---|
| RT-PCR WRKY3-like | AACCGCAGTCTACACGAAGA (SEQ ID NO: 19) | TCGAAGAATTATCCGGCGTG (SEQ ID NO: 20) | 58 | 162 |
| RT-PCR WRKY71-like | TGTGGCTTGTGGAGTGAAGA (SEQ ID NO: 21) | ACCACCACTGAAACCACCAT (SEQ ID NO: 22) | 58 | 166 |
| RT-PCR MYBS3-like | CTTGGTCCGAAGACGAACAT (SEQ ID NO: 23) | GGCTTGAACGACGTTCTTC (SEQ ID NO: 24) | 58 | 180 |
| pND6 | CCGTCCCAAGCAGTTACAAT (SEQ ID NO: 25) | TACGTGTTCAGTGGTTCCCA (SEQ ID NO: 26) | 58 | 618 |
| 18S | CAACAAACCCGACTTCTGG (SEQ ID NO: 5) | CACCCGTCACCACCATAGTA (SEQ ID NO: 6) | 60 | 190 |
| PaAos | AACCCGGAAGAAACCAAACT (SEQ ID NO: 7) | CGCAACCGACTGGAAATAAT (SEQ ID NO: 8) | 56 | 195 |
| PaWRKY3-like | cttaagATGTCTGCACAATCTTTTCAGAG (SEQ ID NO: 27) | ggatccTTAACAAAAGCACAAAAGAAAAAC (SEQ ID NO: 28) | 58 | 786 |
| PaWRKY71-like | cttaagATGTTAAAGATTGAACCAATTTTTGTT (SEQ ID NO: 29) | ggatccTTAGTTCTGTTCTTCTTTGGC (SEQ ID NO: 30) | 58 | 540 |
| PaMYBS3-like | cttaagATGGTAACATATAGGAGGGGTT (SEQ ID NO: 31) | ggatccTTATGGGTTGTACCTTGCTTTAAAA (SEQ ID NO: 32) | 58 | 369 |
| pND6-WRKY3-like | cttaagaggtggtATGTCTGc (SEQ ID NO: 33) | TTAACAAAAGCACAAAAGAAAAAC (SEQ ID NO: 34) | 57 | 800 |
| pND6-WRKY71-like | cttaagaggtggtATGTTAAAGA (SEQ ID NO: 35) | TTAGTTCTGTTCTTCTTTGGC (SEQ ID NO: 36) | 58 | 550 |
| pND6-MYBS3-like | cttaagaggtggtATGGTAAC (SEQ ID NO: 37) | TTATGGGTTGTACCTTGCTTTAAAA (SEQ ID NO: 38) | 58 | 400 |

GUAYULE WITH INCREASED RUBBER PRODUCTION AND YIELD

CROSS REFERENCE TO RELATED APPLICATIONS

This patent application claims priority to U.S. Patent Application 62/504,762 filed on May 11, 2017, contents of which are expressly incorporated by reference herein.

BACKGROUND OF THE INVENTION

Sequence Listing

The Sequence Listing submitted via EFS-Web as ASCII compliant text file format (.txt) filed on May 10, 2018, named "SequenceListing_ST25", (created on May 9, 2018, 50 KB), is incorporated herein by reference. This Sequence Listing serves as paper copy of the Sequence Listing required by 37 C.F.R. § 1.821(c) and the Sequence Listing in computer-readable form (CRF) required by 37 C.F.R. § 1.821(e). A statement under 37 C.F.R. § 1.821(f) is not necessary.

FIELD OF THE INVENTION

This invention relates to altered guayule plants that grow larger and produce more rubber than non-altered guayule plants, when grown under the same conditions. The altered guayule contain the cDNA sequence of *Parthenium argentatum* Allene oxide synthase (PaAos) in the reverse complement orientation under control of a heterologous promoter which reduces the production of PaAos via RNAi. Other types of genetic alternations can be made in guayule to reduce the functionality of PaAos. Methods of increasing rubber yield in guayule via reducing PaAos translation and/or reducing the amount of functional PaAos in plants are also included.

DESCRIPTION OF RELATED ART

Natural rubber is synthesized by more than 2,500 plant species (Cornish, et al., *J. Nat. Rubber Research* 8:275-285 (1993); Cornish, K., *Phytochemistry* 57:1123-1134 (2001)). Rubber is produced by these plants as a secondary metabolite with no clear indication of its function in plant cells. Possible reasons on why these species synthesize rubber are to defend themselves against pathogens and insect attacks, repair tissue damages caused by mechanical wounding and protect cell damage induced by environmental stresses (Demel, et al., *Biochim. Biophys. Acta.* 1375:36-42 (1998); Tangpakdee and Tanaka, *J. Rubber Res.* 1:14 (1998); Vereyken, et al., *Biochim. Biophys. Acta,* 1510:307-320 (2001); Kim, et al., *Plant Cell Physiol.,* 412-414 (2003) and references therein; Konno, K., *Phytochemistry,* 1510-1530 (2011); and Sarkar, J., *Rubber Science,* 228-237 (2013)). According to a 2014 market report, the rubber that these plants produce accounted for $16.5 billion in trade worldwide (rubberworld.com/RWmarket_report.asp). Even more so, the end products made from natural rubber, including tires for the transportation industry, sports equipment, medical devices, and more, are indispensable in our everyday life. The Hevea tree is the main source of natural rubber but concerns exist as it is limited geographically to tropical climates, mainly in Southeast Asia, is susceptible to diseases, and produces rubber that causes allergic reactions. Clearly, an alternative source for the production of natural rubber is very important to reduce economic risk and safeguard human health.

One plant known to be a promising source of natural rubber is guayule (*Parthenium argentatum*, Gray), a desert shrub native to the southwestern United States and northern Mexico (Mooibroek and Cornish, *Appl. Microbio. and Biochem.* 53:355-365 (2000); van Beilen and Poirier, *Critical Reviews Biotech.* 27:217-231 (2007)). The majority of rubber synthesis in guayule occurs during the cold season. Guayule synthesizes rubber within subcellular organelles called rubber particles (Archer and Audley, *Bot. J. Linnean Soc.* 94:181-196 (1987)) stored in the parenchyma cells of stembark tissues (Gilliland, M. v., *Protoplasma,* 169-177 (1984)); Macrae, S. G., *Plant Physiol.,* 1027-1032 (1986)). Natural rubber synthesis is initiated by the action of allylic pyrophosphates initiators (Cornish and Siler, *J. Plant Physiol.,* 301-305 (1995)), usually farnesyl pyrophosphate (FPP). Then, the monomer isopentenyl-pyrophosphate (IPP), produced by the mevalonic acid pathway (MEV) in the cytosol and the methylerythritol phosphate (MEP) pathway in the plastid (Mooibroek and Cornish (2000); van Beilen and Poirier, *TRENDS in Biotech.,* 522-529 (2007)) elongates the rubber chain. Rubber synthesis is mediated by rubber transferases requiring magnesium ions as cofactor (Da Costa, et al., *Phytochemistry* 67(15): 1621-1628 (2006)).

The proposed model for the structure of rubber particles consists mostly of hydrophobic cis-polyisoprene units (natural rubber) encapsulated inside a protein and phospholipid surface monolayer (Nawamawat, et al., *Colloids and Surfaces A: Physicochemical and Engineering Aspects,* 390: 157-166 (2011); Sansatsadeekul, et al., *J. Biosci. and Bioeng,* 111:628-634 (2011)). The phospholipids serve to stabilize and solubilize the otherwise insoluble (rubber) product. Guayule rubber particles include several proteins (Whalen, et al., *Development of crops to produce industrially useful natural rubber.* Chapter 23 in *Isoprenoid Synthesis in Plants and Microorganisms: New Concepts and Experimental Approaches,* Bach and Rohmer (eds.), DOI 10.1007/978-1-4614-4063-5_23, Springer Science+Business Media NY, 329-345 (2013)) of which Aos has been found to be the most abundant (Backhaus, et al., *Phytochemistry* 30:2493-2497 (1991)). Aos is well-known as an enzyme in the jasmonic acid biosynthetic pathway (Harms, et al., *Plant Cell,* 1645-1654 (1995); Wang, et al., *Plant Mol. Biol.,* 783-793 (1999); Schaller, F., *J. Exper. Botany,* 11-23 (2001)). The role of Aos in rubber biosynthesis, and the reason for the abundance of Aos protein on guayule rubber particle surfaces, is not known (Whalen, et al. (2013)).

The need exists for a method to increase rubber production in altered guayule compared to rubber production amounts in non-altered guayule in order to improve the commercial attractiveness of using guayule rubber as a replacement of synthetic rubber and Hevea rubber. Further, a need exists for increasing the rubber yield per acre obtained from altered guayule compared to the rubber yield per acre obtained from non-altered guayule. This greater rubber yield results from the altered guayule being larger in size than non-altered guayule of similar age. A need also exists for altered guayule that produce more rubber than the amount of rubber produced by non-altered guayule. A need also exists for altered guayule that have a larger size than similarly aged non-altered guayule because the altered guayule that are larger than the non-altered guayule will possess more tissue for storage of rubber and thus generate greater rubber yield per acre than the rubber yield per acre of non-altered guayule.

BRIEF SUMMARY OF THE INVENTION

It is an object of this invention to have an altered guayule (and progeny and parts thereof) that produces more rubber than the amount of rubber produced by a non-altered guayule. It is a further object of this invention that the alteration causes the altered guayule to produce a reduced amount of functional *Parthenium argentatum* Allene oxide synthase (PaAos) compared the amount of functional PaAos produced by non-altered guayule. It is another object of this invention that the reduced amount of functional PaAos causes more rubber to be produced by the altered guayule compared to the amount of rubber produced by non-altered guayule. It is another object of this invention that the reduced amount of functional PaAos causes the altered guayule to grow larger in size compared to the size of similarly aged non-altered guayule, and the larger sized altered guayule has an increased rubber yield per acre than the rubber yield per acre of similarly aged non-altered guayule. It is another object of this invention to have an altered guayule that produces a greater rubber yield per acre than the rubber yield per acre produced by a similarly aged non-altered guayule. It is a further object of this invention to have germplasm, pollen, flowers, seeds, stems, leaves, roots, cells, etc., of the altered guayule.

It is an object of this invention that the altered guayule contains an alteration in PaAos functionality. It is another object of this invention that the altered guayule contains an expression vector which further contains a heterologous promoter operably linked to a polynucleotide encoding PaAos anti-sense RNA and/or PaAos dsRNA and/or one or more guayule transcription factors, PaWRKY3-like (SEQ ID NOs: 39 and 40 and a sequence at least 95% identical thereof), PaWRKY71-like (SEQ ID NOs: 41 and 42 and a sequence at least 95% identical thereof), and/or PaMYBS3-like (SEQ ID NOs: 43 and 44 and a sequence at least 95% identical thereof), for overexpression of one or more of the transcription factors and/or the anti-sense RNA or dsRNA. It is further object of this invention that salicylic acid (SA) and/or PaAos dsRNA is administered to a non-altered guayule to make an altered guayule that produces more rubber than a non-altered guayule. It is another object that an altered guayule (containing one or more of the following: one or more expression vectors encoding PaAos anti-sense RNA, PaAos dsRNA (SEQ ID NO: 45), PaWRKY3-like, PaWRKY71-like, and/or PaMYBS3-like) is also treated with one or more of SA, PaAos dsRNA, and/or cold temperature (between approximately 7° C. and approximately 15° C. for approximately 8 hours per day), thereby causing the altered guayule to produce more rubber than is produced by a non-altered guayule and have great rubber yield per acre than non-altered guayule. It is a further object of this invention to have methods for creating the altered guayule. It is a further object of this invention to have altered guayule and parts thereof created by those methods.

It is an object of this invention that PaAos anti-sense RNA has a sequence that is the reverse complementary sequence of PaAos (SEQ ID NOs: 9, 12, or 14 or a sequence at least 95% identical thereof or any PaAos sequence in any guayule cultivar) or a fragment thereof (e.g., SEQ ID NO: 11 or a sequence at least 95% identical thereof, or any 19 contiguous nucleotides of SEQ ID NOs: 9, 12, or 14 or a sequence at least 95% identical thereof or any PaAos sequence in any guayule cultivar), such that the PaAos anti-sense RNA silences PaAos via RNAi in the altered guayule. It is another object of this invention that the dsRNA (either produced by the altered guayule or administered to the altered guayule) is at least 19 nucleotides long and contains a sense region selected from a portion of SEQ ID NO: 11 or a sequence at least 95% identical thereof, or any 19 contiguous nucleotides of SEQ ID NOs: 9, 12, or 14 or a sequence at least 95% identical thereof or any PaAos sequence in any guayule cultivar, or SEQ ID NO: 45), such that the dsRNA silences PaAos in the altered guayule which causes the altered guayule to produce more rubber than the amount of rubber produced by a non-altered guayule.

It is an object of this invention to have a method for increasing the amount of rubber produced by an altered guayule compared to the amount of rubber produced by a non-altered guayule. It is a further object that the method involves making one of the genetic alteration described supra in a non-altered guayule cell to produce a genetically altered guayule cell, such that the genetic alteration causes the genetically altered guayule to produce a reduced amount of functional PaAos compared the amount of functional PaAos produced by non-altered guayule cell and/or to produce an increased amount of one or more transcription factors (PaWRKY3-like, PaWRKY71-like, and/or PaMYBS3-like) compared to the amount of the one or more transcription factors produced by a non-altered guayule; selecting for a genetically altered guayule cell that produces (i) a reduced amount of functional PaAos compared to the amount of functional PaAos produced by a non-altered guayule cell and/or (ii) an increased amount of PaWRKY3-like, PaWRKY71-like, and/or PaMYBS3-like compared to the amount of PaWRKY3-like, PaWRKY71-like, and/or PaMYBS3-like produced by a non-altered guayule; and growing the selected genetically altered guayule cell into a genetically altered guayule that produces more rubber than the non-altered guayule. It is a further object of this invention that the lower amount of functional PaAos produced and/or increased amount of PaWRKY3-like, PaWRKY71-like, and/or PaMYBS3-like produced results in an increase in the amount of rubber produced by the genetically altered guayule compared to the amount of rubber produced by a non-altered guayule. It is another object of this invention that the genetically altered guayule is exposed to a temperature between approximately 7° C. and approximately 15° C. for approximately 8 hours per day and/or exposed to salicylic acid and/or exposed to PaAos dsRNA which results in a synergistic increase in the amount of rubber produced by the genetically altered guayule. Another object of this invention is to have a genetically altered guayule made using these methods and the progeny thereof. It is a further object of this invention to have germplasm, pollen, flowers, seeds, stems, leaves, roots, cells, etc., of these genetically altered guayule.

It is an object of this invention to have a method for increasing the amount of rubber produced by an altered guayule compared to the amount of rubber produced by a non-altered guayule. It is another object of this invention that the alteration induces RNAi to silence PaAos expression which is generated by transforming a non-altered guayule cell with an expression vector containing a heterologous promoter operably linked to a polynucleotide encoding PaAos anti-sense RNA. The polynucleotide can also encode a sequence complementary to PaAos anti-sense RNA sequence so that dsRNA is formed.

It is a further object of this invention to have a method for increasing the amount of rubber produced by an altered guayule compared to the amount of rubber produced by a non-altered guayule by administering salicylic acid (SA) and/or a PaAos dsRNA solution to a non-altered guayule to produce an altered guayule. The SA and/or PaAos dsRNA enter the altered guayule and cause the altered guayule to produce an increased amount of rubber compared to the amount of rubber produced by the non-altered guayule. It is another object of this invention that the PaAos dsRNA has a sequence of at least 19 contiguous nucleotides of the sequence of PaAos, at least 19 contiguous nucleotides of the reverse complementary sequence of PaAos, SEQ ID NO: 11 (or a sequence at least 95% identical thereof), and/or at least 19 contiguous nucleotides of SEQ ID NO: 11; or SEQ ID NO: 45. It is another object of this invention that an SA solution can have a concentration between approximately 0.1 nM to approximately 100 nM of SA. It is another object of this invention that the SA and/or PaAos dsRNA solution is administered to the plant by (i) spraying onto the plant, (ii) applying to soil surrounding the plant, (iii) applying to a root of plant and/or (iv) applying to irrigation water which is applied to soil surrounding the plant. It is another object of this invention that one can optionally expose the altered guayule to a temperature between approximately 7° C. and approximately 15° C. for approximately 8 hours per day which results in a synergistic increase in the amount of rubber produced by the altered guayule compared to a non-altered guayule exposed to the same temperatures.

BRIEF DESCRIPTION OF THE SEVERAL VIEWS OF THE DRAWINGS

FIG. 2 shows the primers used in the qRT-PCR, PCR reaction conditions, and the expected amplicon product size to determine RNA expression in the genetically altered guayule. Amplicon (mRNA product) $PaAos_{OE}$ is derived from plants transformed with pND6-Aos (Aos overexpression). Amplicon (mRNA product) $PaAos_{RNAi}$ is derived from plants transformed with pND6-AosiL (Aos silencing). Amplicon (mRNA product) 18S is from 18S ribosome RNA. Amplicon (mRNA product) PaAos is for wild-type guayule plants with intact PaAos gene.

FIG. 3 provides size and weight measurements of the four types of guayule plants grown under different conditions in growth chambers. Plants are initially transferred to soil from tissue culture media and grown under greenhouse conditions for one month. Following, plants are moved to controlled-temperature growth chamber conditions under 27° C. (16 h)/25° C. (8 h) and at 27° C. (16 h)/10° C. (8 h). The four type of guayule plants are wild-type (G7-11.1 and G7-11.2), guayule transformed with the empty expression vector pND6 (pND6-10, pND6-12, pND6-35), guayule transformed with pND6-AosiL for silencing PaAos via RNAi ($pND6-AosiL_{7-2}$, $pND6-AosiL_{8-1}$, $pND6-AosiL_{9-16}$, $pND6-AosiL_{12-1}$,), and guayule transformed with pND6-Aos to overexpress PaAos ($pND6-Aos_{4-1}$, $pND6-Aos_{4-2}$, $pND6-Aos_{5-1}$, $pND6-Aos_{7-1}$,) at 2 months old. G7-11 is a breeder's nomenclature for what later became the USDA publicly released guayule Germplasm line AZ-2 (Reg. No. GP-9; PI 599676). The biomass of the shoot (leaves plus stems) and root are weighed in 2 months old guayule plants grown in growth chambers under 27° C. (16 h)/25° C. (8 h) and at 27° C. (16 h)/10° C. (8 h). The asterisks, (*), () and (*), indicate significant difference in comparison to (non-altered) G7-11 at p>0.05, 0.005 and 0.0005, respectively.

FIG. 5 shows the number of branches and stem diameter of 2 months old genetically altered guayule (pND6-AosiL and pND6-Aos lines), non-altered guayule (G7-11) and empty vector control guayule (pND6) plants grown in growth chambers at 27° C. (16 h)/25° C. (8 h) or at 27° C. (16 h)/10° C. (8 h). pND6-AosiL genotypes have larger number of stems than the non-altered and empty vector controls. Additionally, the mature stembark tissues in pND6-AosiL have significantly thicker diameter (ranging from 35% to 54%) under both 27° C. (16 h)/25° C. (8 h) and 27° C. (16 h)/10° C. (8 h).

FIG. 9A, FIG. 9B, and FIG. 9C show single nucleotide polymorphisms (SNP) in PaAos coding sequence for guayule cultivars W6 549 ("W6549"; SEQ ID NO: 12), G7-11 (SEQ ID NO: 9), and PI 478652 ("478652"; SEQ ID NO: 14). The SNPs are contained in boxes.

FIG. 10 shows an alignment of PaAos amino acid sequences obtained from guayule cultivars W6 549 ("W6549"; SEQ ID NO: 13), PI 478652 ("478652"; SEQ ID NO: 15) and G7-11 (SEQ ID NO: 10). The boxes highlight the different amino acids against the cultivars.

FIG. 11A, FIG. 11B, and FIG. 11C provide PaAos promoter's sequence (SEQ ID NO: 26) and indicates sequences that are putative binding sites of the indicated transcription factors.

FIG. 12 provides the names and sequences of various primers, their annealing temperatures and amplicon size.

DETAILED DESCRIPTION OF THE INVENTION

Figure 1:
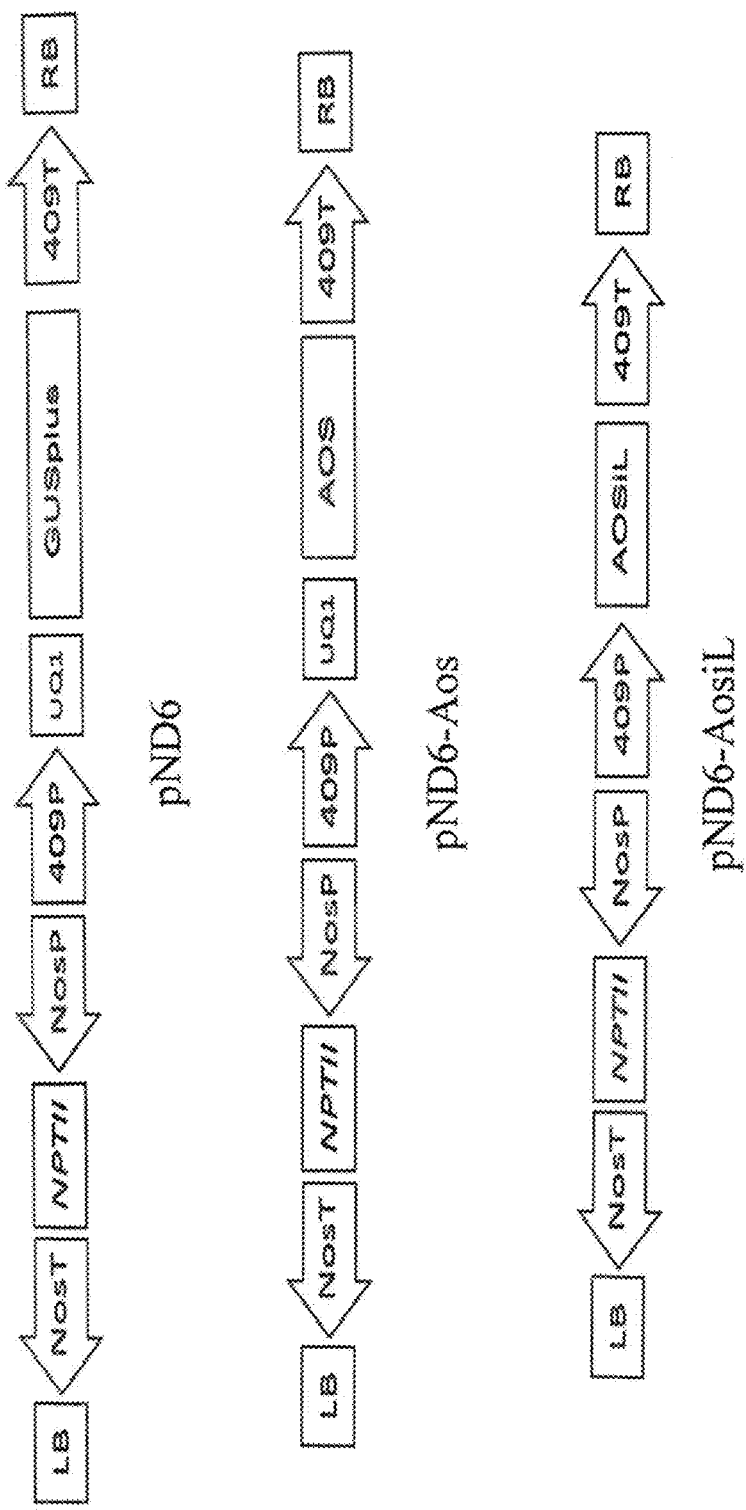
FIG. 1 shows the design of the plasmids used in Example 1 for the overexpression of PaAos (pND6-Aos), silencing of PaAos (pND6-AosiL), and for the control plasmid (pND6). Each expression vector features the NPTII gene to confer kanamycin resistance for selection, and the control plasmid contains the GUS (β-glucuronidase) reporter gene instead of PaAos or a portion of PaAos in reverse complementary orientation. Thus, one can use a histochemical GUS staining assay (the chromogenic substrate X-Gluc ($C_{14}H_{13}BrClNO_7$)) as a visual indicator of transformed tissues with the negative control plasmid.

This invention involves a novel and unexpected method of increasing natural rubber yield in guayule plants by manipulating the expression of PaAos and/or reducing the amount of functional PaAos and/or reducing PaAos' functionality present in guayule. By altering the expression of PaAos and/or reducing the amount of functional PaAos and/or reducing PaAos' functionality, one also reduces the amount of functional PaAos in rubber particles. The rubber yield per acre is increased because the genetically altered guayule is also larger than non-altered guayule and has more tissue in which to store rubber. Genetically altered guayule that express the reverse complement of PaAos have reduced amounts of PaAos in the rubber particles via RNAi. Because these genetically altered guayule plants produce less PaAos, they also have altered amounts of various hormones that are produced in the biosynthetic pathway for which PaAos is one enzyme. In particular, the amount of jasmonic acid, abscisic acid, gibberellin $A_{20}$, gibberellin $A_1$, and gibberellin $A_3$ are decreased in the RNAi genetically altered guayule while the amount of salicylic acid (SA) is increased, compared to non-genetically altered guayule. Using RNAi technology to reduce the amount of PaAos in the plant, these genetically altered guayule unexpectedly and surprisingly have increased amount of rubber compared to non-altered guayule plants AND more biomass which increases the rubber yield. One optionally exposes the genetically altered guayule to cold temperature (between approximately 7° C. and approximately 15° C. or between approximately 10° C. and approximately 15° C.; approximately 8 hours per day) which, surprisingly and unexpectedly, acts synergistically with the reduced PaAos transcription (and/or reduced amount of functional PaAos) to increase the amount of rubber production even greater than to the amount produced by non-altered guayule. Methods of enhancing rubber yield via suppression of PaAos expression via RNAi and similar technologies, and markers for the identification of such guayule with altered PaAos are provided. For the purposes of this invention, the terms "function", "functional", and "functionality" include any activity that the protein or other compound possesses. A protein/compound may have enzymatic activity, binding activity, transporting activity, structural activity, etc.

As mentioned above, one embodiment of this invention involves using RNAi to reduce production of PaAos which causes an increase in rubber production and biomass of the genetically altered guayule. In another embodiment, the invention involves altering the genomic PaAos sequence such that no functional PaAos is produced (a "null" mutation), or that the encoded protein has reduced functionality compared to the activity of non-modified PaAos. When no functional PaAos is produced or when PaAos with reduced functionality is produced, then it is understood that the altered guayule produces "a reduced amount of functional PaAos". Such altered guayule producing a reduced amount of functional PaAos is another embodiment of this invention. In yet another embodiment, the invention involves increasing the amount of SA in guayule which results in increased amount of rubber being produced compared to the amount of rubber produced in guayule which does not have increased amount of SA. One embodiment involves administering an effective amount of SA to a non-altered guayule, which causes the treated guayule to reduce PaAos expression and/or reduce the amount of functional PaAos, and thus increases the amount of rubber produced by the treated guayule compared to the amount of rubber produced by a non-altered guayule.

Another embodiment of this invention involves an altered guayule producing more rubber than the amount of rubber produced by a non-altered guayule. In one embodiment, the altered guayule overexpresses one or more transcription factors (PaWRKY3-like, PaWRKY71-like, and/or PaMYBS3-like) using an expression vector that contains a heterologous promoter operably linked to the coding sequences of one or more of these transcription factors (SEQ ID NOs: 39 and 40, 41 and 42, and/or 43 and 44, or a sequence at least 95% identical thereof for PaWRKY3-like, PaWRKY71-like, and/or PaMYBS3-like, respectively). In another embodiment, the altered guayule contains an expression vector that produces PaAos dsRNA or anti-sense RNA so that less amount of PaAos is produced by the altered guayule. In another embodiment, the altered guayule contains a mutated PaAos and the altered guayule produces PaAos with reduced or no functionality, compared to the functionality of PaAos in a non-altered guayule. In yet another embodiment, any of these genetic alterations are present in the guayule. In yet another embodiment, one optionally subjects any of the altered guayule to cold temperatures and/or administers SA to the altered guayule and/or administers dsRNA for PaAos to the altered guayule to increase rubber production in the altered guayule compared to the amount of rubber produced by a non-altered guayule.

Because this invention involves production of genetically altered plants and involves recombinant DNA techniques, the following definitions are provided to assist in describing this invention. The terms "isolated", "purified", or "biologically pure" as used herein, refer to material that is substantially or essentially free from components that normally accompany the material in its native state or when the material is produced. In an exemplary embodiment, purity and homogeneity are determined using analytical chemistry techniques such as polyacrylamide gel electrophoresis or high performance liquid chromatography. A nucleic acid or particular bacteria that are the predominant species present in a preparation is substantially purified. In an exemplary embodiment, the term "purified" denotes that a nucleic acid or protein that gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "gene" refers to a DNA sequence involved in producing a RNA or polypeptide or precursor thereof. The polypeptide or RNA is encoded by a full-length coding sequence (cds) or by intron-interrupted portions of the coding sequence, such as exon sequences. In one embodiment of this invention, the gene involved is *Parthenium argentatum* allene oxide synthase (PaAos or Aos). PaAos cDNA and amino acid sequence is found in GenBank accession number X78166.2 which is cultivar G7-11 (wild-type/non-altered) (USDA publicly released guayule Germplasm line AZ-2 (Reg. No. GP-9; PI 599676)). The cDNA sequence is in SEQ ID NO: 9; the protein sequence is in SEQ ID NO: 10. SEQ ID NO: 12 is the cDNA sequence for PaAos and SEQ ID NO: 13 is the amino acid sequence for PaAos in guayule W6549 cultivar. SEQ ID NO: 14 is the cDNA sequence for PaAos and SEQ ID NO: 15 is the amino acid sequence for PaAos in guayule 478652 cultivar. In one embodiment, the reverse complementary sequence of PaAos (negative strand) (or a sequence that is at least 95% identical) is operably linked to a heterologous promoter to produce RNA have a complementary sequence to the mRNA made from PaAos (SEQ ID NOs: 9, 12, or 14 or the sequence present any other cultivar) (positive strand). In one embodiment, one uses the sequence in SEQ ID NO: 11 (or a sequence that is at least 95% identical) as a portion of the reverse complement polynucleotide of PaAos, or use SEQ ID NO: 45. In another embodiment, DNA encoding one or more of the transcription factors PaWRKY3-like (SEQ ID NOs: 39 and 40 or a sequence at least 95% identical thereof), PaWRKY71-like (SEQ ID NOs: 41 and 42 or a sequence at least 95% identical thereof), and PaMYBS3-like (SEQ ID NOs: 43 and 43 or a sequence at least 95% identical thereof) are overexpressed in an altered guayule.

le;.5qThe term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, peptide-nucleic acids (PNAs). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein.

For nucleic acids, sizes are given in either kilobases (kb) or base pairs (bp), or nucleotides (nt). Estimates are typically derived from agarose or acrylamide gel electrophoresis, from sequenced nucleic acids, or from published DNA sequences. For proteins, sizes are given in kiloDaltons (kDa) or amino acid residue numbers. Proteins sizes are estimated from gel electrophoresis, from sequenced proteins, from derived amino acid sequences, or from published protein sequences.

Unless otherwise indicated, a particular nucleic acid sequence for each amino acid substitution (alteration) also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98(1994)). Because of the degeneracy of nucleic acid codons, one can use various different polynucleotides to encode identical polypeptides. Table 1, infra, contains information about which nucleic acid codons encode which amino acids and is useful for determining the possible nucleotide substitutions that are included in this invention.

TABLE 1

| Amino acid | Nucleic acid codons | Amino acid | Nucleic acid codons |
|---|---|---|---|
| Ala/A | GCT, GCC, GCA, GCG | Leu/L | TTA, TTG, CTT, CTC, CTA, CTG |
| Arg/R | CGT, CGC, CGA, CGG, AGA, AGG | Lys/K | AAA, AAG |

TABLE 1-continued

| Amino acid | Nucleic acid codons | Amino acid | Nucleic acid codons |
|---|---|---|---|
| Asn/N | AAT, AAC | Met/M | ATG |
| Asp/D | GAT, GAC | Phe/F | TTT, TTC |
| Cys/C | TGT, TGC | Pro/P | CCT, CCC, CCA, CCG |
| Gln/Q | CAA, CAG | Ser/S | TCT, TCC, TCA, TCG, AGT, AGC |
| Glu/E | GAA, GAG | Thr/T | ACT, ACC, ACA, ACG |
| Gly/G | GGT, GGC, GGA, GGG | Trp/W | TGG |
| His/H | CAT, CAC | Tyr/Y | TAT, TAC |
| Ile/I | ATT, ATC, ATA | Val/V | GTT, GTC, GTA, GTG |
| Stop | TAA, TGA, TAG | | |

In addition to the degenerate nature of the nucleotide codons which encode amino acids, alterations in a polynucleotide that result in the production of a chemically equivalent amino acid at a given site, but do not affect the functional properties of the encoded polypeptide, are well known in the art. "Conservative amino acid substitutions" are those substitutions that are predicted to interfere least with the properties of the reference polypeptide. In other words, conservative amino acid substitutions substantially conserve the structure and the function of the reference protein. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine or histidine, is also expected to produce a functionally equivalent protein or polypeptide. Table 2 provides a list of exemplary conservative amino acid substitutions. Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain. In another embodiment, groups of amino acids that are conservative substitutions for each other are (i) alanine (Ala or A), serine (Ser or S), and threonine (Thr or T); (ii) aspartic acid (Asp or D) and glutamic acid (Glu or E); (iii) asparagine (Asn or N) and glutamine (Gln or Q); (iv) arginine (Arg or R) and lysine (Lys or K); (v) isoleucine (Ile or I), leucine (Leu or L), methionine (Met or M), and valine (Val or V); and (vi) phenylalanine (Phe or F), tyrosine (Tyr or Y), and tryptophan (Trp or W). See, Creighton, Proteins, W.H. Freeman and Co. (1984), contents of which are expressly incorporated herein. In yet another embodiment, amino acid(s) that are conservative substitutes for one amino acid are grouped by the following characteristics: aliphatic amino acids (alanine, glycine, isoleucine, leucine, and valine); hydroxyl or sulfur containing amino acids (cysteine, serine, methionine, and threonine); cyclic (proline); aromatic (phenylalanine, tryptophan, and tyrosine); basic (arginine, histidine, and lysine); acidic (aspartate and glutamate); and uncharged (asparagine and glutamine).

TABLE 2

| Amino Acid | Conservative Substitute |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Ile, Leu |
| Phe | His, Leu, Met, Trp, Tyr |
| Ser | Cys, Thr |
| Thr | Ser, Val |
| Trp | Phe, Tyr |
| Tyr | His, Phe, Trp |
| Val | Ile, Leu, Thr |

The term "primer" refers to an oligonucleotide which may act as a point of initiation of DNA extension. A primer may occur naturally, as in a purified restriction digest, or may be produced synthetically.

A primer is selected to be "substantially complementary" to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence is sufficiently complementary with the sequence of the template to hybridize and thereby form a template primer complex for synthesis of the extension product of the primer.

"dsRNA" refers to double-stranded RNA that contains a sense region and an antisense region of a selected target gene (or sequences with high sequence identity thereto so that gene silencing occurs), as well as any smaller double-stranded RNAs formed therefrom by RNAse or Dicer activity. Such dsRNA may include portions of single-stranded RNA, but contains at least 18 base pairs of dsRNA. A dsRNA after been processed by Dicer generates siRNAs (18-25 bp in length) that are double-strand, and could contain ends with 2 nucleotide overhangs, which will be single-stranded. It is predicted that usually siRNA around 19 nt in length (or, alternatively, between 17 and 27 nt in length), will be incorporated into RISC. In one embodiment, the sense region and the antisense region of a dsRNA are on the same strand of RNA and are separated by a linker. In this embodiment, when the sense region and the antisense region anneal together, the dsRNA contains a loop which is the linker. One promoter operably linked to the DNA or RNA encoding both the sense region and the antisense region is used to produce the one RNA molecule containing both the sense region and the anti-sense region. In another embodiment, the sense region and the antisense region are present on two distinct strands of RNA (a sense strand and the anti-sense strand which is complementary to the sense strand) which anneal together to form the dsRNA. In this embodiment, a promoter is operably linked to each strand of DNA or RNA; where one DNA or RNA strand encodes the RNA containing the sense region and the other strand of DNA or RNA encodes the RNA containing the anti-sense region. In this embodiment, the promoter on each strand may be the same as or different from the promoter on the other strand. After the RNAs are transcribed, two RNA strands anneal together because the sense region and the anti-sense region are complementary to each other, thus forming the dsRNA. In yet another embodiment, one strand of DNA or RNA can encode both the sense region and the anti-sense region of the dsRNA. However, the DNA or RNA coding each region are separated from each other so that two promoters are necessary to transcribe each region. That is, the DNA or RNA encoding the anti-sense region and the DNA or RNA encoding the sense region are operably linked to their own promoter. Again, the two promoters may be the same promoter or different promoters. In one embodiment, the promoter can be a T7 RNA polymerase promoter. Other promoters are well-known in the art and can be used (see discussion infra). While many embodiments of this invention use DNA to encode the sense region and/or anti-sense region, as described infra, it is possible to use a recombinant RNA virus to produce the dsRNA described herein. In such cases, a virus has had its genome altered so that the infected cell produces one of the sequences of PaAos described herein or the reverse complement thereof or both.

Active dsRNA molecules have worked when they were as long as 1,000 bp, and should work when even longer. For the purposes of the inventions described herein, any siRNA having at least 19 nt length derived from PaAos, or the reverse complement sequence thereof and that are specific to PaAos. In one embodiment, the dsRNA may be any 16, 17, 18, 19, 20, 21, 22, 23, 24, 25, 26, 27, 28, 29, 30, 31, 32, 33, 34, 35, 36, 37, 38, 39, 40, 45, 50, 55, 60, or longer contiguous nucleotides, up and including the full-length of PaAos cDNA (SEQ ID NOs: 9, 12, and/or 14 or a sequence at least 95% identity thereof or the sequence of any other PaAos). In another embodiment, the reverse complement sequence of PaAos is SEQ ID NO: 11 or a sequence at least 95% identity thereof, or SEQ ID NO: 45. In alternative embodiments, the dsRNA ranges in length between 16 bp and 30 bp, between 16 bp and 25 bp, between 18 and 30 bp, and between 19 bp and 28 bp. In yet another embodiment, RNA forms that are created by RNAse III family (Dicer or Dicer-like ribonuclease) or Dicer activity that are longer dsRNA are within the scope of this invention.

One uses computer programs to predict dsRNA sequences that will be effective in reducing production of the desired gene/protein (in this embodiment PaAos and PaAos). Information about such computer programs are be found on the following two websites: genelink.com/siRNA/RNAiwhati-s.asp; and rnaiweb.com/RNAi/RNAi_Web_Resources/RNAi_Tools_Software/Online_siRNA_Design_Tools/index.html. Using such computer programs, one can obtain sequences that differ from SEQ ID NO: 11 which can be used to generate dsRNA via binding to PaAos mRNA. Alternatively, one can determine an appropriate sequence to test using the methodologies described in Preuss, S. and Pikaard, C. S. (2003) Targeted gene silencing in plants using *RNA interference, in RNA interference (RNAi)~Nuts and Bolts of siRNA Technology* (Engelke, D., Ed.), pp 23-36, DNA Press, LLC.

siRNA may be synthetically made, expressed and secreted directly from a transformed cell, or microbe, or generated from a longer dsRNA by enzymatic activity. These siRNAs may be blunt-ended or have 1 bp to 4 bp overlapping ends of various nucleotide combinations. Also modified microRNAs comprising a portion of PaAos and its reverse complementary sequence are included herein as dsRNAs. In one embodiment of the invention, the dsRNA is expressed in a plant to be protected, or expressed in microorganisms which can be endemic organisms of the plant (microbes, virus, phytoplasma, viroids, fungal, protists) or free-living microbes (yeasts, bacteria, protists, fungi) any of which are delivered, alive, dead or processed, via root treatments, or foliar sprayed on plants, or injected into plants, which are to be protected. Alternatively, the microorganism can be a transgenic organism endemic to the plant and deliver dsRNA to the plant. See, e.g., Subhas, et al. (2014) *J. Biotech.* 176:42-49 for an example of virus induced gene silencing using *Citrus tristeza* virus. See, also, Tenllado, et al. (2003) *BMC Biotechnol* 3:3 for an example of a crude extract of a bacterial cell culture containing dsRNA that protects plants against viral infections.

In one embodiment, a dsRNA solution is administered to the guayule plant. A dsRNA solution contains one or more of the dsRNAs discussed herein and an agriculturally acceptable carrier. An agriculturally acceptable carrier can be water, one or more liposomes, one or more lipids, one or more surfactants, one or more proteins, one or more peptides, one or more nanotubes, chitin, and/or one or more inactivated microorganisms that encapsulate the dsRNA. See WO 2003/004644 for examples of other agriculturally acceptable carriers, contents of which are expressly incorporated herein. The dsRNA solution may also contain one or more sugars, compounds that assist in preventing dsRNA degradation, translaminar chemicals, chemical brighteners, clays, minerals, and/or fertilizers. One can spray the dsRNA solution on plants (leaves, branches, trunk, exposed roots, etc.). One can apply the dsRNA solution to the soil around the plant so that the plant's roots absorb the dsRNA solution and transport it to other parts of the plants. Alternatively, one or more roots can be placed in a container which contains the dsRNA solution so that those roots absorb the dsRNA solution. The dsRNA solution can also be injected into the plant. As such, the dsRNA solution may be in a spray dsRNA solution, a drenching dsRNA solution, or an injectable dsRNA solution. The dsRNA may also be mixed into irrigation water which is then administered to the plants. The plant's roots will absorb the dsRNA in the irrigation water, resulting in RNAi. Other types of solutions are known in the art.

In another embodiment, one administers dsRNA and salicylic acid to a non-altered guayule or to a guayule with a genetic alteration (such as overexpressing one or more of the transcription factors PaWRKY3-like, PaWRKY71-like, and/or PaMYBS3-like) to increase rubber production which would yield more rubber than the amount of rubber produced by a non-altered guayule, under the same conditions. The dsRNA and salicylic acid are administered concurrently or sequentially. They can be administered via irrigation water, by administering the dsRNA and/or salicylic acid to the soil around the plant, by placing a root of the plant into a container holding the dsRNA and/or salicylic acid, spraying the dsRNA and/or salicylic acid onto the plant, or a combination thereof. For example, the dsRNA could be sprayed onto the plant while the salicylic acid is added to the irrigation water and applied to the soil around the plant. Root drenching with dsRNA and/or salicylic acid is yet another embodiment. In yet another embodiment, one administers the dsRNA and salicylic acid to the plant prior to or when the temperature is cold (between approximately 7° C. and approximately 15° C. or between approximately 10° C. and approximately 15° C.; for approximately 8 hours per day). The treated guayule will produce more rubber than the amount of rubber produced by the untreated guayule.

Oligonucleotides and polynucleotides that are not commercially available can be chemically synthesized e.g., according to the solid phase phosphoramidite triester method first described by Beaucage and Caruthers, *Tetrahedron Letts.* 22:1859-1862 (1981), or using an automated synthesizer, as described in Van Devanter et al., *Nucleic Acids Res.* 12:6159-6168 (1984). Other methods for synthesizing oligonucleotides and polynucleotides are known in the art. Purification of oligonucleotides is by either native acrylamide gel electrophoresis or by anion-exchange HPLC as described in Pearson & Reanier, *J. Chrom.* 255:137-149 (1983).

The terms "identical" or percent "identity", in the context of two or more polynucleotides or polypeptide sequences, refer to two or more sequences or sub-sequences that are the same or have a specified percentage of nucleotides or amino acids (respectively) that are the same (e.g., 80%, 85% identity, 90% identity, 99%, or 100% identity), when compared and aligned for maximum correspondence over a designated region as measured using a sequence comparison algorithm or by manual alignment and visual inspection.

The phrase "high percent identical" or "high percent identity", in the context of two polynucleotides or polypeptides, refers to two or more sequences or sub-sequences that have at least about 80%, identity, at least about 81%, 82%, 83%, 84%, 85%, 86%, 87%, 88%, 89%, 90%, 91%, 92%, 93%, 94%, 95%, 96%, 97%, 98%, 99%, or 100% nucleotide or amino acid identity, when compared and aligned for maximum correspondence, as measured using a sequence comparison algorithm or by visual inspection. In an exemplary embodiment, a high percent identity exists over a region of the sequences that is at least about 16 nucleotides or amino acids in length. In another exemplary embodiment, a high percent identity exists over a region of the sequences that is at least about 50 nucleotides or amino acids in length. In still another exemplary embodiment, a high percent identity exists over a region of the sequences that is at least about 100 nucleotides or amino acids or more in length. In one exemplary embodiment, the sequences are high percent identical over the entire length of the polynucleotide or polypeptide sequences.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters may be used, or alternative parameters designated. The sequence comparison algorithm then calculates the percent sequence identities for the test sequences relative to the reference sequence, based on the program parameters. Methods of alignment of sequences for comparison are well-known in the art. Optimal alignment of sequences for comparison is conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of various algorithms (GAP, BESTFIT, FASTA, and TFASTA in the Wisconsin Genetics Software Package, Genetics Computer Group, 575 Science Dr., Madison, Wis.), and/or by manual alignment and visual inspection (see, e.g., Ausubel et al. (eds.), *Current Protocols in Molecular Biology,* 1995 supplement).

The "complement" of a particular polynucleotide sequence is that nucleotide sequence which would be capable of forming a double-stranded DNA or RNA molecule with the represented nucleotide sequence, and which is derived from the represented nucleotide sequence by replacing the nucleotides by their complementary nucleotide according to Chargaff's rules (A< >T; G< >C) and reading in the 5' to 3' direction, i.e., in opposite direction of the represented nucleotide sequence (reverse complement).

In one embodiment of the invention, sense and antisense RNAs and dsRNA can be separately expressed in-vitro or in-vivo. In-vivo production of sense and antisense RNAs may use different chimeric polynucleotide constructs using the same or different promoters or using an expression vector containing two convergent promoters in opposite orientation. The sense and antisense RNAs which are formed (e.g., in the same host cells or synthesized) then combine to form dsRNA. To be clear, whenever reference is made herein to a dsRNA chimeric or fusion polynucleotide or a dsRNA molecule, that such dsRNA formed (e.g., in plant cells) from sense and antisense RNA produced separately is also included. Also, synthetically made dsRNA and self-annealing RNA strands are included herein when the sense and antisense strands are present together.

As used herein, the term "promoter" refers to a polynucleotide that, in its native state, is located upstream or 5' to a translational start codon of an open reading frame (or protein-coding region) and that is involved in recognition and binding of RNA polymerase and other proteins (transacting transcription factors) to initiate transcription. A "plant promoter" is a native or non-native promoter that is functional in plant cells, even if the promoter is present in a microorganism that infects plants or a microorganism that does not infect plants. The promoters that are predominately functional in a specific tissue or set of tissues are considered "tissue-specific promoters". A plant promoter can be used as a 5' regulatory element for modulating expression of a particularly desired polynucleotide (heterologous polynucleotide) operably linked thereto. When operably linked to a transcribable polynucleotide, a promoter typically causes the transcribable polynucleotide to be transcribed in a manner that is similar to that of which the promoter is normally associated.

Plant promoters include promoters produced through the manipulation of known promoters to produce artificial, chimeric, or hybrid promoters. Such promoters can also combine cis-elements from one or more promoters, for example, by adding a heterologous regulatory element to an active promoter with its own partial or complete regulatory elements. The term "cis-element" refers to a cis-acting transcriptional regulatory element that confers an aspect of the overall control of gene expression. A cis-element may function to bind transcription factors, trans-acting protein factors that regulate transcription. Some cis-elements bind more than one transcription factor, and transcription factors may interact with different affinities with more than one cis-element.

The term "vector" refers to DNA, RNA, a protein, or polypeptide that are to be introduced into a host cell or organism. The polynucleotides, protein, and polypeptide which are to be introduced into a host may be therapeutic or prophylactic in nature; may encode or be an antigen; may be regulatory in nature; etc. There are various types of vectors including viruses, viroids, plasmids, bacteriophages, cosmids, and bacteria.

An expression vector is nucleic acid capable of replicating in a selected host cell or organism. An expression vector can replicate as an autonomous structure, or alternatively integrate, in whole or in part, into the host cell chromosomes or the nucleic acids of an organelle, or it is used as a shuttle for delivering foreign DNA to cells, and thus replicate along with the host cell genome. Thus, an expression vector are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an "expression cassette". In contrast, as described in the examples herein, a "cassette" is a polynucleotide containing a section of an expression vector. The use of the cassettes assists in the assembly of the expression vectors. An expression vector is a replicon, such as plasmid, phage, virus, chimeric virus, or cosmid, and which contains the desired polynucleotide sequence operably linked to the expression control sequence (s).

A heterologous polynucleotide sequence is operably linked to one or more transcription regulatory elements (e.g., promoter, terminator and, optionally, enhancer) such that the transcription regulatory elements control and regulate the transcription and/or translation of that heterologous polynucleotide sequence. A cassette has the heterologous polynucleotide operably linked to one or more transcription regulatory elements. As used herein, the term "operably linked" refers to a first polynucleotide, such as a promoter, connected with a second transcribable polynucleotide, such as a gene of interest, where the polynucleotides are arranged such that the first polynucleotide affects the transcription of the second polynucleotide. In some embodiments, the two polynucleotide molecules are part of a single contiguous polynucleotide. In other embodiments, the two polynucleotides are adjacent. For example, a promoter is operably linked to a gene of interest if the promoter regulates or mediates transcription of the gene of interest in a cell. Similarly, a terminator is operably linked to the polynucleotide of interest if the terminator regulates or mediates transcription of the polynucleotide of interest, and, in particular, the termination of transcription. Constructs of the present invention would typically contain a promoter operably linked to a transcribable polynucleotide operably linked to a terminator.

The term "recombinant" when used with reference, e.g., to a cell, or nucleic acid, protein, or vector, indicates that the cell, organism, nucleic acid, protein or vector, has been altered by the introduction of a heterologous nucleic acid or protein or the alteration of a native nucleic acid or protein, or that the cell is derived from a cell so altered. Thus, for example, recombinant cells may express genes/polynucleotides that are not found within the native (non-recombinant or non-altered or wild-type) form of the cell or express native genes in an otherwise abnormal amount—over-expressed, under-expressed or not expressed at all—compared to the non-altered cell or organism. In particular, one alters the genomic DNA of a non-altered plant by molecular biology techniques that are well-known to one of ordinary skill in the art and generate a recombinant plant.

The terms "transgenic", "transformed", "transformation", and "transfection" are similar in meaning to "recombinant" "Transformation", "transgenic", and "transfection" refer to the transfer of a polynucleotide into a host organism or into a cell. Such a transfer of polynucleotides may result in genetically stable inheritance of the polynucleotides or in the polynucleotides remaining extra-chromosomally (not integrated into the chromosome of the cell). Genetically stable inheritance may potentially require the transgenic organism or cell to be subjected for a period of time to one or more conditions which require the transcription of some or all of the transferred polynucleotide in order for the transgenic organism or cell to live and/or grow. Polynucleotides that are transformed into a cell but are not integrated into the host's chromosome remain as an expression vector within the cell. One may need to grow the cell under certain growth or environmental conditions in order for the expression vector to remain in the cell or the cell's progeny. Further, for expression to occur the organism or cell may need to be kept under certain conditions. Genetically altered organisms or cells containing the recombinant polynucleotide are referred to as "transgenic" or "transformed" organisms or cells or simply as "transformants", as well as recombinant organisms or cells.

A genetically altered organism is any organism with any changes to its genetic material involving the invention described herein, whether in the nucleus or cytoplasm (organelle). As such, a genetically altered organism may be a recombinant or transformed organism. A genetically altered organism may also be an organism that was subjected to one or more mutagens or the progeny of an organism that was subjected to one or more mutagens and has mutations in its DNA caused by the one or more mutagens, as compared to the wild-type organism (i.e., organism not subjected to the mutagens) or the non-altered organism (i.e., one that contains alterations that are not the subject matter of this invention). Also, an organism that has been bred to incorporate a mutation into its genetic material is a genetically altered organism.

The term "altered" means that a change occurred compared to the "non-altered" item. However, a "non-altered" item could contain changes that are induced by man, but those changes are not the subject matter of the inventions described herein. For example, a non-altered guayule contains none of the described genetic changes nor has been treated with any of the described external substance, but may contain pre-existing changes which are not part of this invention. An altered guayule (which also is a genetically altered guayule) may contain a non-native expression vector that produces dsRNA or anti-sense RNA involving PaAOS or another gene and/or produces one or more transcription factors described herein or another gene. An altered guayule is also one which has been treated with a substance, such as dsRNA or salicylic acid (SA). An altered guayule may also have both types of changes.

Transformation and generation of genetically altered monocotyledonous and dicotyledonous plant cells is well known in the art. See, e.g., Weising, et al., *Ann. Rev. Genet.* 22:421-477 (1988); U.S. Pat. No. 5,679,558; *Agrobacterium Protocols*, ed: Gartland, Humana Press Inc. (1995); and Wang, et al. *Acta Hort.* 461:401-408 (1998). A method to generate genetically altered guayule is described in U.S. Pat. No. 9,018,449 (Dong & Cornish) and in Dong, et al., *Plant Cell Reports* 25:26-34 (2006). A method to generate transplastomic guayule is provided in U.S. Patent Application Publication 2014/0325699, the contents of which are expressly incorporated herein. The choice of method varies with the type of plant to be transformed, the particular application, and/or the desired result. The appropriate transformation technique is readily chosen by the skilled practitioner.

A polynucleotide encoding PaAos (SEQ ID NOs: 9, 12 and/or 14), the reverse complement of PaAos, or a portion thereof (e.g., SEQ ID NO: 11), operably linked to one or two appropriate promoters, can be stably inserted in a conventional manner into the genome (cytoplasmic genome or nucleic genome) of a single plant cell, and the altered plant cell can be used in a conventional manner to produce a genetically altered plant that produces the dsRNA of this invention. In this regard, a disarmed Ti-plasmid, containing the polynucleotide of this invention, in *Agrobacterium tumefaciens* can be used to genetically alter the plant cell, and thereafter, a genetically altered plant can be regenerated from the genetically altered plant cell using the procedures described in the art, for example, in EP 0 116 718, EP 0 270 822, WO 84/02913 and EP 0 242 246. Plant regeneration from cultured protoplasts is described in Evans et al., *Protoplasts Isolation and Culture*, in *Handbook of Plant Cell Culture*, pp. 124-176, MacMillan Publishing Company, New York, 1983; and Binding, *Regeneration of Plants*, in *Plant Protoplasts*, pp. 21-73, CRC Press, Boca Raton, 1985. Regeneration can also be obtained from plant callus, explants, organs, or parts thereof. Such regeneration techniques are described generally in Klee, et al., *Ann. Rev. of Plant Phys.* 38:467-486 (1987). Similarly, a polynucleotide encoding PaWRKY3-like, PaWRKY71-like, and/or PaMYBS3-like (the genomic sequence or coding sequence) may be incorporated into altered guayule.

Preferred Ti-plasmid vectors each contain the polynucleotides described herein between the border sequences, or at least located to the left of the right border sequence, of the T-DNA of the Ti-plasmid. Of course, other types of vectors may be used to transform the plant cell, using procedures such as direct gene transfer (as described, for example in EP 0 233 247), pollen mediated transformation (as described, for example in EP 0 270 356, WO 85/01856, and U.S. Pat. No. 4,684,611), plant RNA virus-mediated transformation (as described, for example in EP 0 067 553 and U.S. Pat. No. 4,407,956), liposome-mediated transformation (as described, for example in U.S. Pat. No. 4,536,475), and other methods such as the methods for transforming certain lines of corn (e.g., U.S. Pat. No. 6,140,553; Fromm, et al., *Bio/Technology* 8:833-839 (1990); Gordon-Kamm, et al., *The Plant Cell* 2:603-618 (1990) and rice (Shimamoto, et al., *Nature* 338:274-276 (1989); Datta et al., *Bio/Technology* 8:736-740 (1990)) and the method for transforming monocots generally (WO 92/09696). For cotton transformation, the method described in WO 2000/71733 can be used. For soybean transformation, reference is made to methods known in the art, e.g., Hinchee, et al. (*Bio/Technology* 6:915 (1988)) and Christou, et al. (*Trends Biotechnology* 8:145 (1990)) or the method of WO 00/42207.

The resulting genetically altered plant can be used in a conventional plant breeding scheme to produce more genetically altered plants with the same characteristics or to introduce the polynucleotide into other varieties of the same or related plant species. Seeds, which are obtained from the genetically altered plants, contain the expression vector as a stable genomic insert. Altered plants include plants having or derived from root stocks of altered plants containing the expression vector. Hence, any non-altered grafted plant parts inserted on a genetically altered plant or plant part are included in the invention.

For a genetically altered plant that produces dsRNA, one constructs an expression vector or cassette (made from DNA) that encodes, at a minimum, a first promoter and the dsRNA sequence of interest such that the promoter sequence is 5' (upstream) to and operably linked to the dsRNA sequence. The expression vector or cassette may optionally contain a second promoter (same as or different from the first promoter) upstream and operably linked to the reverse complementary sequence of the dsRNA sequence such that two strands of RNA that are complementary to each other are produced. Alternatively, the expression vector or cassette can contain one promoter operably linked to both the dsRNA sequence (sense strand) in question and the complement or reverse complement of the dsRNA sequence (antisense strand) in question, such that the transcribed RNA bends on itself and the two desires sequences anneal. Alternatively, a second expression vector or cassette (made from DNA) may encode, at a minimum, a second promoter (same as or different from the promoter) operably linked to the reverse complementary sequence of the dsRNA such that two strands of complementary RNA are produced in the plant. The expression vector(s) or cassette(s) is/are inserted in a plant cell genome (nuclear or cytoplasmic). The promoter(s) used should be a promoter(s) that is/are active in a plant and is/are heterologous to PaAos (not normally driving the transcription of RNA of genomic PaAos). Of course, the expression vector or cassette may have other transcription regulatory elements, such as enhancers, terminators, etc.

Promoters (and more specifically, heterologous promoters for PaAos, the reverse complement of PaAos, and the transcription factors) that are active in plants are well-known in the field. Such promoters may be constitutive, inducible, and/or tissue-specific. Non-limiting examples of constitutive plant promoters include 35S promoters of the cauliflower mosaic virus (CaMV) (e.g., of isolates CM 1841 (Gardner, et al., *Nucleic Acids Research* 9:2871-2887 (1981)), CabbB-S (Franck, et al., *Cell* 21:285-294 (1980)) and CabbB-JI (Hull and Howell, *Virology* 86:482-493 (1987))), ubiquitin promoter (e.g., the maize ubiquitin promoter of Christensen, et al., *Plant Mol. Biol.* 18:675-689 (1992)), gos2 promoter (de Pater, et al., *The Plant J.* 2:834-844 (1992)), emu promoter (Last, et al., *Theor. Appl. Genet.* 81:581-588 (1990)), actin promoter (see, e.g., An, et al., *The Plant J.* 10:107 (1996)) and Zhang, et al., *The Plant Cell* 3:1155-1165 (1991)); Cassava vein mosaic virus promoters (see, e.g., WO 97/48819 and Verdaguer, et al., *Plant Mol. Biol.* 37:1055-1067 (1998)), the pPLEX series of promoters from Subterranean Clover Stunt Virus (WO 96/06932, particularly the S4 or S7 promoter), alcohol dehydrogenase promoter (e.g., pAdh1S (GenBank accession numbers X04049, X00581)), and the TR1' promoter and the TR2' promoter which drive the expression of the 1' and 2' genes, respectively, of the T-DNA (Velten, et al., *EMBO J.* 3:2723-2730 (1984)). Tissue-specific promoters are promoters that direct a greater level of transcriptional expression in some cells or tissues of the plant than in other cells or tissue. Non-limiting examples of tissue-specific promoters include the phosphoenolpyruvate carboxylase (PEP or PPC1) promoter (Pathirana, et al., *Plant J.* 12:293-304 (1997), and Kausch, et al., *Plant Mol. Biol.* 45(1):1-15 (2001)), chlorophyll A/B binding protein (CAB) promoter (Bansal, et al., *Proc. Natl. Acad. Sci. USA* 89(8):3654-8 (1992)), small subunit of ribulose-1,5-bisphosphate carboxylase (ssRBCS) promoter (Bansal, et al., *Proc. Natl. Acad. Sci. USA* 89(8): 3654-8 (1992)), senescence activated promoter (SEE1) (Robson, et al., *Plant Biotechnol. J.* 2(2):101-12 (2004)), and sorghum leaf primoridia specific promoter (RS2) (GenBank Accession No. EI979305.1). These promoters (PPC1, CAB, ssRBCS, SSE1, and RS2) are all active in the aerial part of a plant. Further, the PPC1 promoter is a strong promoter for expression in vascular tissue. Some examples of phloem specific promoters are the sucrose synthase-1 promoters (CsSUS1p and CsSUS1p-2) (Singer et al., *Planta* 234:623-637 (2011)) and the phloem protein-2 promoter (CsPP2) (Miyata et al., *Plant Cell Report* 31(11):2005-2013 (2012)) from *Citrus sinensis*. Alternatively, a plant-expressible promoter may also be a wound-inducible promoter, such as the promoter of the pea cell wall invertase gene (Zhang, et al., *Plant Physiol.* 112:1111-1117 (1996)).

Other types of RNA polymerase promoters that may be used are promoters from microorganisms, such as, but not limited to the bacteriophage T7 RNA polymerase promoter, yeast Galactose (GAL1) promoter, yeast glyceraldehyde-3-phosphate dehydrogenase (GAP) promoter, yeast Alcohol Oxidase (AOX) promoter.

Other elements used to increase transcription expression in plant cells include, but are not limited to, an intron (e.g., hsp70 intron) at the 5' end or 3' end of the chimeric gene, or in the coding sequence of the chimeric dsRNA gene (such as, between the region encoding the sense and antisense portion of the dsRNA), promoter enhancer elements, duplicated or triplicated promoter regions, 5' leader sequences different from the chimeric gene or different from an endogenous (plant host) gene leader sequence, 3' untranslated sequences different from the chimeric gene or different from an endogenous (plant host) 3' untranslated sequence.

The expression vector or cassette could contain suitable 3' untranslated transcription regulation sequences (i.e., transcript formation and polyadenylation sequences). Potential polyadenylation and transcript formation sequences include those sequences in the nopaline synthase gene (Depicker, et al., *J. Molec. Appl. Genetics* 1:561-573 (1982)), the octopine synthase gene (Gielen, et al., *EMBO J.* 3:835-845 (1984)), the SCSV or the Malic enzyme terminators (Schunmann, et al., *Plant Functional Biology* 30:453-460 (2003)), and the T-DNA gene 7 (Velten and Schell, *Nucleic Acids Research* 13:6981-6998 (1985)).

The term "plant" includes whole plants, plant organs, progeny of whole plants or plant organs, embryos, somatic embryos, embryo-like structures, protocorms, protocorm-like bodies (PLBs), and suspensions of plant cells. Plant organs comprise, e.g., shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like). The class of plants that can be used in the method of the invention is generally as broad as the class of higher and lower plants amenable to the molecular biology and plant breeding techniques described herein, specifically angiosperms (monocotyledonous (monocots) and dicotyledonous (dicots) plants). It includes plants of a variety of ploidy levels, including aneuploid, polyploid, diploid, haploid and hemizygous. The genetically altered plants described herein are guayule plants.

Rubber yield may be expressed as a product of rubber content (% rubber) and biomass (dry weight/unit area). Thus, rubber yield may be improved by increasing either biomass and/or rubber content. The altered guayule described herein produce more rubber and have higher rubber content than non-altered guayule, thereby increasing the processing efficiency of the altered guayule shrub.

Because changes in PaAos functionality changes the amount of rubber produced by guayule, this invention also involves increasing a guayule's rubber production by reducing the amount of functional PaAos present in the genetically altered guayule (compared to the amount of functional PaAos present in non-altered guayule). In one embodiment, the genetically altered guayule has a mutation in PaAos, such as, a null mutation which results in (i) no protein is produced, (ii) a truncated protein is produced which has no functionality, or (iii) a full-length protein is produced which has no functionality. Other mutations simply reduce the functionality (activity) of PaAos. Non-limiting examples of mutations that reduce or eliminate PaAos functionality include (i) changing a codon encoding an amino acid to a stop codon (see Table 1 supra for the sequence of stop codons), (ii) changing the translation initiation codon (ATG) to any other codon to disrupt protein translation, (iii) changing a ribosome binding site's sequence to disrupt protein translation, (iv) changing one or more splice site codons to alter protein sequence, (v) deleting some or all of the gene's DNA sequence, (vi) inserting DNA into the gene, and (vii) changing one or more DNA codon sequences to encode non-conservative amino acids. Within SEQ ID NO: 9, nucleotides 34-36 encode ATG, the translation initiation codon for G7-11 guayule. Similarly, nucleotides 1-3 of SEQ ID NOs: 12 and 14 encode ATG, the translation initiation codon for cultivars PI 478652 and W6549, respectfully. Thus, a change in the nucleotide sequence of the equivalent codon in any other guayule would have the same result. Within PaAos, non-conservative amino acid substitutions at D318, S332, E336, R339, S359, I408, S411, and/or L459 (to name a few) result in PaAos with reduced functionality. One alters guayule DNA using the methods described herein and assesses changes in PaAos functionality via the methods described herein (e.g., assessing the amount of rubber produced by the altered guayule) or using methods known to one of ordinary skill in the art. One can utilize SNPs, antibodies, and other methods to identify the guayule that encode the altered amino acids.

Various methods exist to create a mutation. These methods are well-known to one of ordinary skill in the art. One method is by transforming the plant with a plasmid containing 5' sequence and 3' sequence of the gene and allowing a cross-over event to occur, thereby excising the DNA from the plant's genome that is between the plasmid's 5' sequence and 3' sequence. Also, one can use transposon-mediated mutation to delete or add DNA to PaAos which would result in the encoded protein having a reduced functionality compared to a non-altered PaAos. Two other methods involve using a chemical mutagen (such as ethyl methanesulfonate (EMS)) or physical agents (radiation, UV, or proton, for example) to generate genetic mutations in plant cells and/or germplasm. Also, one may use TALEN or CRISPR-Cas9 to mutate the sequence of the target gene (PaAos) such that a desired mutation is generated. One of ordinary skill in the art can also use targeted cleavage events to induce targeted mutagenesis, induce targeted deletions of cellular DNA sequences, and facilitate targeted recombination and integration at predetermined chromosomal locations to generate one or more of the null mutations discussed above or to reduce the mutated protein's functionality. Nucleotide editing techniques are well-known and described in Urnov, et al., *Nature* 435(7042):646-51 (2010); U. S. Patent Publications 2003/0232410, 2005/0208489, 2005/0026157, 2005/0064474, 2006/0188987, 2009/0263900, 2009/0117617, 2010/0047805, 2011/0207221, 2011/0301073, 2011/089775, 2011/0239315, and 2011/0145940; and International Publication WO 2007/014275, the disclosures of which are incorporated by reference in their entireties for all purposes. Cleavage occurs by using specific nucleases such as engineered zinc finger nucleases (ZFN), transcription-activator like effector nucleases (TALENs), or using the CRISPR/Cas9 system with an engineered crRNA/tracr RNA ('single guide RNA') to guide specific cleavage. U.S. Patent Publication 2008/0182332 describes the use of non-canonical zinc finger nucleases (ZFNs) for targeted modification of plant genomes; U.S. Patent Publication 2009/0205083 describes ZFN-mediated targeted modification of a plant EPSPS locus; U.S. Patent Publication 2010/0199389 describes targeted modification of a plant Zp15 locus and U.S. Patent Publication No. 20110167521 describes targeted modification of plant genes involved in fatty acid biosynthesis. In addition, Moehle, et al., *Proc. Natl. Acad. Sci. USA* 104(9):3055-3060 (2007) describes using designed ZFNs for targeted gene addition at a specified locus. U.S. Patent Publication 2011/0041195 describes methods of making homozygous diploid organisms. Information on CRISPR/Cas9 system is found, e.g., at en.wikipedia.org/wiki/CRISPR; neb.com/tools-and-resources/feature-articles/crispr-cas9-and-targeted-genome-editing-a-new-era-in-molecular-biology; and Cong, et al., *Science,* 339:819-823 (2013). Sigma-Aldrich (St. Louis, Mo.) and Origene Technologies, Inc. (Rockville, Md.) are among the companies that sell CRISPR/Cas9 kits.

After using any of these various methods to induce genetic alterations in a cell's genome, one induces the treated cells to grow into plants and then screen the plants using the methods described herein for PaAos having reduced or no functionality, and/or for reduced amounts of PaAos or no PaAos (via reduction in gene expression and/or mRNA translation and/or other mechanism), and/or for elevated production of rubber (compared to amounts present in non-altered plants). Thus, another embodiment of this invention is the generation of altered guayule having a genetic alteration in PaAos such that the altered guayule produces more rubber than produced by non-altered guayule.

Another embodiment of this invention is that one increases rubber production in guayule by increasing the amount of SA in altered guayule compared to the amount of SA present in untreated or non-altered guayule. One administers SA to guayule by spraying SA onto the guayule, drenching the soil around guayule with SA, adding SA to irrigation water which is then used to irrigate guayule. Another embodiment is to generate genetically altered guayule that produce an increased amount of SA than is produced by non-altered guayule by reducing the amount of functional PaAos in the genetically altered guayule. Such a reduction can be caused by a mutation in PaAos. The quantity (effective amount) of SA administered to the altered guayule being grown in tissue culture is the amount sufficient to generate a concentration in the tissue culture media ranging from approximately 0.1 nM to approximately 100 nM in one embodiment, from approximately 1 nM to approximately 100 nM solution in another embodiment, from approximately 5 nM to approximately 100 nM solution in another embodiment, and from approximately 10 nM to approximately 50 nM solution in another embodiment. For guayule plants in soil, from approximately 1 nM to approximately 100 nM SA solution in one embodiment, from approximately 5 nM to approximately 50 nM SA solution in another embodiment, or approximately 10 nM SA solution may be administered once, twice, or more per week. One can apply approximately 1 mL, approximately 10 mL, approximately 100 mL of the SA solution, depending on the SA concentration and the frequency of application. In one embodiment, 50 mL of 10 nM SA solution is applied twice weekly. To produce 10 nM SA solution, 0.0013812 mg SA is dissolved in 1 liter of 0.0000065% ethanol. To produce 100 nM SA solution, 0.013812 mg SA is dissolved in 1 liter of 0.0000065% ethanol. SA may be administered in a controlled release formulation, similar to children's liquid aspirin formulations or as a powder. SA can be administered early in a guayule plant's life (post-seedling stage which is approximately one month after germination of the seed), later in a guayule plant's life (several months prior to cut harvest), on a seasonal basis (during heat season, cold season, or both), or on a daily, weekly or monthly basis throughout the lifespan of the guayule plant. Administering SA to a guayule plant when exposed to cold temperatures (between approximately 7° C. and approximately 15° C. or between approximately 10° C. and approximately 15° C.; for approximately 8 hours per day), as occurs during the cold season, results in synergistically increase in rubber production. The term "administering SA to a guayule" and similar phrases means that exogenous SA is applied to the soil or plant or plant part.

Many techniques involving molecular biology discussed herein are well-known to one of ordinary skill in the art and are described in, e.g., Green and Sambrook, *Molecular Cloning, A Laboratory Manual* 4th ed. 2012, Cold Spring Harbor Laboratory; Ausubel et al. (eds.), *Current Protocols in Molecular Biology*, 1994—current, John Wiley & Sons; and Kriegler, *Gene Transfer and Expression: A Laboratory Manual* (1993). Unless otherwise noted, technical terms are used according to conventional usage. Definitions of common terms in molecular biology maybe found in e.g., Benjamin Lewin, *Genes IX*, Oxford University Press, 2007 (ISBN 0763740632); Krebs, et al. (eds.), *The Encyclopedia of Molecular Biology*, Blackwell Science Ltd., 1994 (ISBN 0-632-02182-9); and Robert A. Meyers (ed.), *Molecular Biology and Biotechnology: a Comprehensive Desk Reference*, VCH Publishers, Inc., 1995 (ISBN 1-56081-569-8).

The terms "approximately" and "about" refer to a quantity, level, value or amount that varies by as much as 30% in one embodiment, or in another embodiment by as much as 20%, and in a third embodiment by as much as 10% to a reference quantity, level, value or amount. As used herein, the singular form "a", "an", and "the" include plural references unless the context clearly dictates otherwise. For example, the term "a bacterium" includes both a single bacterium and a plurality of bacteria.

The term "nucleic acid consisting essentially of", "polynucleotide consisting essentially of", and "RNA consisting essentially of", and grammatical variations thereof, means a polynucleotide that differs from a reference nucleic acid sequence by 20 or fewer nucleotides and also perform the function of the reference polynucleotide sequence. Such variants include sequences which are shorter or longer than the reference nucleic acid sequence, have different residues at particular positions, or a combination thereof.

Having now generally described this invention, the same will be better understood by reference to certain specific examples and the accompanying drawings, which are included herein only to further illustrate the invention and are not intended to limit the scope of the invention as defined by the claims. The examples and drawings describe at least one, but not all embodiments, of the inventions claimed. Indeed, these inventions may be embodied in many different forms and should not be construed as limited to the embodiments set forth herein; rather, these embodiments are provided so that this disclosure will satisfy applicable legal requirements.

Example 1. Construction of Genetically Altered Guayule

To better understand the role of PaAos in rubber synthesis, genetically altered *P. argentatum* plants are generated in which either PaAos is over-expressed or PaAos is silenced by RNAi. The various plasmids used to achieve the over-expression or silencing of PaAos in guayule are shown in FIG. 1. To generate these plasmids, the guayule Aos (PaAos) is amplified by PCR using genomic DNA as a template. The primers used to amplify PaAos are designed from the cDNA PaAos sequence published in NCBI database (GeneBank accession no. X78166.2) and have the following sequences:

```
forward primer
                                              (SEQ ID NO: 1)
5'-cttaagaggtggtATGGACCCATCGTCTAAACCC-3'
and reverse primer
                                              (SEQ ID NO: 2)
5'-ggatccTCATATACTAGCTCTCTTCAGGG-3'.
```

The nucleotides in lower case and underlined in the forward primer are the recognition nucleotides for restriction enzyme AflII; the nucleotides in lower case and underlined in the reverse primer are the recognition nucleotides for restriction enzyme BamHI. The PCR cycle program is the following: 94° C. for 2 minutes (initial heating step) and PaAos is amplified at 40 cycles of 94° C. for 30 seconds (denaturation), 71° C. for 30 seconds (annealing) and 68° C. for 1 minute (extension) and an additional 5 minutes extension at 68° C. The resulting amplicon is purified and subcloned into pGEM T Easy vector (Promega, Madison, Wis.) using manufacturer's recommended protocol and sequenced to confirm the sequence of the plasmids. The cDNA sequence is in SEQ ID NO: 9 and the amino acid sequence is in SEQ ID NO: 10. Subsequently, the PaAos amplicon is cut using AflII and BamHI (Promega, Madison, Wis.). Plasmid pND6 has a Nos promoter driving the NPTII gene for conferring kanamycin resistance and a potato ubiquitin promoter (Garbarino and Belknap, *Plant Mol. Biol.* 24:119-127 (1994)) controlling the GUSplus gene (CambiaLabs, Canberra, Australia). See FIG. 1. Plasmid pND6-Aos (FIG. 1) is generated by replacing the GUSplus gene in pND6 with cDNA PaAos sequence (SEQ ID NO: 9). Plasmid pND6-AosiL (FIG. 1) is generated by replacing the GUSplus gene in pND6 with an inverted repeat of a partial cDNA PaAos sequence (SEQ ID NO: 11) containing a loop sequence of the Bar gene between the inverted repeat of the partial cDNA PaAos sequence; the complete sequence replacing GUSplus is SEQ ID NO: 45. The plasmids pND6, pND6-AosiL, and pND6-Aos are used to transform *Agrobacterium* EHA101 competent cells using the protocol described in Hood, et al., *J. Bacteriol.* 168: 1291-1301 (1986).

The transformed *Agrobacterium* EHA101 either harboring pND6, pND6-AosiL, or pND6-Aos are used to transform guayule G7-11 using the protocols set forth below. See also Dong, et al. (2006) and Dong, et al., *Industrial Crops and Products* 46:15-24 (2013). For *Agrobacterium* transformation, the overnight *Agrobacterium* culture are prepared by inoculating 50 µL glycerol stock into a 50 mL Falcon tube containing 5 mL LB medium plus 40 mg/L rifampcin and 200 mg/L spectinomycin, and shaking at 200 rpm at 28° C. The suspension then is centrifuged for 15 minutes at 1600×g at room temperature. The supernatant is discarded, and the pellet is re-suspended in 25 mL of inoculation solution (¹/₁₀ MS salts plus BA (2 mg/L), NAA (0.5 mg/L), glucose (10 g), acetosyringone (200 µM), pluronic F68 (0.05%), pH=5.2 (PhytoTechnology Labs, Shawnee Mission, Kans.)). For leaf transformation, leaf sections are cut from the plants in the Magenta boxes (Caisson Labs, Smithfield, Utah). The adaxial side of each leaf is placed facing up in a Petri dish containing 5 ml *Agrobacterium* suspension. The leaf is cut into ~10 mm strips and immediately placed in an empty Petri dish in non-overlapping manner. When this Petri dish is full, all leaf strips are blotted with the filter paper and placed into another empty Petri dish. The Petri dish is sealed by parafilm and left in the dark at room temperature. The co-cultivation is replaced by this co-desiccation according to Cheng, et al., *In Vitro Cell Dev. Biol. Plant,* 39, 595-604 (2003). After three days, leaf strips are transferred to MSB1T (MS medium with BA (1 mg/L), sucrose (30 g/L), phytagel (3 g/L), and timentin (400 mg/L)) (Cheng, et al., *Plant Cell Rep.,* 17(8):646-649 (1998)) for recovery at low light for 5 days. The leaf strips are then transferred to MSB1TK30 (MS medium containing BA (1 mg/L), sucrose (30 g/L), phytagel (3 g/L), timentin (250 mg/L), and kanamycin (30 mg/L)) for selection under low light for two weeks. The leaf strips are then subcultured every 2 weeks under high light till green shoots emerged. Green shoots 10 mm and longer are transferred to ½MS10.1TK10 for rooting (same as ½MSI0 but with timentin (250 mg/L) and kanamycin (10 mg/L)). After 2-4 weeks, the rooted plantlets are micropropogated and subsequently transplanted into soil.

While the genetically altered guayule are still growing in tissue culture under selection, the genetically altered plants are screened for integration of the expression vectors, pND6-Aos (PaAos in forward orientation; SEQ ID NO: 9), pND6-AosiL (SEQ ID NO: 45 which contains a portion of reverse complement of PaAos (SEQ ID NO: 11)), and pND6 (negative control). DNA is extracted from genetically altered plants using Sigma Kit (Sigma-Aldrich, St. Louis, Mo.). Approximately 150 mg leaf tissue (3 leaf tissues) are cut from the plants grown in tissue-cultured, placed into 2 mL tubes and snapped-frozen in liquid nitrogen. A bead is added to pulverize the tissue into a fine powder at a frequency of 30/s for 1 minute using the mixer mill MM 400 tissue lyser (Verder Scientific, Inc., Newtown, Pa.).

PCR is carried out in 50 µL mixture containing Taq 2× Master Mix (New England Biolabs, Ipswich, Mass.), 200 ng guayule genomic DNA or 20 pg plasmid DNA, and 100 ng of PaAos specific primers; namely SEQ ID NOs: 1 and 2 for guayule transformed with pND6-Aos; and SEQ ID NOs: 3 and 4 for guayule transformed with pND6-AosiL. See FIG. 2. After heating the samples to 94° C. for 2 minutes, the reaction proceeds with 35 cycles of 94° C. for 30 seconds, 71° C. to amplify the PaAos in the overexpression lines (pND6-Aos) for 30 seconds or 56° C. for the PaAos in the RNAi lines (pND6-AosiL) for 30 seconds, and 68° C. for 1 minute. A final elongation step is carried out at 68° C. for 5 minutes. PCR products are separated by electrophoresis on a 1% (w/v) agarose gel. The band for the overexpression lines is at ~1.4 kbp, as expected; the band for the RNAi lines is at ~0.5 kbp as expected. The genetically altered guayule plants harboring the empty plasmid (pND6 (negative control)) are confirmed by GUS staining (Karcher, S., ABLE 23:29-42 (2002)). Briefly, plant tissues are placed in a 50 mL tube containing GUS assay solution (1 mM X-Gluc (5-bromo-4-chloro-3-indolyl) B-D-glucuronic acid in 50 mM $Na_2HPO_4$, pH 7.0 and 0.1% Triton X-100). The reaction is incubated at 37° C. for 1 hour followed by washing for 30 minutes with 70% ethanol to extract the chlorophyll.

Example 2. Determination of RNA Expression Levels in Genetically Altered Plants

Guayule containing intact PaAos (non-altered; G7-11) and genetically altered guayule containing one of the plasmids (pND6, pND6-Aos, or pND6-AosiL) are further screened to determine the RNA level (see Table 3). Leaves from the various genetically altered plants (which are grown in tissue culture) are collected and snap-frozen in liquid nitrogen for RNA extraction. RNA is extracted using TRIzol® according to manufacturer's recommended protocol (Ambion, Pittsburgh, Pa.). RNA concentration is quantified with the NanoDrop ND1000 (ThermoScientific, Wilminton, Del.). RNA cleanup is performed using the RNeasy MinElute Cleanup kit according to manufacturer's recommended protocol (Qiagen Inc., Valencia, Calif.). The RNA is eluted with 30-50 µL of RNase-free water along with on-column DNaseI treatment.

Using the RNA isolated from the leaves of the genetically altered plants, cDNA is generated using iScript cDNA synthesis kit (Bio-Rad, Hercules, Calif.) according to the manufacturer's recommended protocol for semi-quantitative PCR and real-time quantitative PCR (qRT-PCR). An amount of 1 µg of RNA is used in the 20 mL reaction mixture. For qRT-PCR, 2 µL of the diluted cDNA (1:20) is used in a 15 µL reaction mixture. In the qRT-PCR volume, 7.5 mL of iQ SYBR® Green Supermix is used (Bio-Rad, Hercules, Calif.). The qRT-PCR is run using the 7500 Fast Real-Time PCR system (Applied Biosystem, Waltham, Mass.) with the following thermal cycle: 95° C. pre-incubation for 3 minutes; amplification is performed for 40 cycles at 95° C. for 15 seconds and at 60° C. for 30 seconds; the dissociation stage is set for 95° C. for 15 seconds, at 60° C. for 1 minute, and at 95° C. for 15 seconds. Each qRT-PCR run is performed with three independent tissue samples, each sample having two technical replicates. The 18S gene (~200 bp) is used as an internal control. The primers used for each sequence, PCR reaction conditions, and the expected amplicon size are contained in FIG. 2. Crossing point value, which is the point at which the fluorescence crosses the threshold, and melting curve analyses are noted. The melting curve data are collected for all genes to ensure a single peak, indicating amplification of a specific region by a pair of primers. The relative expression values are calculated using the 2(−Delta C(T)) method (Livak and Schmittgen, *Methods,* 25:402-408 (2001)). See Table 3 below.

TABLE 3

| *P. argentatum* Genotypes | Average Relative Expression of Aos |
| --- | --- |
| G7-11 | 1.02 ± 0.2 |
| pND6-10 | 1.14 ± 0.2 |
| pND6-12 | 1.02 ± 0.3 |
| pND6-29 | 1.04 ± 0.2 |
| pND6-32 | 1.00 ± 0.3 |
| pND6-33 | 1.11 ± 0.3 |
| pND6-35 | 0.90 ± 0.2 |
| pND6-41 | 0.91 ± 0.2 |
| pND6-AosiL$_{5-1}$ | 0.39 ± 0.1* |
| pND6-AosiL$_{7-2}$ | 0.49 ± 0.1* |
| pND6-AosiL$_{8-1}$ | 0.53 ± 0.1* |
| pND6-AosiL$_{9-15}$ | 0.44 ± 0.1* |
| pND6-AosiL$_{9-16}$ | 0.37 ± 0.04* |
| pND6-AosiL$_{12-1}$ | 0.55 ± 0.1* |
| pND6-AosiL$_{12-3}$ | 0.48 ± 0.1* |
| pND6-AosiL$_{13-2}$ | 0.55 ± 0.05* |
| pND6-AosiL$_{15-3}$ | 0.36 ± 0.1* |
| pND6-AosiL$_{15-4}$ | 0.48 ± 0.2* |
| pND6-Aos$_{4-1}$ | 2.15 ± 0.1** |
| pND6-Aos$_{4-2}$ | 2.11 ± 0.3** |
| pND6-Aos$_{5-1}$ | 2.29 ± 0.4** |
| pND6-Aos$_{7-1}$ | 2.40 ± 0.6** |
| pND6-Aos$_{7-3}$ | 2.11 ± 0.2** |
| pND6-Aos$_{8-2}$ | 2.15 ± 0.2** |
| pND6-Aos$_{10-1}$ | 2.44 ± 0.7** |

TABLE 3-continued

| P. argentatum Genotypes | Average Relative Expression of Aos |
|---|---|
| pND6-Aos$_{10-2}$ | 2.12 ± 0.4** |
| pND6-Aos$_{11-5}$ | 2.30 ± 0.3** |
| pND6-Aos$_{14-2}$ | 2.23 ± 0.1** |

G7-11 = wild-type control;
pND6 = empty vector (pND6 without Aos);
pND6-AosiL = PaAos is knocked-down/silenced;
pND6-Aos = PaAos is over-expressed
Results are average of three independent plants, each plant having three technical replicates.
* and ** indicate significant difference in comparison to G7-11 guayule and/or pND6 (controls) at p > 0.05 and 0.005, respectively.

Next, to gain more insight as to where the PaAos is spatially located, the expression pattern of PaAos in various guayule tissues is analyzed using qRT-PCR. Total RNA is extracted from leaves, petiole, stem, root, young flower, mature flower, peduncle, stembark of 8-week-old tissue-cultured genetically altered plants as well as 2-month-old greenhouse grown genetically altered plants using the protocol described above. qRT-PCR is performed as described above on these samples of total RNA. Primers (SEQ ID NOs: 7 and 8 in FIG. 2) are designed to amplify ~200 bp PCR product in PaAos coding sequence. The expression level for each tissue are compared to the tissue cultured and greenhouse leaf tissues, respectively. The 18S gene (~200 bp) (forward primer is SEQ ID NO: 5 and reverse primer is SEQ ID NO: 6, described supra and in FIG. 2) is used as an internal control. As shown in Table 4, infra, the largest level of PaAos expression is present in the stem, root and stembark tissues, suggesting that these tissues are sites in which PaAos is functioning.

TABLE 4

| | Growth Conditions: | |
|---|---|---|
| Tissue Source | MS Medium Relative Expression | Greenhouse |
| Leaf | 0.98 ± 0.1 | 1.04 ± 0.2 |
| Petiole | 0.31 ± 0.06 | 0.41 ± 0.1 |
| Stem | 2.27 ± 0.2 | 3.37 ± 0.4 |
| Root | 2.47 ± 0.2 | 3.74 ± 0.3 |
| Young Flower | no data | 1.23 ± 0.4 |
| Mature Flower | no data | 0.69 ± 0.2 |
| Peduncle | no data | 0.25 ± 0.1 |
| Bark | no data | 4.49 ± 1.2 |

The error bars represent tissues collected from 3 individual plants.

Example 3. Rubber Quantification in Tissue

Rooted plantlets (genetically altered, empty vector transformed (pND6 without PaAos), and wild-type control) from transferred shoot tips are grown on half-strength MS medium (PhytoTechnology Laboratories, Overland Park, Kans.) in Magenta boxes (Caisson Labs, Smithfield, Utah) for 6 weeks. The top part of the plantlets are separated from the medium and lyophilized for 48 hours. The dried tissues are placed in a 50 mL stainless steel grinding jar containing grinding ball, frozen in liquid nitrogen for 5 minutes and finely ground using the Retsch mixer mill MM 400 at a frequency of 30/second for 1 minute (Verder Scientific Inc., Newtown, Pa.). Three hundred milligrams (0.3 g) of pulverized tissues are partitioned with Ottawa sand (Fisher Scientific, Fair Lawn, N.J.) and loaded into 11 mL stainless steel extraction cells (Dionex, Sunnyvale, Calif.). Three sequential extractions are performed using the Accelerated Solvent Extractor (ASE 2000; Dionex, Sunnyvale, Calif.): 1. Acetone: to remove resinous material and the low molecular weight organic solubles; 2. Methanol: to remove chlorophyll and other alcohol-soluble materials; 3. Cyclohexane: to remove rubber. Natural rubber is quantified gravimetrically. The percent (%) rubber is the amount (% dw) of cyclohexane extract from 0.3 g dried tissue. The pND6-AosiL plants have 1.5 to 2 times more rubber than G7-11, pND6 and pND6-Aos in tissue-cultured environment (Table 5). In Table 5, the rubber content is quantified from leaf and stems of the indicated guayule genotypes grown in MS media.

TABLE 5

Rubber content of guayule plant shoots determined by Accelerated Solvent Extraction

| P. argentatum Genotypes | Average Rubber Content (%) |
|---|---|
| G7-11.1 | 1.01 ± .01 |
| G7-11.2 | 1.11 ± .02 |
| pND6-12 | 1.13 ± 0.2 |
| pND6-33 | 1.10 ± 0.1 |
| pND6-35 | 1.04 ± 0.2 |
| pND6-AosiL$_{5-1}$ | 1.8 ± 0.1* |
| pND6-AosiL$_{7-2}$ | 2.0 ± 0.3** |
| pND6-AosiL$_{8-1}$ | 2.1 ± 0.04*** |
| pND6-AosiL$_{8-2}$ | 1.7 ± 0.1** |
| pND6-AosiL$_{9-15}$ | 1.7 ± 0.02** |
| pND6-AosiL$_{9-16}$ | 2.3 ± 0.4* |
| pND6-AosiL$_{12-1}$ | 2.46 ± 0.3* |
| pND6-AosiL$_{12-3}$ | 1.62 ± 0.002*** |
| pND6-Aos$_{4-1}$ | 0.96 ± 0.2 |
| pND6-Aos$_{4-2}$ | 0.85 ± 0.1 |
| pND6-Aos$_{5-1}$ | 1.09 ± 0.1 |
| pND6-Aos$_{5-2}$ | 1.23 ± 0.1 |
| pND6-Aos$_{7-1}$ | 0.96 ± .02 |
| pND6-Aos$_{8-2}$ | 1.23 ± 0.1 |
| pND6-Aos$_{11-5}$ | 1.23 ± 0.1 |

Note:
The rubber content is quantified from shoots (leaves + stems) of guayule genotypes grown in MS media.
Error bars represent three biological plants with three technical replicates each.
*,  and * indicate significant difference in comparison to G7-11 guayule and/or pND6 (controls) at p > 0.05, 0.005 and 0.0005, respectively.

Next, the genetically altered guayule plants are transplanted into soil and grown for 2 months under 27° C. (16 h)/25° C. (8 h) and 27° C. (16 h)/10° C. (8 h) in growth chamber conditions, representing a microcosm of what guayule plants experience in the field during winter. Under these conditions, pND6-AosiL plants also exhibited elevated rubber content, having up to 31% times more rubber in comparison with G7-11, pND6 and pND6-Aos plants (Table 6). In Table 6, the rubber content is quantified from shoots and roots of the indicated guayule genotypes grown in soil. These plants are approximately 4 months old when rubber content is analyzed (tissue culture (approx. 1.5 months), greenhouse (approx. 1 month), and growth chamber (approx. 2 months)).

TABLE 6

Rubber content of guayule plant tissue determined by Accelerated Solvent Extraction

| | Average Rubber Content (%) | | | |
|---|---|---|---|---|
| | Shoot | | Root | |
| P. argentatum Genotypes | 27° C. (16 h)/ 25° C. (8 h) | 27° C. (16 h)/ 10° C. (8 h) | 27° C. (16 h)/ 25° C. (8 h) | 27° C. (16 h)/ 10° C. (8 h) |
| G7-11.1 | 1.22 + 0.09 | 1.13 + 0.11 | 1.10 + 0.04 | 0.95 + 0.10 |
| G7-11.2 | 1.06 + 0.12 | 1.37 + 0.09 | 0.63 + 0.12 | 0.71 + 0.09 |
| pND6-12 | 1.04 + 0.18 | 1.31 + 0.06 | 0.65 + 0.07 | 0.72 + 0.16 |
| pND6-33 | 0.90 + 0.06 | 1.14 + 0.12 | 0.62 + 0.08 | 0.82 + 0.10 |
| pND6-35 | 1.18 + 0.08 | 1.27 + 0.10 | 1.09 + 0.06 | 0.94 + 0.03 |
| pND6-AosiL$_{7-2}$ | 1.49 + 0.07*** | 1.86 + 0.11*** | 0.56 + 0.03 | 1.26 + 0.09** |
| pND6-AosiL$_{8-1}$ | 1.48 + 0.05*** | 1.91 + 0.07*** | 0.78 + 0.14 | 1.19 + 0.04** |
| pND6-AosiL$_{9-16}$ | 1.46 + 0.04*** | 2.01 + 0.08*** | 0.66 + 0.12 | 1.16 + 0.02** |
| pND6-AosiL$_{12-1}$ | 1.55 + 0.07* | 1.80 + 0.05** | 1.26 + 0.04*** | 1.52 + 0.07** |
| pND6-Aos$_{4-1}$ | 0.97 + 0.26 | 1.13 + 0.2 | 0.57 + 0.05 | 0.79 + 0.09 |
| pND6-Aos$_{4-2}$ | 1.21 + 0.10 | 1.30 + 0.08 | 1.05 + 0.10 | 0.94 + 0.11 |
| pND6-Aos$_{5-1}$ | 0.98 + 0.30 | 1.04 + 0.12 | 0.54 + 0.11 | 0.62 + 0.10 |
| pND6-Aos$_{7-1}$ | 0.96 + 0.30 | 1.15 + 0.14 | 0.57 + 0.06 | 0.55 + 0.08 |

Note:
The rubber content is quantified from shoots and roots of guayule genotypes grown in soil.
Plants are transferred to soil from tissue culture and are grown in a growth chamber environment. Error bars represent three biological plants with three technical replicates each.
*,  and * indicate significant difference in comparison to G7-11 and/or pND6 (controls) at p > 0.05, 0.005 and 0.0005, respectively.

Because rubber is also accumulated in root tissue, the rubber content in the root tissues is also quantified. For the root rubber content, the consistent, significant difference is only under 27° C. (16 h)/10° C. (8 h) in which pND6-AosiL guayule have an increased in rubber content compared with the controls and pND6-Aos (Table 6). The data in Table 6 demonstrate that the combination of cold temperature and silencing PaAos is synergistic, causing guayule to produce a greater amount of rubber than guayule exposed to just cold temperature or to just PaAos silencing. For example, cold treatment alone increased shoot rubber content in the control (pND6-12) by 19%—from an average of 1.04% to 1.24%. But cold treatment of the Aos-downregulated plants (pND6-AosiL) increased rubber by 27%—from average 1.50% to 1.90%. In root tissues, cold treatment increased the rubber content for the control (pND6-12) by 5.1% (from 0.79 to 0.83% rubber), but cold treatment of the Aos-downregulated plants (pND6-AosiL) increased rubber by 57%—from average 0.82% to 1.28%. See Table 7, infra. From the ASE results, the increased in rubber content is very apparent in the pND6-AosiL genotypes.

TABLE 7

| | Average Rubber Content (%) | | | |
|---|---|---|---|---|
| | Shoot | | Root | |
| P. argentatum Genotypes | 27° C. (16 h)/ 25° C. (8 h) | 27° C. (16 h)/ 10° C. (8 h) | 27° C. (16 h)/ 25° C. (8 h) | 27° C. (16 h)/ 10° C. (8 h) |
| pND6-12 | 1.04 | 1.24 | 0.79 | 0.83 |
| pND6-AosiL$_{7-2}$ | 1.50 | 1.90 | 0.82 | 1.28 |
| pND6-Aos$_{4-1}$ | 1.03 | 1.16 | 0.68 | 0.73 |

Example 4. Protein Detection in Rubber Particles

Guayule washed rubber particles (WRPs) are isolated from genetically altered guayule lines (pND6-AosiL and pND6-Aos) and non-altered guayule using the protocol set forth in Cornish and Backhaus, Phytochemistry, 29: 3809-3813 (1990). Rubber particles are extracted from non-altered and genetically altered 1 year old greenhouse plants. First, ~60 g to ~70 g of stembark tissues are peeled off from the plant, grounded with a blender containing cold-extraction buffer, and further purified with cold-washed buffer three times by centrifugation. The protein extracts (1 mg) are run on an SDS-PAGE and detected with silver staining. On the SDS-PAGE gel, endogenous Aos protein runs as ~53 kDa in the non-altered and overexpressed plants but not in the RNAi lines. To determine the dry weight of the WRPs, 50 μL of the protein extracts are aliquoted 3× on a weighing paper, oven-dried over-night in a 60° C. incubator and weighed the next day. Generally, approximately 0.5 mg/μL to approximately 1.5 mg/μL WRPs are extracted.

Example 5. Hormone Production

PaAos is an enzyme in the biosynthetic pathway that produces several different plant hormones, including jasmonic acid, SA, abscisic acid, gibberellin $A_{20}$, gibberellin $A_1$, and gibberellin $A_3$. As such, the amount of these hormones is quantified in genetically altered (pND6-AosiL and pND6-Aos), empty vector transformed (pND6 without PaAos; control), and wild-type (G7-11, control) tissue-cultured guayule plants using the protocol described in Pan et al., Nature Protocols 5:986-992 (2010). See Table 8, infra. Briefly, leaves and stems are snap-frozen and ground to powder with mortar and pestle. Solvent extraction solution containing 2-propanol/$H_2O$/concentrated HCl (2:1:0.002; vol/vol/vol) and internal standards are added to ~50 mg of pre-weighed tissues. After solvent extraction, sample concentration and re-dissolution, 50 μL of the sample solution is placed into the liquid chromatography-tandem spectrometry (Agilent GC-MS 5977A; Agilent Technologies, Santa Clara, Calif.) for hormone analysis. Three biological plants, with three technical replicates of each plant, are used.

TABLE 8

| P. argentatum Genotypes | Concentration (ng/gfw) | | | | | |
|---|---|---|---|---|---|---|
| | Jasmonic Acid | Salicylic Acid | Abscisic Acid | Gibberellin $A_{20}$ | Gibberellin $A_1$ | Gibberellin $A_3$ |
| G7-11 | 5.36 ± 1.2 | 5.50 ± 0.8 | 11.01 ± 1.9 | 15.95 ± 0.7 | 9.95 ± 0.07 | 3.52 ± 0.2 |
| pND6-12 | 1.57 ± 0.1 | 4.89 ± 0.6 | 7.05 ± 0.8 | 14.11 ± 1.2 | 12.39 ± 2.2 | 2.19 ± 0.01 |
| pND6-33 | 4.76 ± 1.0 | 5.04 ± 0.1 | 7.24 ± 0.3 | 13.86 ± 2.6 | 12.70 ± 2.3 | 1.79 ± 0.09 |
| pND6-35 | 1.96 ± 0.4 | 5.6 ± 0.5 | 7.10 ± 0.6 | 14.41 ± 1.2 | 14.65 ± 0.2 | 2.16 ± 0.3 |
| pND6-AosiL$_{7-2}$ | 0.57 ± 0.1** | 9.51 ± 0.5* | 4.71 ± 0.6* | 9.63 ± 1.2* | 5.13 ± 0.8* | 0.86 ± 0.3* |
| pND6-AosiL$_{9-16}$ | 0.57 ± 0.01** | 7.65 ± 0.2* | 2.96 ± 0.3* | 8.85 ± 2.1* | 7.81 ± 0.2** | 0.80 ± 0.3* |
| pND6-AosiL$_{12-1}$ | 0.68 ± 0.05** | 9.65 ± 1.1* | 3.64 ± 0.5* | 10.59 ± 0.2* | 6.75 ± 1.1* | 1.32 ± 0.07* |
| pND6-A$_{oc4-1}$ | 1.48 ± 0.2 | 4.03 ± 0.7 | 9.13 ± 1.71 | 15.49 ± 0.6 | 10.78 ± 0.1 | 1.93 ± 0.06 |
| pND6-A$_{os4-2}$ | 3.25 ± 0.2 | 4.76 ± 0.6 | 13.9 ± 1.3 | no data | 14.63 ± 2.7 | 1.80 ± 0.1 |
| pND6-A$_{os7-1}$ | 1.41 ± 0.3 | 5.50 ± 0.02 | 8.84 ± 0.3 | 13.64 ± 1.2 | 13.96 ± 0.01 | 1.84 ± 0.1 |

± represent three biological plants with three technical replicates each plant.
* and ** indicate significant difference in comparison to G7-11 and/or pND6 (controls) at p > 0.05 and 0.005, respectively.

As evident in Table 8, the amount of jasmonic acid, abscisic acid and gibberellic acids are reduced in the pND6-AosiL guayule compared to the amount in the controls (wild-type (G7-11) and empty vector transformed plants) and pND6-Aos guayule. Conversely, the SA content is elevated in pND6-AosiL compared to the controls and pND6-Aos lines. These results suggest that knocking down PaAos expression not only reduces production of jasmonic acid but also affects the level of other hormones as well.

Example 6. Plant Architecture and Photosynthetic Rates

Figure 4:
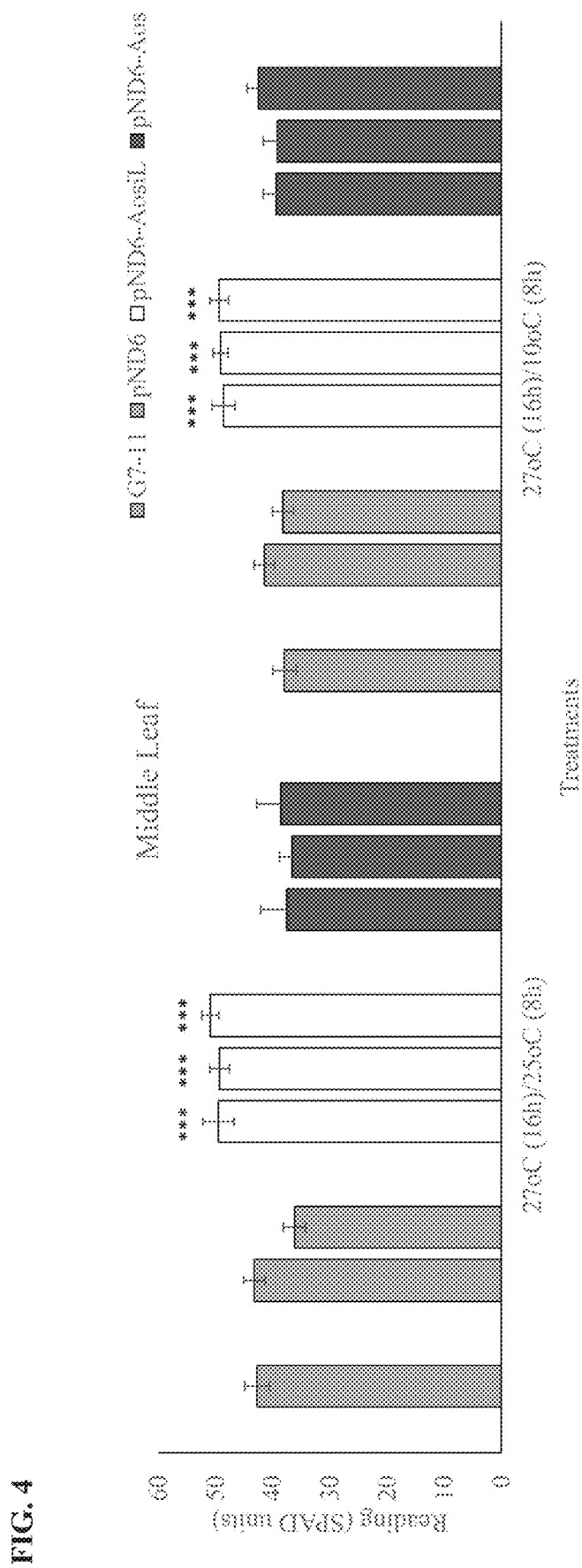
FIG. 4 shows SPAD values indicating leaf chlorophyll concentration ("SPAD units") for wild-type guayule (G7-11), guayule transformed with the empty expression vector (pND6); guayule transformed with pND6-Aos (Oe), and guayule transformed with pND6-AosiL (RNAi) grown at 27° C. (16 h)/25° C. (8 h) or 27° C. (16 h)/10° C. (8 h).

Three independent events from each of the overexpression (pND6-Aos) and of the silenced (pND6-AosiL) lines; as well as two pND6 and one wild-type (G7-11) controls are selected for further studies. pND6-AosiL plants grown in greenhouse (data not shown) and growth chamber conditions are bigger (see FIG. 3)), have darker green leaves (data not shown), and increased chlorophyll measurement than the wild type and other genetically altered plants (see FIG. 4). As demonstrated in FIG. 3, under 27° C. (16 h)/25° C. (8 h) and 27° C. (16 h)/10° C. (8 h) environments, pND6-AosiL plants are significantly taller and wider in both conditions. These plant architectural traits reflect the fact that pND6-AosiL plants are larger and have more shoot and root biomass.

pND6-AosiL genotypes have also a greater number of stems than the wild-type and empty vector controls. Well-branched guayule plants are an indicator of having increased rubber yield because of the presence of more sink tissue available to store rubber. Additionally, the mature stembark tissues in pND6-AosiL have thicker diameter (ranging from approximately 35% to approximately 54%) under both 27° C. (16 h)/25° C. (8 h) and 27° C. (16 h)/10° C. (8 h) in comparison to the controls and pND6-Aos. See FIG. 5.

Based on this observation, the photosynthetic rate of the plants is measured using LI-COR 6400xt (LI-COR Biosciences, Lincoln, Nebr.) to measure the photosynthetic rate. Measurements are taken between 0900 to 1200 h. Fully expanded middle leaf are clamped on the Li-Cor head. After the measured and set parameters are stabilized, the reading is taken. The middle leaf position is chosen because this position shows significant differences based on chlorophyll meter measurements, FIG. 4. (SPAD-502; Minolta Camera Ltd., Japan). The pND6-AosiL plants exhibit higher photosynthetic rate (23-31%) in comparison to G7-11, pND6 and pND6-Aos plants (Table 9, infra). Additional physiological measurements reveal that pND6-AosiL stomatal limitation is one of the factors involved in the higher photosynthetic rate as pND6-AosiL plants show higher stomatal conductance and transpiration rate when compared to G7-11, pND6 and pND6-Aos plants (Table 9, infra). Furthermore, chlorophyll fluorescence measurements clearly show PSII and ETR parameters used for elucidating the efficiency of PSII are significantly higher than G7-11, pND6 and pND6-Aos plants (Table 9, infra) in both 27° C. (16 h)/25° C. (8 h) and 27° C. (16 h)/10° C. (8 h) treatment conditions. Having higher PSII and ETR indicate that amount of light energy absorbed and carbon assimilated is available more in pND6-AosiL plants to convert into energy for the plant to use (i.e., growth and development as well as rubber production) compared to the controls and pND6-Aos plants. Meanwhile, the NPQ measurements for the pND6-AosiL plants are lower under the 27° C. (16 h)/25° C. (8 h) condition and higher under the 27° C. (16 h)/10° C. (8 h) treatment in comparison with the controls and pND6-Aos plants. Having higher NPQ suggests that pND6-AosiL have improved heat dissipation ability compared to G7-11, pND6 and pND6-Aos plants which could help prevent lipid or other cell membrane damage under environmental stress.

TABLE 9

| P. argentatum Genotypes | 27° C. (16 h)/25° C. (8 h) | | | | | |
|---|---|---|---|---|---|---|
| | Pn | g | $\epsilon$ | $\Phi$PSII | ETR | NPQ |
| G7-11 | 5.75 ± 0.8 | 0.093 ± 0.03 | 2.33 ± 0.6 | 0.146 ± 0.015 | 115.73 ± 11.3 | 1.97 ± 0.2 |
| pND6-10 | 6.29 ± 0.7 | 0.110 ± 0.03 | 2.74 ± 0.6 | 0.141 ± 0.015 | 111.1 ± 11.6 | 1.74 ± 0.1 |
| pND6-12 | 6.20 ± 0.8 | 0.109 ± 0.02 | 2.66 ± 0.5 | 0.145 ± 0.015 | 114.4 ± 12.1 | 1.90 ± 0.2 |
| pND6-AosiL$_{7-1}$ | 8.56 ± 0.6*** | 0.147 ± 0.01*** | 3.41 ± 0.3*** | 0.196 ± 0.027* | 165.2 ± 10.7*** | 1.33 ± 0.2*** |
| pND6-AosiL$_{8-1}$ | 8.40 ± 0.6*** | 0.155 ± 0.02*** | 3.67 ± 0.4*** | 0.180 ± 0.008* | 141.4 ± 6.2** | 1.27 ± 0.2*** |
| pND6-AosiL$_{9-16}$ | 7.96 ± 0.5*** | 0.162 ± 0.03*** | 3.57 ± 0.5*** | 0.186 ± 0.018* | 134.4 ± 3.3** | 1.19 ± 0.3*** |
| pND6-A$_{os4-1}$ | 5.62 ± 0.9 | 0.110 ± 0.04 | 2.59 ± 0.7 | 0.133 ± 0.008 | 104.7 ± 6.7 | 1.92 ± 0.3 |

TABLE 9-continued

| | | | | | | |
|---|---|---|---|---|---|---|
| pND6-A$_{os5-1}$ | 5.70 ± 0.8 | 0.110 ± 0.04 | 2.60 ± 0.7 | 0.133 ± 0.008 | 104.7 ± 6.7 | 1.95 ± 0.3 |
| pND6-A$_{os7-1}$ | 5.87 ± 0.9 | 0.113 ± 0.04 | 2.65 ± 0.7 | 0.137 ± 0.008 | 107.7 ± 6.3 | 2.07 ± 0.4 |

| *P. argentatum* | 27° C. (16 h)/10° C. (8 h) | | | | | |
|---|---|---|---|---|---|---|
| Genotypes | Pn | g | ϵ | ΦPSII | ETR | NPQ |
| G7-11 | 2.23 ± 0.5 | 0.054 ± 0.02 | 1.31 ± 0.4 | 0.070 ± 0.007 | 55.4 ± 5.4 | 1.58 ± 0.2 |
| pND6-10 | 2.04 ± 0.4 | 0.057 ± 0.02 | 1.55 ± 0.3 | 0.064 ± 0.006 | 50.7 ± 4.9 | 1.56 ± 0.2 |
| pND6-12 | 2.28 ± 0.4 | 0.065 ± 0.03 | 1.67 ± 0.7 | 0.066 ± 0.003 | 51.6 ± 2.7 | 1.51 ± 0.3 |
| pND6-AosiL$_{7-1}$ | 4.14 ± 0.4*** | 0.104 ± 0.02*** | 2.54 ± 0.4*** | 0.104 ± 0.011*** | 81.0 ± 8.2*** | 2.29 ± 0.3** |
| pND6-AosiL$_{8-1}$ | 4.15 ± 0.4*** | 0.112 ± 0.05*** | 2.71 ± 0.8*** | 0.102 ± 0.013*** | 77.0 ± 4.5*** | 2.33 ± 0.2** |
| pND6-AosiL$_{9-16}$ | 4.14 ± 0.6*** | 0.101 ± 0.03*** | 2.60 ± 0.5*** | 0.101 ± 0.009*** | 79.4 ± 6.9*** | 1.95 ± 0.1** |
| pND6-A$_{os4-1}$ | 2.27 ± 0.5 | 0.059 ± 0.02 | 1.51 ± 0.3 | 0.065 ± 0.011 | 60.4 ± 5.5 | 1.35 ± 0.3 |
| pND6-A$_{os5-1}$ | 2.97 ± 0.3 | 0.069 ± 0.01 | 1.81 ± 0.2 | 0.077 ± 0.007 | 58.5 ± 6.3 | 1.25 ± 0.2 |
| pND6-A$_{os7-1}$ | 2.45 ± 0.6 | 0.063 ± 0.01 | 1.93 ± 0.3 | 0.065 ± 0.010 | 50.1 ± 5.8 | 1.44 ± 0.2 |

Pn = net photosynthetic rate;
g = stomatal conductance;
E = Transpiration rate;
ΦPSII = Efficiency of Photosystem II;
ETR = Electron Transport Rate;
NPQ = Non-photochemical quenching
*,  and * indicate significant difference in comparison to G7-11 and/or pND6 (controls) at p > 0.05, 0.005 and 0.0005, respectively.

Example 7. Quality of Natural Rubber from pND6-AOSiL Plants

Figure 6:
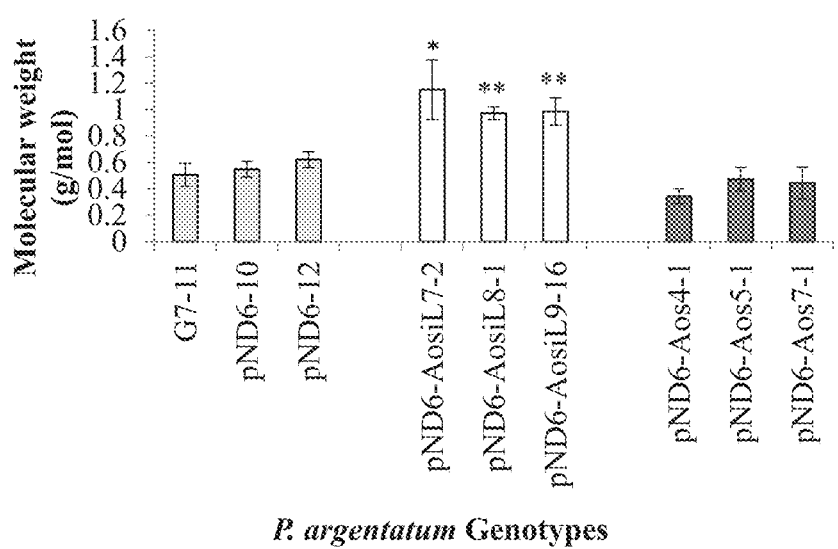
FIG. 6 shows results from gel permeation chromatography for elution of cyclohexane extractables from transformed and non-altered guayule plant lines. The natural rubber molecular weight is calculated using Astra software for three pND6-AosiL transformed guayule plants, three pND6-Aos transformed guayule plants, two pND6 transformed guayule plants, and non-altered guayule G7-11. The error bars represent 3 different plants with 3 technical replicates.

The length of the polymer chain, a.k.a. rubber molecular weight, is the primary determinant of quality in natural rubber. Gel permeation chromatography (GPC) is used to measure the molecular weight of rubber from guayule tissue culture plants' extracts. Cyclohexane extractables collected from ASE (see Example 3 and Table 5 supra) are re-suspended in approximately 3 mL of tetrahydrofuran (THF) overnight with gentle shaking (Multi-Purpose Rotator, Thermo Scientific, Waltham, Mass.). The solution is syringe-filtered through a 1.6 μm glass microfiber GF/A filter (Whatman GE Healthcare, Piscataway, N.J.), then injected into a Hewlett Packard 1100 series HPLC (1.0 mL/min flow rate, 50 μL injection volume, THF continuous phase) and size exclusion separated by two Agilent PL gel 10 μm Mixed-B columns in series (35° C.) (Santa Clara, Calif.). The resulting chromatograms are used to calculate the rubber molecular weight shown in FIG. 6 (using Astra software (Wyatt Technology Corp., Santa Barbara, Calif.)). The molecular weight of natural rubber from three pND6-AosiL transformed guayule plants (silenced) is greater than from wild-type guayule line G7-11, two negative control pND6 transformed guayule plants and three pND6-Aos transformed guayule plants (overexpressed) indicating better quality rubber in the PaAos silenced guayule plants. In FIG. 6, the asterisks (*) and (**) above the three pND6-AosiL transformed guayule plant lines indicate significant difference in comparison to the negative control pND6 transformed guayule plant lines at p>0.05 and p>0.005, respectively.

Figures 7, 8:
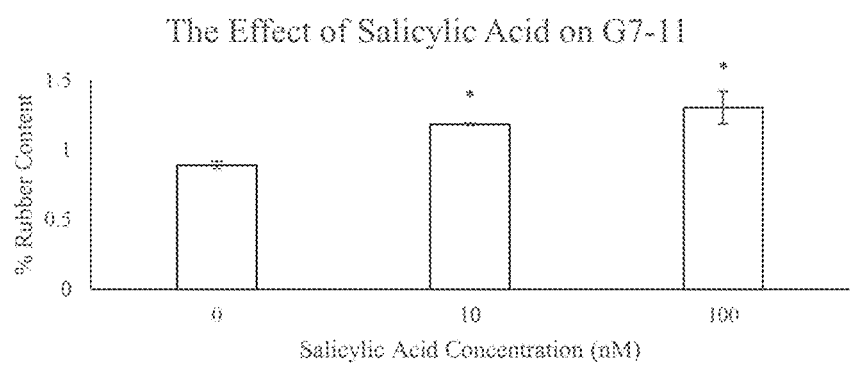
FIG. 7 shows the rubber content of SA (0 nM, 10 nM, and 100 nM) treated guayule G7-11 plants.
FIG. 8 shows PaAOS relative expression and rubber content analyzed by ASE in one month old soil-grown guayule G7-11 plants treated with salicylic acid for 2 months and grown in greenhouse settings.

Example 8. Exogenous Salicylic Acid (SA) Addition Reduces PaAos Gene Expression The effect of SA on guayule PaAos gene expression is tested in wild-type guayule G7-11 plants. SA is added to the growth medium (K0) in tissue culture at different concentrations, 0 nM, 10 nM and 100 nM. Shoot tips are transferred to the growth media, and plants are grown for 8 weeks. The rubber content of the plant tissues is determined by standard procedures (ASE, see Example 3 supra). In comparison to 0 nM of SA, the addition of 10 nM and 100 nM of SA increases the amount of rubber produced in a significant manner. See FIG. 7. The effect of exogenous 10 nM SA on one month old guayule plants grown in the soil under greenhouse conditions is also examined. 50 ml of 10 nM SA solution of water and 0.0005% ethanol is administered to the soil twice weekly for two months and results in significant differences in the height and primary stem diameter relative to mock or water treated G7-11 plants (FIG. 8). The qRT-PCR results of PaAOS from the SA treated plants also show low expression pattern. The rubber content in the SA treated plants slightly increases and significantly differs compared to the mock treated G7-11 plants (FIG. 8). These data demonstrate that guayule's rubber content is increased by exogenous addition of SA to the plant.

Example 9. Transcription Factor Overexpression Results in More Rubber Production PaAos promoter sequence is obtained (SEQ ID NO: 18) and is analyzed for transcription factors' binding sites using PlantPAN2.0 software (plantpan2.itps.ncku.edu.tw). The binding sites of a number of transcription factors, including WRKY3, WRKY71, MYBS3, CBF, and FLC, are identified. See FIGS. 11A-11C, and Chen, et al., *BMC Genomics* 12:85-97 (2012). The Hevea nucleotide sequences of WRKY3, WRKY71, and MYBS3 are used to identify the DNA sequence of these three transcription factor genes in *P. argentatum* by searching for high percent identical sequences in a *P. argentatum* EST database in NCBI (using a computer algorithm, "BLAST") and also in a newly assembled guayule genome (unpublished).

Based on the sequence information obtained from the sequence comparisons, RT-PCR forward primers and reverse primers are designed to amplify partial coding sequence of guayule's WRKY3-like (SEQ ID NOs: 19 and 20), WRKY71-like (SEQ ID NOs: 21 and 22), and MYBS3-like (SEQ ID NOs: 23 and 24). FIG. 12 contains these sequences as well as the annealing temperature and amplicon's size. These primers are used in the following protocol to isolate the coding sequences of the indicated transcription factors.

Figure 13A:
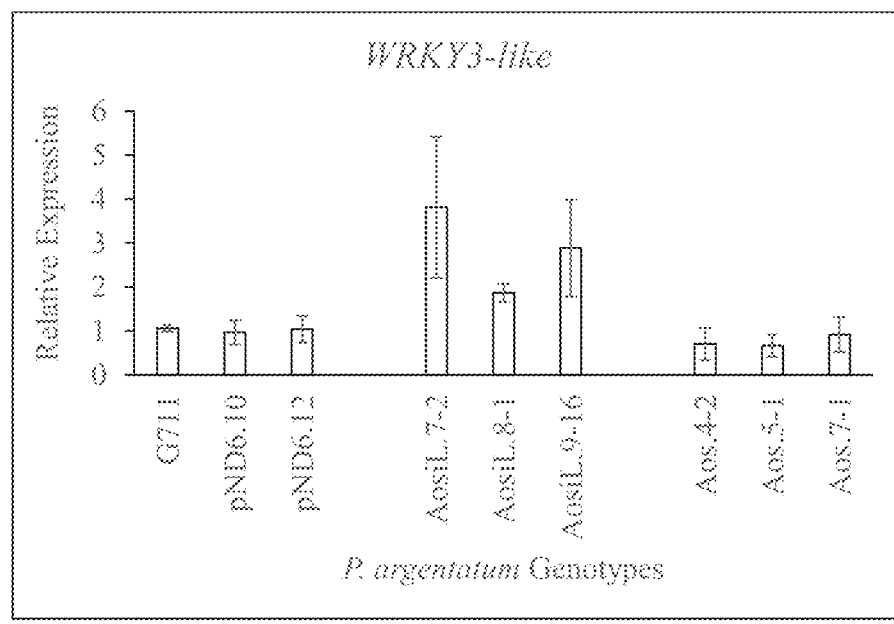
FIGS. 13A-13C show the relative expression of WRKY3-like (FIG. 13A), WRKY71-like (FIG. 13B), and MYBS3-like (FIG. 13C) in non-altered guayule, genetically altered guayule with PaAos silenced, and genetically altered guayule with PaAos overexpressed.
Figure 13B:
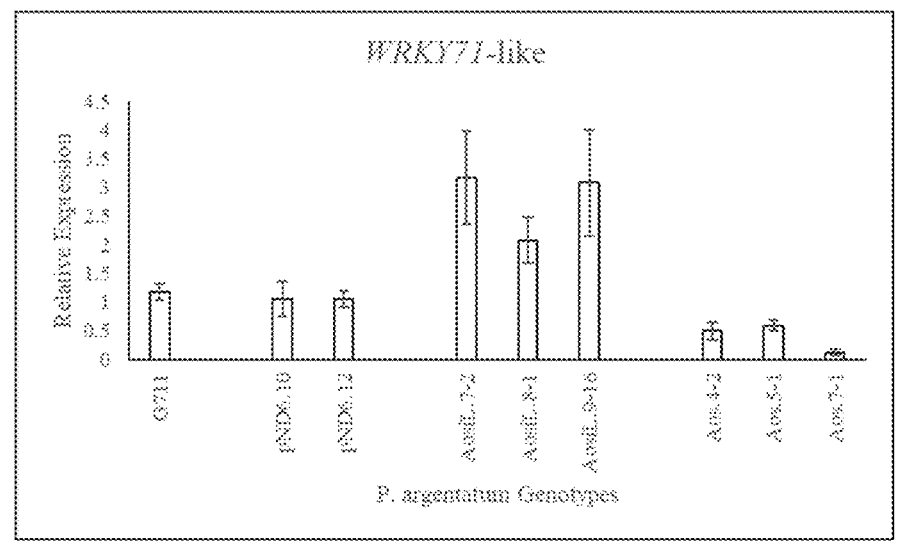
Figure 13C:
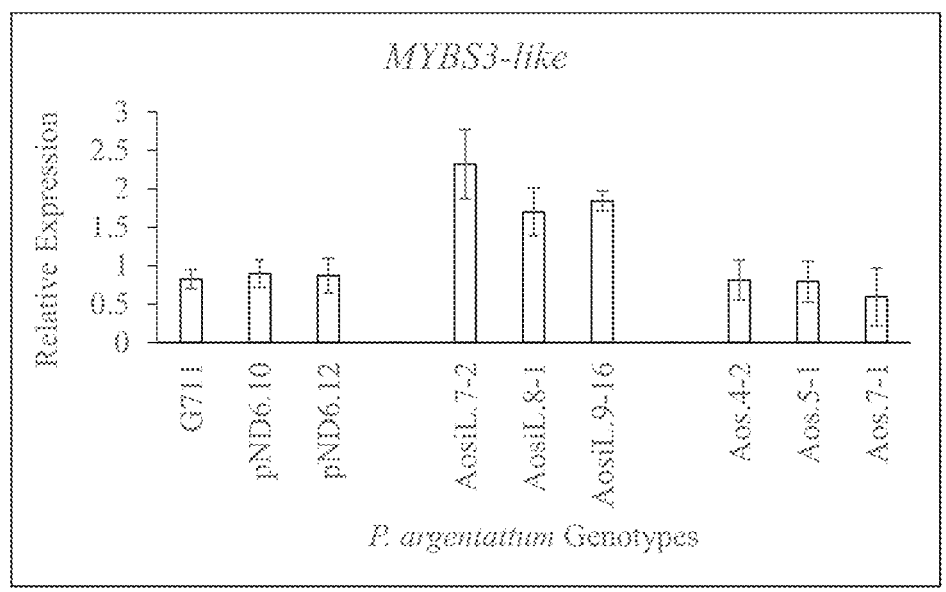

Approximately 150 mg stem tissue (4 stem tissues) are cut from guayule plants grown in tissue-cultured, placed into 2 mL tubes, and snapped-frozen in liquid nitrogen. Mortar and pestle are used to pulverize the tissues into a fine powder. RNA is extracted, quantified, and cleaned up using the protocols describe above in Example 2. Using the RNA isolated from the stem of wild-type guayule (line G7-11) and genetically altered guayule (i.e., pND6, pND6-AOSiL and pND6-AOS lines described above) cDNA is generated using iScript cDNA synthesis kit (Bio-Rad, Hercules, Calif.) using manufacturer's recommended protocol for semi-quantitative PCR and real-time quantitative PCR (qRT-PCR). An amount of 1 μg of RNA is used in the 20 mL reaction mixture. For PCR and qRT-PCR, 2 μL of the diluted cDNA (1:20) is used in a 25 μL and 15 μL reaction mixture, respectively. PCR is carried out in 25 μL of a mixture containing Taq 2× Master Mix (New England Biolabs, Ipswich, Mass.). After heating the samples to 94° C. for 2 minutes, the reaction proceeded with 40 cycles of 94° C. for 30 seconds, 58° C. to amplify the PaWRKY3-like, PaWRKY71-like, and PaMYBS3-like in the above mentioned guayule lines for 30 seconds, and 68° C. for 1 minute. A final elongation step is carried out at 68° C. for 5 minutes. PCR products are separated by electrophoresis on a 1% (w/v) agarose gel; the expected PCR fragment is excised from the gel and purified with QIAquick® Gel Extraction Kit (Qiagen, Germantown, Md.) and sent to Elim Biopharmceuticals (Hayward, Calif.) for sequencing. In the qRT-PCR volume, 7.5 mL of iQ SYBR® Green Supermix is used (Bio-Rad, Hercules, Calif.). The qRT-PCR is run using the 7500 Fast Real-Time PCR system (Applied Biosystem, Waltham, Mass.) with the following thermal cycle: 95° C. pre-incubation for 3 minutes; amplification is performed for 40 cycles at 95° C. for 15 seconds and at 60° C. for 30 seconds; the dissociation stage is set for 95° C. for 15 seconds, at 60° C. for 1 minute, and at 95° C. for 15 seconds. Each qRT-PCR run is performed with three independent tissue samples, each sample having two technical replicates. The PaAos and 18S genes are used as internal controls. The primers used for each sequence, PCR annealing temperature, and the expected amplicon size are listed in FIG. 12. Crossing point value, which is the point at which the fluorescence crosses the threshold, and melting curve analyses are noted. The melting curve data are collected for all genes to ensure a single peak, indicating amplification of a specific region by a pair of primers. The relative expression values are calculated using the 2(−Delta C(T)) method (see Livak and Schmittgen (2001) supra). As seen in FIG. 13A-13C, the transcriptional expression of each of the three transcription factors (PaWRKY3-like, PaWRKY71-like, and PaMYBS3-like) increases by a factor of 2- to 10-fold, compared to empty vector (pND6) or non-altered controls (18S gene and PaAos). The expression of the PaAos and the content of AOS protein on rubber particles, are reduced for lines overexpressing these transcription factors. Rubber content in guayule overexpressing these three transcription factors is increased by a factor of 2- to 10-fold compared to empty vector or wild type controls.

Plasmids are prepared to overexpress PaWRKY3-like, PaWRKY71-like, and PaMYBS3-like in guayule. The cDNA sequence of each transcription factor is cloned into plasmid pND6 shown in FIG. 1 and replaces GUS. The primers used to generate and amplify PaWRKY3-like, PaWRKY71-like and PaMYBS3-like cDNAs are designed from the cDNA sequence obtained from guayule genome database assembly. The restriction enzymes AflII and BamHI are used for insertion of the the cDNAs into pND6 as described above in Example 1; thus primer pairs SEQ ID NOs: 27 and 28; 29 and 30; and 31 and 32, respectively are used to generate the cDNAs with the desired restrictions sequences. The PCR cycle program is 94° C. for 2 minutes (initial heating step) and PaWRKY3-like, PaWRKY71-like, and PaMYBS3-like are independently amplified at 40 cycles of 94° C. for 30 seconds (denaturation), 58° C. for 1 minute (annealing) and 68° C. for 1 minute (extension) and an additional 5 minutes extension at 68° C. The resulting amplicons are purified and subcloned into pGEM T Easy vector (Promega, Madison, Wis.) using the manufacturer's recommended protocol and sequenced to confirm the sequence of the plasmids. PaWRKY3-like genomic sequence is SEQ ID NO: 39 and coding sequence is SEQ ID NO: 40. PaWRKY71-like genomic sequence is SEQ ID NO: 41 and coding sequence is SEQ ID NO: 42. PaMYBS3-like genomic sequence is SEQ ID NO: 43 and coding sequence is SEQ ID NO: 44. The PaWRKY3-like, PaWRKY71-like, and PaMYBS3-like amplicons are digested with AflII and BamHI (Promega, Madison, Wis.) using the manufacturer's recommended protocol and are inserted into pPZP200 (Hajdukiewicz, et al. (1994)). As described above in Example 1, the PaWRKY3-like, PaWRKY71-like, and PaMYBS3-like amplicons replace GUS in pND6 to generate pND6-PaWRKY3-like, pND6-PaWRKY71-like, and pND6-PaMYBS3-like. Agrobacterium EHA101 competent cells are transformed with one of each of these plasmids using the protocol described above in Example 1.

The transformed Agrobacterium EHA101 harboring either pND6, pND6-PaWRKY3-like, pND6-PaWRKY71-like or pND6-PaMYBS3-like are used to transform guayule G7-11 using the protocols set forth above in Example 1. See, also, Dong, et al. (2006) and Dong, et al. (2013). The transformed cells in the leaf strips are induced to grow using the protocols set forth above in Example 1. The shoot tips of the rooted plantlets are maintained or planted, as described above in Example 1. While the genetically altered guayule are growing in tissue culture under selection, the genetically altered plants are screened for integration of the expression vectors, pND6-PaWRKY3-like, pND6-PaWRKY71-like and pND6-PaMYBS3-like using the protocol described above in Example 1.

PCR is performed in 50 μL mixture containing Taq 2× Master Mix (New England Biolabs, Ipswich, Mass.), 200 ng guayule genomic DNA or 20 pg plasmid DNA, and 100 ng of pND6-WRKY3-like, pND6-WRKY71-like and pND6-MYBS3-like specific primers; namely SEQ ID NOs: 33 and 34; 35 and 36; and 37 and 38; respectively, (see also FIG. 12) for guayule transformed with pND6-WRKY3-like, pND6-WRKY71-like and pND6-MYBS3-like. After heating the samples to 94° C. for 2 minutes, the reaction proceeds with 35 cycles of 94° C. for 30 seconds, 71° C. to amplify the DNA for 30 seconds, and 68° C. for 1 minute. A final elongation step is carried out at 68° C. for 5 minutes. PCR products are separated by electrophoresis on a 1% (w/v) agarose gel. The band for the overexpression lines are about 800 bp, about 550 bp and about 400 bp for pND6-WRKY3-like, pND6-WRKY71-like, and pND6-MYBS3-like, respectively. The genetically altered guayule plants harboring the empty plasmid (pND6 (negative control)) are confirmed by GUS staining using the protocol described above in Example 1.

Genetically altered guayule containing intact PaWRKY3-like, PaWRKY71-like, PaMYBS3-like, and genetically altered guayule containing the control plasmid (pND6) are further screened to determine the RNA level using the protocols described above in Example 2 and FIG. 12. Collection of tissues, extraction, clean-up and quantification of RNA and cDNA synthesis are performed using the protocols described above in Example 2. Genetically altered guayule lines that overexpress PaWRKY3-like, PaWRKY71-like, and PaMYBS3-like genes significantly more than controls are then selected for further analyses, as described below.

Genetically altered guayule lines that overexpress PaWRKY3-like, PaWRKY71-like, or PaMYBS3-like and non-altered guayule are grown as described in Example 3, above, and rubber content is assessed using the protocols described in Example 3, above. The average rubber content of the shoots of the genetically altered guayule lines for PaWRKY3-like, PaWRKY71-like, and PaMYBS3-like are determined as described above. The genetically altered guayule lines containing PaWRKY3-like, PaWRKY71-like, or PaMYBS3-like are transplanted into soil and grown in the conditions described above in Example 3. The average rubber content of the shoots and roots of the genetically altered guayule lines PaWRKY3-like, PaWRKY71-like, and PaMYBS3-like are determined as describe above. Next, the quality of the rubber produced by the genetically altered guayule lines containing PaWRKY3-like, PaWRKY71-like, or PaMYBS3-like are assess using the protocols described above in Example 7. For these experiments, the plant biomass, rubber content, and quality are similar to or higher than the PaAosiL genetically altered guayule described above.

The foregoing detailed description and certain representative embodiments and details of the invention have been presented for purposes of illustration and description of the invention. It is not intended to be exhaustive or to limit the invention to the precise forms disclosed. It will be apparent to practitioners skilled in the art that modifications and variations may be made therein without departing from the scope of the invention. All references cited herein are incorporated by reference.

We, the inventors, claim as follows:

1. An altered guayule, parts and progeny thereof, that produces more rubber than an amount of rubber produced by a non-altered guayule comprising an alteration that causes said altered guayule to produce an increased amount of rubber, said alteration being a reduction in an amount of functional PaAos produced by said altered guayule, wherein said alteration causes said altered guayule to produce more rubber than said amount of rubber produced by said non-altered guayule, wherein said reduction in an amount of functional PaAos produced by said altered guayule comprises one or more of the following:

(i) a genetic alteration in said altered guayule, said genetic alteration comprising an expression vector comprising a heterologous promoter operably linked to a polynucleotide encoding PaAos anti-sense RNA; wherein said polynucleotide encoding PaAos anti-sense RNA comprises a sequence that is the reverse complementary sequence of a PaAos gene, a sequence at least 95% identical thereof, a fragment of the reverse complementary sequence of a PaAos gene, or a sequence at least 95% identical thereof; and wherein said expression vector produces said PaAos anti-sense RNA, (ii) a genetic alteration in said altered guayule; wherein said genetic alteration comprises an expression vector comprising a heterologous promoter operably linked to a polynucleotide encoding a PaAos dsRNA; wherein said polynucleotide comprises at least 19 contiguous nucleotides of a PaAos sequence, or a fragment thereof, or a sequence at least 95% identical to the PaAos sequence, or a sequence at least 95% identical to the fragment of the PaAos sequence; and wherein said expression vector produces said PaAos dsRNA, and (iii) administering PaAos dsRNA to a guayule to generate said altered guayule; wherein said PaAos dsRNA comprises at least 19 contiguous nucleotides of a PaAos sequence, or a fragment thereof, or a sequence at least 95% identical to the PaAos sequence, or a sequence at least 95% identical to the fragment of the PaAos sequence; wherein said PaAos dsRNA enters said altered guayule and reduces said amount of functional PaAos produced by said altered guayule.

2. The altered guayule of claim 1; wherein said polynucleotide encoding PaAos anti-sense RNA comprises a sequence selected from the group consisting of:

(i) SEQ ID NO: 11,
(ii) a sequence at least 95% identical to SEQ ID NO: 11,
(iii) at least 19 contiguous nucleotides of SEQ ID NO: 11,
(iv) at least 19 contiguous nucleotides of reverse complementary sequence of a PaAos gene, and
(v) at least 19 contiguous nucleotides of a sequence that is at least 95% identical to reverse complementary sequence of a PaAos gene.

3. An altered guayule, parts and progeny thereof, that produces more rubber than an amount of rubber produced by a non-altered guayule comprising an alteration that causes said altered guayule to produce an increased amount of rubber, said alteration being an increase in an amount of a transcription factor produced by said altered guayule, wherein said alteration causes said altered guayule to produce more rubber than said amount of rubber produced by said non-altered guayule, wherein said increase in said amount of a transcription factor produced by said altered guayule comprises a genetic alteration in said altered guayule; wherein said genetic alteration comprises an expression vector comprising a heterologous promoter operably linked to a polynucleotide encoding at least one transcription factor selected from the group consisting of PaWRKY3-like, PaWRKY71-like, PaMYBS3-like, and a sequence at least 95% identical to any one of PaWRKY3-like, PaWRKY71-like, and PaMYBS3-like; and wherein said altered guayule produces said at least one transcription factor.

4. A germplasm of said altered guayule of any one of claims 1, 3, wherein said germplasm comprises said alteration.

5. A seed of said altered guayule of any one of claim 1, 3, wherein said seed comprises said alteration.

6. A method for increasing amount of rubber produced by an altered guayule compared to an amount of rubber produced by a non-altered guayule, said method comprising reducing an amount of functional PaAos produced by said altered guayule;

wherein said alterations cause said alteration causes said altered guayule to produce more rubber than said amount of rubber produced by said non-altered guayule, wherein said reducing an amount of functional PaAos produced by said altered guayule comprises one or more of the following:

(i) making a genetic alteration in said guayule; wherein said genetic alteration comprises an expression vector comprising a heterologous promoter operably linked to a polynucleotide encoding PaAos anti-sense RNA; wherein said polynucleotide encoding PaAos anti-sense RNA comprises a sequence that is the reverse complementary sequence of a PaAos gene, a sequence at least 95% identical thereof, a fragment of the reverse complementary sequence of a PaAos gene, or a sequence at least 95% identical thereof; and wherein said expression vector produces said PaAos anti-sense RNA;

(ii) making a genetic alteration in said guayule; wherein said genetic alteration comprises an expression vector comprising a heterologous promoter operably linked to a polynucleotide encoding a PaAos dsRNA; wherein said polynucleotide comprises at least 19 contiguous nucleotides of a PaAos sequence, or a fragment thereof, or a sequence at least 95% identical to the PaAos sequence, or a sequence at least 95% identical to the fragment of the PaAos sequence; and wherein said expression vector produces said PaAos dsRNA; and (iii) administering PaAos dsRNA to a guayule to generate said altered guayule; wherein said PaAos dsRNA comprises at least 19 contiguous nucleotides of a PaAos sequence, or a fragment thereof, or a sequence at least 95% identical to the PaAos sequence, or a sequence at least 95% identical to the fragment of the PaAos sequence; wherein said PaAos dsRNA enters said altered guayule and reduces said amount of functional PaAos produced by said altered guayule.

7. A method for increasing amount of rubber produced by an altered guayule compared to an amount of rubber produced by a non-altered guayule, said method comprising increasing amount of a transcription factor produced by said altered guayule;
  wherein said alteration causes said altered guayule to produce more rubber than said amount of rubber produced by said non-altered guayule,
  wherein said increasing said amount of a transcription factor produced by said altered guayule comprises making a genetic alteration in said guayule; wherein said genetic alteration comprises an expression vector comprising a heterologous promoter operably linked to a polynucleotide encoding at least one transcription factor selected from the group consisting of PaWRKY3-like, PaWRKY71-like, PaMYBS3-like and a sequence at least 95% identical to any one of PaWRKY3-like, PaWRKY71-like, and PaMYBS3-like; and wherein said altered guayule produces said at least one transcription factor.

8. The method of any one of claim 6, 7, further comprising exposing said altered guayule to between approximately 7° C. and approximately 15° C. for approximately 8 hours per day.

9. An altered guayule produced by the method of any one of claims 6, 7, wherein said altered guayule comprises said alteration and produces more rubber than the amount of rubber produced by a non-altered guayule.

10. An altered seed of an altered guayule produced by the method of any one of claims 6, 7, wherein said altered seed comprises said alteration.

* * * * *

```
                        SEQUENCE LISTING

<160> NUMBER OF SEQ ID NOS: 45

<210> SEQ ID NO 1
    <211> LENGTH: 34
    <212> TYPE: DNA
    <213> ORGANISM: Artificial Sequence
    <220> FEATURE:
    <223> OTHER INFORMATION: primer, chemical synthesis

<400> SEQUENCE: 1
cttaagaggt ggtatggacc catcgtctaa accc                                34

<210> SEQ ID NO 2
    <211> LENGTH: 29
    <212> TYPE: DNA
    <213> ORGANISM: Artificial Sequence
    <220> FEATURE:
    <223> OTHER INFORMATION: primer, chemical synthesis

<400> SEQUENCE: 2
ggatcctcat atactagctc tcttcaggg                                      29

<210> SEQ ID NO 3
    <211> LENGTH: 24
    <212> TYPE: DNA
    <213> ORGANISM: Artificial Sequence
    <220> FEATURE:
    <223> OTHER INFORMATION: primer, chemical synthesis

<400> SEQUENCE: 3
atgagcccag aacgacgccc ggcc                                           24

<210> SEQ ID NO 4
    <211> LENGTH: 24
    <212> TYPE: DNA
    <213> ORGANISM: Artificial Sequence
    <220> FEATURE:
    <223> OTHER INFORMATION: primer, chemical synthesis

<400> SEQUENCE: 4
gatctcggtg acgggcagga ccgg                                           24

<210> SEQ ID NO 5
    <211> LENGTH: 20
    <212> TYPE: DNA
    <213> ORGANISM: Artificial Sequence
    <220> FEATURE:
    <223> OTHER INFORMATION: primer, chemical synthesis
```

<400> SEQUENCE: 5
caacaaaccc cgacttctgg                                                  20

<210> SEQ ID NO 6
<211> LENGTH: 20
<212> TYPE: DNA
<213> ORGANISM: Artificial Sequence
<220> FEATURE:
<223> OTHER INFORMATION: primer, chemical synthesis

<400> SEQUENCE: 6
cacccgtcac caccatagta                                                  20

<210> SEQ ID NO 7
<211> LENGTH: 20
<212> TYPE: DNA
<213> ORGANISM: Artificial Sequence
<220> FEATURE:
<223> OTHER INFORMATION: primer, chemical synthesis

<400> SEQUENCE: 7
aacccggaag aaaccaaact                                                  20

<210> SEQ ID NO 8
<211> LENGTH: 20
<212> TYPE: DNA
<213> ORGANISM: Artificial Sequence
<220> FEATURE:
<223> OTHER INFORMATION: primer, chemical synthesis

<400> SEQUENCE: 8
cgcaaccgac tggaaataat                                                  20

<210> SEQ ID NO 9
<211> LENGTH: 1422
<212> TYPE: DNA
<213> ORGANISM: Parthenium argentatum

<400> SEQUENCE: 9
atggacccat cgtctaaacc cctccgtgaa atccccggct cttatggcat tcctttcttt      60
caaccgataa aagaccggtt ggagtatttt tacgggaccg gaggtcgaga cgagtacttc     120
cggtcccgca tgcaaaaata ccaatccacg gtatttcgag ccaacatgcc accgggccct     180
ttcgtaagca gcaacccgaa ggtaatcgtc ctactcgacg ccaaaagctt tccgatactc     240
tttgatgtat ccaaagtcga gaagaaagat ttgttcaccg aacttacat gccgtcaacc      300 aaactcactg gcggctatcg cgtactctcg tacctcgacc catccgaacc tagacatgct     360
caacttaaga acctcttgtt cttcatgctt aaaaattcaa gcaaccgagt cattcctcag     420
ttcgaaacca cttacaccga actctttgaa ggtcttgaag ccgagctagc caaaaacggg     480
aaagccgcgt tcaacgatgt tggtgaacaa gcggcttttcc ggttttttggg cagggcttat    540 tttaactcga acccggaaga aaccaaacta ggaactagtg cgcctacgtt aattagctcg     600
tgggtgttat ttaatcttgc ccccacgctc gacctcggac ttccgtggtt cttgcaggaa     660
cctcttctac acactttccg actgccggcg ttcctgatta agagtactta caacaaactt     720
tacgattatt ccagtcggt tgcgactccg gttatggaac aagcagaaaa attaggggtt      780
ccgaaggatg aagctgtgca caatatctta ttcgcggttt gcttcaatac ttttggtggt     840
gttaagatcc tcttcccgaa tacactcaaa tggatcggac ttgctggtga gaatttgcat     900

```
acccaattgg cggaagagat tagaggtgct ataaaatcat acggggacgg taacgtgacg      960
ctggaagcaa tcgagcagat gccgttgacg aagtcagtgg tgtacgagtc cctcaggatt     1020
gaaccaccag tgcctccgca atatggaaaa gccaaaagca actttaccat agagtcacac     1080
gacgccactt tcgaagtcaa aaaggagaa atgttattcg ggtaccaacc gtttgcaacc      1140
aaggacccaa aagtatttga ccgacctgag gaatatgtcc ctgatcggtt cgttggggat     1200
ggcgaggcat tgttgaagta cgtatggtgg tctaatgggc cggagacaga gagtccgaca     1260
gttgaaaata aacaatgtgc cggaaaagac tttgtcgtgc ttataacgag gttgtttgtc     1320
attgaacttt tccggcgata tgactctttt gaaatcgaat taggcgagtc tcctttgggt     1380
gcagctgtca cacttacgtt cctgaagaga gctagtatat ga                        1422
```

<210> SEQ ID NO 10
<211> LENGTH: 473
<212> TYPE: PRT
<213> ORGANISM: Parthenium argentatum

<400> SEQUENCE: 10

```
Met Asp Pro Ser Ser Lys Pro Leu Arg Glu Ile Pro Gly Ser Tyr Gly
1               5                   10                  15

Ile Pro Phe Phe Gln Pro Ile Lys Asp Arg Leu Glu Tyr Phe Tyr Gly
            20                  25                  30

Thr Gly Gly Arg Asp Glu Tyr Phe Arg Ser Arg Met Gln Lys Tyr Gln
        35                  40                  45

Ser Thr Val Phe Arg Ala Asn Met Pro Pro Gly Pro Phe Val Ser Ser
    50                  55                  60

Asn Pro Lys Val Ile Val Leu Leu Asp Ala Lys Ser Phe Pro Ile Leu
65                  70                  75                  80

Phe Asp Val Ser Lys Val Glu Lys Lys Asp Leu Phe Thr Gly Thr Tyr
                85                  90                  95

Met Pro Ser Thr Lys Leu Thr Gly Gly Tyr Arg Val Leu Ser Tyr Leu
            100                 105                 110

Asp Pro Ser Glu Pro Arg His Ala Gln Leu Lys Asn Leu Leu Phe Phe
        115                 120                 125

Met Leu Lys Asn Ser Ser Asn Arg Val Ile Pro Gln Phe Glu Thr Thr
    130                 135                 140

Tyr Thr Glu Leu Phe Glu Gly Leu Glu Ala Glu Leu Ala Lys Asn Gly
145                 150                 155                 160

Lys Ala Ala Phe Asn Asp Val Gly Glu Gln Ala Ala Phe Arg Phe Leu
                165                 170                 175

Gly Arg Ala Tyr Phe Asn Ser Asn Pro Glu Glu Thr Lys Leu Gly Thr
            180                 185                 190

Ser Ala Pro Thr Leu Ile Ser Ser Trp Val Leu Phe Asn Leu Ala Pro
        195                 200                 205

Thr Leu Asp Leu Gly Leu Pro Trp Phe Leu Gln Glu Pro Leu Leu His
    210                 215                 220

Thr Phe Arg Leu Pro Ala Phe Leu Ile Lys Ser Thr Tyr Asn Lys Leu
225                 230                 235                 240

Tyr Asp Tyr Phe Gln Ser Val Ala Thr Pro Val Met Glu Gln Ala Glu
                245                 250                 255

Lys Leu Gly Val Pro Lys Asp Glu Ala Val His Asn Ile Leu Phe Ala
            260                 265                 270

Val Cys Phe Asn Thr Phe Gly Gly Val Lys Ile Leu Phe Pro Asn Thr
        275                 280                 285
```

```
Leu Lys Trp Ile Gly Leu Ala Gly Glu Asn Leu His Thr Gln Leu Ala
    290                 295                 300
Glu Glu Ile Arg Gly Ala Ile Lys Ser Tyr Gly Asp Gly Asn Val Thr
305                 310                 315                 320
Leu Glu Ala Ile Glu Gln Met Pro Leu Thr Lys Ser Val Val Tyr Glu
                325                 330                 335
Ser Leu Arg Ile Glu Pro Pro Val Pro Gln Tyr Gly Lys Ala Lys
            340                 345                 350
Ser Asn Phe Thr Ile Glu Ser His Asp Ala Thr Phe Glu Val Lys Lys
        355                 360                 365
Gly Glu Met Leu Phe Gly Tyr Gln Pro Phe Ala Thr Lys Asp Pro Lys
370                 375                 380
Val Phe Asp Arg Pro Glu Glu Tyr Val Pro Asp Arg Phe Val Gly Asp
385                 390                 395                 400
Gly Glu Ala Leu Leu Lys Tyr Val Trp Trp Ser Asn Gly Pro Glu Thr
                405                 410                 415
Glu Ser Pro Thr Val Glu Asn Lys Gln Cys Ala Gly Lys Asp Phe Val
            420                 425                 430
Val Leu Ile Thr Arg Leu Phe Val Ile Glu Leu Phe Arg Arg Tyr Asp
        435                 440                 445
Ser Phe Glu Ile Glu Leu Gly Glu Ser Pro Leu Gly Ala Ala Val Thr
450                 455                 460
Leu Thr Phe Leu Lys Arg Ala Ser Ile
465                 470

<210> SEQ ID NO 11
<211> LENGTH: 313
<212> TYPE: DNA
<213> ORGANISM: Parthenium argentatum

<400> SEQUENCE: 11
cgccggaaaa gttcaatcac aaacaacctc gttataagca cggcaaagtc tttccggca       60 cattgtttat tttcaactga tcggactctc tgtctccggc ccattagacc accatacgta     120
cttcaacaat gcctcgccat ccccaacgag ccgatcaggg acatattcct caggtcggtc     180 aaatacttt gggtccttgg ttgcaaacgg ttggtacccg aataacattt ctcctttttt     240
gacttcgaaa gtggcgtcgt gtgactctat ggtaaagttg cttttggctt ttccatattg     300
cggaggcact ggt                                                       313

<210> SEQ ID NO 12
<211> LENGTH: 1422
<212> TYPE: DNA
<213> ORGANISM: Parthenium argentatum

<400> SEQUENCE: 12
atggacccat cgtctaaacc cctccgtgaa atccccggct cttatggcat tcctttcttt       60
caaccgataa aagaccgatt ggagtatttt tacgggaccg gaggtcgaga cgagtacttc     120
cggtcccgca tgcaaaaata ccaatccacg gtatttcgag ccaacatgcc accgggccct     180
ttcgtaagca gcaacccgaa ggtcatcgtc tactcgacg ccaagagctt ccgatactc      240 tttgatgtat ccaaagtcga gaagaaagat tgttcaccg aacttacat gccgtcaacc     300 aaactcactg gcggctaccg cgtactctcg tacctcgacc catccgaacc tagacatgct     360
cagctgaaga acctcttgtt cttcatgctt aaaaattcaa gcaaccgagt cattcctcag     420
```

```
ttcgaaacca cttacaccga actctttgaa ggtcttgaag ccgagctagc caaaaacggg      480
aaagccgcgt tcaacgatgt tggtgaacaa gcggctttcc ggttttgggg cagggcttat      540
tttaactcga acccggaaga aaccaaacta ggaactagtg cgcctacgtt aattagctcg      600
tgggtgttat ttaatcttgc ccccacgctc gacctcggac ttccgtggtt cttgcaggaa      660
cctcttctac acactttccg actgccggcg ttcctgatta agagtactta caacaaactt      720
tacgattatt ccagtcggt tgcgactccg gttatggaac aagcagaaaa attaggggtt       780
ccgaaggatg aagctgtgca caatatctta ttcgcggttt gcttcaatac ttttggtggt      840
gtaaagatcc tcttcccgaa tacactcaaa tggatcggac ttgctggtga aatttgcat       900
acccaattgg cggaagagat tagaggtgct ataaaatcat acggggacgg tgacgtgacg      960
ctggaagcaa tcgagcagat gccgttgacg aagtcagtgg tgtacgagtc cctcaggatt     1020
gaaccaccag tgcctccgca atatggaaaa gccaaaagca actttaccat agagtcacac     1080
gacgccactt tcgaagtcaa aaaggagaa atgttattcg ggtaccaacc gtttgcaacc      1140
aaggacccaa agtatttga ccgacccgag gaatatgtcc ctgatcggtt cgttggggat      1200
ggcgaggcat tgttgaagta catatggtgg tctaatgggc cggagacaga gagtccgaca     1260
gttgaaaata aacaatgtgc cggaaaagac tttgttgtgc ttataacgag gttgtttgtc     1320
attgaacttt ccggcgata tgactccttt gaaatcgaat taggcgagtc tcctttgggt      1380
gcagctgtca cacttacgtc cctgaagaga gctagtatat ga                        1422
```

<210> SEQ ID NO 13
<211> LENGTH: 473
<212> TYPE: PRT
<213> ORGANISM: Parthenium argentatum

<400> SEQUENCE: 13

```
Met Asp Pro Ser Ser Lys Pro Leu Arg Glu Ile Pro Gly Ser Tyr Gly
1               5                   10                  15

Ile Pro Phe Phe Gln Pro Ile Lys Asp Arg Leu Glu Tyr Phe Tyr Gly
                20                  25                  30

Thr Gly Gly Arg Asp Glu Tyr Phe Arg Ser Arg Met Gln Lys Tyr Gln
        35                  40                  45

Ser Thr Val Phe Arg Ala Asn Met Pro Pro Gly Pro Phe Val Ser Ser
    50                  55                  60

Asn Pro Lys Val Ile Val Leu Leu Asp Ala Lys Ser Phe Pro Ile Leu
65                  70                  75                  80

Phe Asp Val Ser Lys Val Glu Lys Lys Asp Leu Phe Thr Gly Thr Tyr
                85                  90                  95

Met Pro Ser Thr Lys Leu Thr Gly Gly Tyr Arg Val Leu Ser Tyr Leu
            100                 105                 110

Asp Pro Ser Glu Pro Arg His Ala Gln Leu Lys Asn Leu Leu Phe Phe
        115                 120                 125

Met Leu Lys Asn Ser Ser Asn Arg Val Ile Pro Gln Phe Glu Thr Thr
    130                 135                 140

Tyr Thr Glu Leu Phe Glu Gly Leu Glu Ala Glu Leu Ala Lys Asn Gly
145                 150                 155                 160

Lys Ala Ala Phe Asn Asp Val Gly Glu Gln Ala Phe Arg Phe Leu
                165                 170                 175

Gly Arg Ala Tyr Phe Asn Ser Asn Pro Glu Glu Thr Lys Leu Gly Thr
            180                 185                 190

Ser Ala Pro Thr Leu Ile Ser Ser Trp Val Leu Phe Asn Leu Ala Pro
```

```
        195                 200                 205

Thr Leu Asp Leu Gly Leu Pro Trp Phe Leu Gln Glu Pro Leu Leu His
    210                 215                 220
Thr Phe Arg Leu Pro Ala Phe Leu Ile Lys Ser Thr Tyr Asn Lys Leu
225                 230                 235                 240
Tyr Asp Tyr Phe Gln Ser Val Ala Thr Pro Val Met Glu Gln Ala Glu
                245                 250                 255
Lys Leu Gly Val Pro Lys Asp Glu Ala Val His Asn Ile Leu Phe Ala
            260                 265                 270

Val Cys Phe Asn Thr Phe Gly Gly Val Lys Ile Leu Phe Pro Asn Thr
        275                 280                 285

Leu Lys Trp Ile Gly Leu Ala Gly Glu Asn Leu His Thr Gln Leu Ala
    290                 295                 300
Glu Glu Ile Arg Gly Ala Ile Lys Ser Tyr Gly Asp Gly Asp Val Thr
305                 310                 315                 320
Leu Glu Ala Ile Glu Gln Met Pro Leu Thr Lys Ser Val Val Tyr Glu
                325                 330                 335
Ser Leu Arg Ile Glu Pro Pro Val Pro Pro Gln Tyr Gly Lys Ala Lys
            340                 345                 350
Ser Asn Phe Thr Ile Glu Ser His Asp Ala Thr Phe Glu Val Lys Lys
        355                 360                 365

Gly Glu Met Leu Phe Gly Tyr Gln Pro Phe Ala Thr Lys Asp Pro Lys
    370                 375                 380
Val Phe Asp Arg Pro Glu Glu Tyr Val Pro Asp Arg Phe Val Gly Asp
385                 390                 395                 400
Gly Glu Ala Leu Leu Lys Tyr Ile Trp Trp Ser Asn Gly Pro Glu Thr
                405                 410                 415
Glu Ser Pro Thr Val Glu Asn Lys Gln Cys Ala Gly Lys Asp Phe Val
            420                 425                 430
Val Leu Ile Thr Arg Leu Phe Val Ile Glu Leu Phe Arg Arg Tyr Asp
        435                 440                 445

Ser Phe Glu Ile Glu Leu Gly Glu Ser Pro Leu Gly Ala Ala Val Thr
    450                 455                 460
Leu Thr Ser Leu Lys Arg Ala Ser Ile
465                 470

<210> SEQ ID NO 14
<211> LENGTH: 1422
<212> TYPE: DNA
<213> ORGANISM: Parthenium argentatum

<400> SEQUENCE: 14
atggacccat cgtctaaacc cctccgtgaa atccccggct cttatggcat tcctttcttt      60
caaccgataa aagaccgatt ggagtatttt tacgggaccg gaggtcgaga cgagtacttc     120
cggtcccgca tgcaaaaata ccaatccacg gtatttcgag ccaacatgcc accgggccct     180
ttcgtaagca gcaacccgaa ggtcatcgtc ctactcgacg ccaaaagctt tccgatactc     240
tttgatgtat ccaaagtcga gaagaaagat ttgttcaccg gaacttacat gccgtcaacc     300
aaactcactg gcggctaccg cgtactctcg tacctcgacc catccgaacc tagacatgct     360
caacttaaga acctcttgtt cttcatgctt aaaaattcaa gcaaccgagt cattcctcag     420
ttcgaaacca cttacaccga actctttgaa ggtcttgaag ccgagctagc caaaaacggg     480
aaagccgcgt tcaacgatgt tggtgaacaa gcggctttcc ggtttttggg cagggcttat     540
```

```
tttaactcga acccggaaga aaccaaacta ggaactagtg cgcctacgtt aattagctcg    600
tgggtgttat ttaatcttgc ccccacgctc gacctcggac ttccgtggtt cttgcaggaa    660
cctcttctac acactttccg actgccggcg ttcctgatta agagtactta caacaaactt    720
tacgattatt ccagtcggt tgcgactccg gttatggaac aagcagaaaa attaggggtt     780
ccgaaggatg aagctgtgca caatatctta ttcgcggttt gcttcaatac ttttggtggt    840
gttaagatcc tcttcccgaa tacactcaaa tggatcggac ttgctggtga aatttgcat    900 acccaattgg cggaagagat tagaggtgct ataaaatcat acggggacgg taacgtgacg    960
ctggaagcaa tcgagcagat gccgttgacg aagtcagtgg tgtacgagtc cctcaggatt   1020
gaaccaccag tgcctccgca atatggaaaa gccaaaagca actttaccat agagtcacac   1080
gacgccactt tcgaagtcaa aaaggagaa atgttattcg ggtaccaacc gtttgcaacc    1140
aaggacccaa aagtatttga ccgacctgag gaatatgtcc ctgatcggtt cgttggggat   1200
ggcgaggcat tgttgaagta cgtatggtgg tctaatgggc cggagacaga gagtccgaca   1260
gttgaaaata acaatgtgc cggaaaagac tttgtcgtgc ttataacgag gttgtttgtc    1320
attgaacttt tccggcgata tgactctttt gaaatcgaat taggcgagtc tccttggggt   1380
gcagctgtca cacttacgtc cctgaagaga gctagtatat ga                      1422
```

<210> SEQ ID NO 15
<211> LENGTH: 473
<212> TYPE: PRT
<213> ORGANISM: Parthenium argentatum

<400> SEQUENCE: 15

```
Met Asp Pro Ser Ser Lys Pro Leu Arg Glu Ile Pro Gly Ser Tyr Gly
1               5                   10                  15

Ile Pro Phe Phe Gln Pro Ile Lys Asp Arg Leu Glu Tyr Phe Tyr Gly
                20                  25                  30

Thr Gly Gly Arg Asp Glu Tyr Phe Arg Ser Arg Met Gln Lys Tyr Gln
            35                  40                  45

Ser Thr Val Phe Arg Ala Asn Met Pro Pro Gly Pro Phe Val Ser Ser
        50                  55                  60

Asn Pro Lys Val Ile Val Leu Leu Asp Ala Lys Ser Phe Pro Ile Leu
65                  70                  75                  80

Phe Asp Val Ser Lys Val Glu Lys Lys Asp Leu Phe Thr Gly Thr Tyr
                85                  90                  95

Met Pro Ser Thr Lys Leu Thr Gly Gly Tyr Arg Val Leu Ser Tyr Leu
            100                 105                 110

Asp Pro Ser Glu Pro Arg His Ala Gln Leu Lys Asn Leu Leu Phe Phe
        115                 120                 125

Met Leu Lys Asn Ser Ser Asn Arg Val Ile Pro Gln Phe Glu Thr Thr
    130                 135                 140

Tyr Thr Glu Leu Phe Glu Gly Leu Glu Ala Glu Leu Ala Lys Asn Gly
145                 150                 155                 160

Lys Ala Ala Phe Asn Asp Val Gly Glu Gln Ala Ala Phe Arg Phe Leu
                165                 170                 175

Gly Arg Ala Tyr Phe Asn Ser Asn Pro Glu Thr Lys Leu Gly Thr
            180                 185                 190

Ser Ala Pro Thr Leu Ile Ser Ser Trp Val Leu Phe Asn Leu Ala Pro
        195                 200                 205

Thr Leu Asp Leu Gly Leu Pro Trp Phe Leu Gln Glu Pro Leu Leu His
    210                 215                 220
```

```
Thr Phe Arg Leu Pro Ala Phe Leu Ile Lys Ser Thr Tyr Asn Lys Leu
225                 230                 235                 240

Tyr Asp Tyr Phe Gln Ser Val Ala Thr Pro Val Met Glu Gln Ala Glu
            245                 250                 255

Lys Leu Gly Val Pro Lys Asp Glu Ala Val His Asn Ile Leu Phe Ala
        260                 265                 270

Val Cys Phe Asn Thr Phe Gly Gly Val Lys Ile Leu Phe Pro Asn Thr
    275                 280                 285

Leu Lys Trp Ile Gly Leu Ala Gly Glu Asn Leu His Thr Gln Leu Ala
290                 295                 300

Glu Glu Ile Arg Gly Ala Ile Lys Ser Tyr Gly Asp Gly Asn Val Thr
305                 310                 315                 320

Leu Glu Ala Ile Glu Gln Met Pro Leu Thr Lys Ser Val Val Tyr Glu
            325                 330                 335

Ser Leu Arg Ile Glu Pro Pro Val Pro Pro Gln Tyr Gly Lys Ala Lys
        340                 345                 350

Ser Asn Phe Thr Ile Glu Ser His Asp Ala Thr Phe Glu Val Lys Lys
    355                 360                 365

Gly Glu Met Leu Phe Gly Tyr Gln Pro Phe Ala Thr Lys Asp Pro Lys
370                 375                 380

Val Phe Asp Arg Pro Glu Glu Tyr Val Pro Asp Arg Phe Val Gly Asp
385                 390                 395                 400

Gly Glu Ala Leu Leu Lys Tyr Val Trp Trp Ser Asn Gly Pro Glu Thr
            405                 410                 415

Glu Ser Pro Thr Val Glu Asn Lys Gln Cys Ala Gly Lys Asp Phe Val
        420                 425                 430

Val Leu Ile Thr Arg Leu Phe Val Ile Glu Leu Phe Arg Arg Tyr Asp
    435                 440                 445

Ser Phe Glu Ile Glu Leu Gly Glu Ser Pro Trp Gly Ala Ala Val Thr
450                 455                 460

Leu Thr Ser Leu Lys Arg Ala Ser Ile
465                 470

<210> SEQ ID NO 16
<211> LENGTH: 21
<212> TYPE: DNA
<213> ORGANISM: Parthenium argentatum

<400> SEQUENCE: 16
atggacccat cgtctaaacc c                                           21

<210> SEQ ID NO 17
<211> LENGTH: 22
<212> TYPE: DNA
<213> ORGANISM: Parthenium argentatum

<400> SEQUENCE: 17
tcatatacta gctctcttca gg                                          22

<210> SEQ ID NO 18
<211> LENGTH: 2564
<212> TYPE: DNA
<213> ORGANISM: Parthenium argentatum

<400> SEQUENCE: 18
aatccagcta agtctaactt gttaatattc aactaaggta aattagttta tgtttgtagg    60
```

```
aaagtaacat aaatttgccg ggtgtcacat cttatgtccg attaacccct tactcaaccc    120
aatactatag ccattgataa ccttatctaa tctccttcct gtaattgtca ttcattgaac    180
atgaaacacg gatctatttt cattctcatg ttgttcaatt attcttttct cgttatatga    240
ttcaaagagg tcaaacttct ctaagtttga gtgtggccac gcatttacac cagtttggat    300
caacgagggt cccagaatac acaacttttt tataataaag aagaacagaa ttcctttgac    360
aacatacaac tcccacttaa ccttaggtat gctcccaacc aaatacccctt attgttgtct    420 tttcacgata cagtgttagg aaagattaaa gaacaaactt taggcaaatg ttagttccaa    480
tatgtctctc agttcaaagg acatttagat catatcaatt tcaaaatatc acatgacttt    540
gatctttaga gatcatttag aaacgagtta cgtcaaatat cattctctaa tgtatatcag    600
tgaacttggc cctcaacacc tttagatttc atctcatgaa caaacaatca ctcacaatag    660
tcataattcg aattgattcc cttgaattcg attgactacg gacattttga atacttttat    720
tcatgtatac ttaaacgtac aaaaattgaa catagcaaca caatttataa tgcattcaac    780
ctttaaatta aaataaagaa atgtagctat caattgttca aagcaccaaa tactaataga    840
tcaaaccact ctctagcatt ccttaacccct atacgaggcg tataggtaca aaccaatgca    900
cttattatgc agacatggga aattgtgaac gtaacacgac ttgtataggg caatacgaga    960
tgtatctggg gcgtgtaaat aacgattgag ggtgtggaaa tattatggcc cttaaattta   1020
agggatattc attgcctata aattatcgca aagcgggtat atattaaata cttttctata   1080
ttgtacccat cactatatat atatatatat atatatatat atatatatat atatatatat   1140
ataacctaca tgaaaatata taagcaggtt atcttttaaa ttttataaaa ctgcttcaaa   1200
attcaggcat acgagcataa cgaaacttta taagatttat gtatgatttc ataacgaatc   1260
tctatcaaaa acatattcaa tcaagacaat gtgtagcata tgggttaatt acatgcacat   1320
acacttcttc ataacattaa aaatttaaat ttaatattat tttataatgc gtgtacaaat   1380
caaacattgt tttaagttct tttatagcaa ctgtcacgtt taaaatttgc tcaccgtaat   1440
cagtaggaaa atattaaaag attataaaaa cgaagtaaac aatgtataaa aaaataaaaa   1500
gactagaacc taagggccgt cagctcgtct ttatatacag tagttcattc atccaaatac   1560
gcacaccatt ttctcacact caacattttc tcacacaaac atggatccat catctgaagc   1620
ccctcctcgt gaaatccctg gttcatacgg cattcctttt atccaaccga tcaaagaccg   1680
gttggagtat ttttacggga ccggaggccc agatgggttc ttccagtccc gcgttcaaaa   1740
ataccaatcc actgtgttcc gaaccaatat gccacccggc ccttttataa gcagcaaccc   1800
aaaagtcatt gtcctcttag acgccaaaag ctttcccgta ttgtttgatg tttctaaagt   1860
cgagaagaaa gatttattta ccggaactta tatgccgtca actaacctca ctggcggcta   1920
ccgcgtactc tcgtacatcg acccatccga acctagacat gctcaactta agaacctctt   1980
gttcttcatg cttaaaaatt caagcaaccg agtcattcct cagttccaaa caacttacac   2040
cgaactcttt gaaggtcttg aaaccgaatt ggccaaaaat gggaaagccg cgttcaacga   2100
cgttggtgaa caagcggctt tccggttttt gggccgggct tatttcaact ctaacccgga   2160
agaaaccaaa ctaggaacta gtgcgccgaa gttaattacc acgtgggtgt tgttcaatct   2220
tagcccgata ggcactgctg gacttccgtg gttcttggag gaccctctta tccacacttt   2280
ccgactgccg tcgtttctgg taaagagtaa ctacaacaag ctttacgatt attttgagtc   2340
ggctgcgact caggttgtgg agcaagcaga aatattaggg gttccgaaag atgaagcttt   2400
gcacaatatc ttattcgcgg tttgcttcaa tactttgaa aatacgcaaa caaagtaaaa   2460
```

```
aataaaaata aagaaccta aggtacatcc tcgtctatat atacacttgt ttttattcat    2520
ccaaaataaa cacaccatct tctcacactc aaaacagtca aaac                    2564

<210> SEQ ID NO 19
<211> LENGTH: 20
<212> TYPE: DNA
<213> ORGANISM: Artificial Sequence
<220> FEATURE:
<223> OTHER INFORMATION: chemical synthesized

<400> SEQUENCE: 19
aaccgcagtc tacacgaaga                                                 20

<210> SEQ ID NO 20
<211> LENGTH: 20
<212> TYPE: DNA
<213> ORGANISM: Artificial Sequence
<220> FEATURE:
<223> OTHER INFORMATION: chemical synthesized

<400> SEQUENCE: 20
tcgaagaatt atccggcgtg                                                 20

<210> SEQ ID NO 21
<211> LENGTH: 20
<212> TYPE: DNA
<213> ORGANISM: Artificial Sequence
<220> FEATURE:
<223> OTHER INFORMATION: chemical synthesized

<400> SEQUENCE: 21
tgtggcttgt ggagtgaaga                                                 20

<210> SEQ ID NO 22
<211> LENGTH: 20
<212> TYPE: DNA
<213> ORGANISM: Artificial Sequence
<220> FEATURE:
<223> OTHER INFORMATION: chemical synthesized

<400> SEQUENCE: 22
accaccactg aaaccaccat                                                 20

<210> SEQ ID NO 23
<211> LENGTH: 20
<212> TYPE: DNA
<213> ORGANISM: Artificial Sequence
<220> FEATURE:
<223> OTHER INFORMATION: chemical synthesized

<400> SEQUENCE: 23
cttggtccga agacgaacat                                                 20

<210> SEQ ID NO 24
<211> LENGTH: 20
<212> TYPE: DNA
<213> ORGANISM: Artificial Sequence
<220> FEATURE:
<223> OTHER INFORMATION: chemical synthesized

<400> SEQUENCE: 24
ggcttgaacg acgtttcttc                                                 20

<210> SEQ ID NO 25
```

```
<211> LENGTH: 20
<212> TYPE: DNA
<213> ORGANISM: Artificial Sequence
<220> FEATURE:
<223> OTHER INFORMATION: chemical synthesized

<400> SEQUENCE: 25
ccgtcccaag cagttacaat                                                    20

<210> SEQ ID NO 26
<211> LENGTH: 20
<212> TYPE: DNA
<213> ORGANISM: Artificial Sequence
<220> FEATURE:
<223> OTHER INFORMATION: chemical synthesized

<400> SEQUENCE: 26
tacgtgttca gtggttccca                                                    20

<210> SEQ ID NO 27
<211> LENGTH: 29
<212> TYPE: DNA
<213> ORGANISM: Artificial Sequence
<220> FEATURE:
<223> OTHER INFORMATION: chemical synthesized

<400> SEQUENCE: 27
cttaagatgt ctgcacaatc ttttcagag                                          29

<210> SEQ ID NO 28
<211> LENGTH: 32
<212> TYPE: DNA
<213> ORGANISM: Artificial Sequence
<220> FEATURE:
<223> OTHER INFORMATION: chemical synthesized

<400> SEQUENCE: 28
ggatccttaa caaaaagcac aaaaagaaaa ac                                      32

<210> SEQ ID NO 29
<211> LENGTH: 33
<212> TYPE: DNA
<213> ORGANISM: Artificial Sequence
<220> FEATURE:
<223> OTHER INFORMATION: chemical synthesized

<400> SEQUENCE: 29
cttaagatgt taaagattga accaattttt gtt                                     33

<210> SEQ ID NO 30
<211> LENGTH: 28
<212> TYPE: DNA
<213> ORGANISM: Artificial Sequence
<220> FEATURE:
<223> OTHER INFORMATION: chemical synthesized

<400> SEQUENCE: 30
ggatccttag ttctgttctt ctttgggc                                           28

<210> SEQ ID NO 31
<211> LENGTH: 28
<212> TYPE: DNA
<213> ORGANISM: Artificial Sequence
<220> FEATURE:
<223> OTHER INFORMATION: chemical synthesized

<400> SEQUENCE: 31
```
cttaagatgg taacatatag gaggggtt                                    28

<210> SEQ ID NO 32
<211> LENGTH: 31
<212> TYPE: DNA
<213> ORGANISM: Artificial Sequence
<220> FEATURE:
<223> OTHER INFORMATION: chemical synthesized

<400> SEQUENCE: 32
ggatccttat gggttgtacc ttgctttaaa a                                31

<210> SEQ ID NO 33
<211> LENGTH: 21
<212> TYPE: DNA
<213> ORGANISM: Artificial Sequence
<220> FEATURE:
<223> OTHER INFORMATION: chemical synthesized

<400> SEQUENCE: 33
cttaagaggt ggtatgtctg c                                           21

<210> SEQ ID NO 34
<211> LENGTH: 26
<212> TYPE: DNA
<213> ORGANISM: Artificial Sequence
<220> FEATURE:
<223> OTHER INFORMATION: chemical synthesized

<400> SEQUENCE: 34
ttaacaaaaa gcacaaaaag aaaaac                                      26

<210> SEQ ID NO 35
<211> LENGTH: 23
<212> TYPE: DNA
<213> ORGANISM: Artificial Sequence
<220> FEATURE:
<223> OTHER INFORMATION: chemical synthesized

<400> SEQUENCE: 35
cttaagaggt ggtatgttaa aga                                         23

<210> SEQ ID NO 36
<211> LENGTH: 22
<212> TYPE: DNA
<213> ORGANISM: Artificial Sequence
<220> FEATURE:
<223> OTHER INFORMATION: chemical synthesized

<400> SEQUENCE: 36
ttagttctgt tcttctttgg gc                                          22

<210> SEQ ID NO 37
<211> LENGTH: 21
<212> TYPE: DNA
<213> ORGANISM: Artificial Sequence
<220> FEATURE:
<223> OTHER INFORMATION: chemical synthesized

<400> SEQUENCE: 37
cttaagaggt ggtatggtaa c                                           21

<210> SEQ ID NO 38
<211> LENGTH: 25
<212> TYPE: DNA

<213> ORGANISM: Artificial Sequence
<220> FEATURE:
<223> OTHER INFORMATION: chemical synthesized

<400> SEQUENCE: 38 ttatggggttg taccttgctt taaaa        25

<210> SEQ ID NO 39
<211> LENGTH: 4884
<212> TYPE: DNA
<213> ORGANISM: Parthenium argentatum

<400> SEQUENCE: 39

```
gggttcttgt tgttttgatg tgtagttact aataagccct ttatttttgc tgttagaatt      60
cagatctttt ttttttttt taggaatccc atttggttgg attgttttta ggtttagatt     120
ttgatataca aaaaaaaaat aatgtaaata taatttatg ttttgaataa atgtggtctg     180
ctcatttcat ttgagtgatt ggtttaatga tttttgttg attgtttgcc aaaagtggaa     240
atctttaggt ttatttttg ttattctgta aacattgttt ttgtgcatag aatctttttg     300
ttttgcctaa aatgaccaaa tgtttatgat atcataactg cattcttagt ttttactata     360
tttattactg aaaagatata tttttttttg tagttgaagt ggctgatatt caagaattaa     420
gagagaagca ctggcatttg atgggtggtt ttactttttaa tgagcatggt gggataattg     480
gagattggat gccacctagc ccaagcccac gttcttttatt cgcagctgtg ttgggtgatg     540
aaatggggtc acgtcgggg tgtgggtccg agtctgaaaa gtttgagacc ggtaatgatg     600
gtgtgttcac ctttcctggg ccagataggc tcattgggtc ggaacacggt gagggtactc     660
aaagggaga tatagttgat ccagtggcgg aaccgggtga atttagagac cagaaagcgg     720
gcccgcgggc tggtcttgtt gaaaggatgg cagctagaac tggtcataat gctcctcggt     780
tggatactga ttttattaag cctgtgtatg gttcccaaaa ccaacaaact cagtcaccgt     840
acttgactgt gtcacctggt ctcagcccgg gttcttttct ggaatcacct gttttctgt     900
caaactcact ggtaagcgcg atagaacttt tttttttat aacatttaga gttatatata     960
tgacgtgcag ttgtttggat gtgtgttttg aagtgatttt gtgatattga gttgttggaa    1020
tatcacgttt aggtatatta ataattactt ttgaaggtgt cttgagggtt tggcaaaattc    1080
tgattgttta gtaacaaatt aactaagagt gtgctagtca ttttactcta atatctattg    1140
ataatcagtt atattttcga ctagtatcaa actgataatt taatcacttt cagtatgcac    1200
atgcaaacac ccccttaatg ccatgtttat gcaatccttt ttgttcgtgt tttcgggttc    1260
tcaattatat ttggaaatgt ttgataatga atagttgttt ggaggttttt gtgtgttata    1320
ataatgccaa atggtctcga ttggttctta tgtaggttca accttctcca acaactggga    1380
aattgcaatt tgctccaaat ggcaacagta ttgataacat gagtaaagat aacttctttg    1440
aggattctaa taacatttcc tttgccttta aaccctttcct agattcggct cctatatcct    1500
ctgaccatgt aagcaaagta acatacattt ataatttta tcttatattt tgtgtaaggg    1560
tggtgagttc aacacatttg cttgtacatg tgtccatttg ggctgtgttt tatctcaaac    1620
gggtcaaata aaaaaaaaac taaaaaggta agggtgaagt aggctgaaag tcaacctact    1680
tttatttgaa ggtatatgtt agtattttaa tacatgttgc tttccattca taattaacac    1740
actatttttt cgtgaaaacg gacaaaaagg gtttgtgggt caaaccggtc tgttttgatc    1800
cgtattaaga tgacctgctt ttacccgaag tcatttgact tgttaactat attttatgta    1860
ttaagtttct tagatacatt atcctctttta tagtcttcaa ctgctgatgc tgtttcctct    1920
```

```
ccgattattt aggtcaatgt caatccacct tttatgtctg cacaatcttt tcagagtaat    1980
gaagctttta cccaacctga ggaacaattt cagcctcaaa agagtgaacc ggcccaaatt    2040
tactcagact ttactgaaag gaagaacttt tcgctacaaa tggctccatt tgaagctcgt    2100
aatggcaatt ctgatctgac tcaacagcat catgataaac atcacgatga gattgacgca    2160
gatcagagta taaatggaga tattactaat gctagcagtg catcatctga tgatgggtat    2220
aattggagaa aatatggaca gaaacaagta aaaggaagtg agtatcctag aagctattat    2280
aaatgcactc acccaaattg tactgttaaa aagaaagtcg agcgttcttt tgaaggtcat    2340
attactgaga ttatctacaa aggggcccac aatcaccctaa agttgctcc tacccgcaga    2400 tcggcgattg ggtcctcaag tgtgctgagt gatataagtg aactaactgg gaatggagtt    2460
gagggtggtt ctgtttgggg gacaaatatg caacagaagg gtggaggtaa ttgggggcaa    2520
gaaagtaatt ttgaggtgac atcatcggcg atggttatgc agggtcagaa tggtcaatat    2580
gaatctagta tgctgttga tgggtcatcc acttttttcta atgatgaaga agatgaccgt    2640
gcaacacatg gcagtgtatc acttggttat gatggtgaag gagatgaatc tgagtctaaa    2700
agaaggttcg actgttttt tttttgtgct ttttgttaag tgattataac cgtcatcgat    2760
ttttgctgtt ttagtaacct atttctgcgt atgattatct aattatatca ggatgagatg    2820
actggataca gttttgctc aaagtatgta atcttaatta atatataatt aatttatcaa    2880
atgtatcatt acaaaatcta tactatttta aaatgatat attttttaat taaacgtttg    2940
aggaggttag tgtgttaaaa ttacagtttg ggcaactttt gacccatgtt tgttttagct    3000 tttttattc tacctatttg accgttggtg agggaaaaaa aaaacaccca acacctccct    3060
tgtaaatttt aattatttgt ttcaacttta agacacattc aaacactatt tcttgtaacg    3120 attttgtta aagcttatga tttgcttgtg attattatat ttcatacacg tcactttcaa    3180
gatgcatatc caaacactcc ctaatcctta actgtatgat gttttagaaa agttgaagca    3240
tatgcagcag atgtaagtgg cgcaaccaga gcaatcaggg aaccaagagt tgttgttcaa    3300
actaccagtg acgtggacat tttggatgat gggtatcgct ggcgcaagta tggacagaag    3360
gtcgtgaaag gaaaccctaa cccaaggtca tcattttgtg ctgttatgta tctgttatct    3420
aacttagctg tgaattggtt agacgtagca aaatgggcgg gtcaattgtg tttgggtcaa    3480
ataaggagtt cctaaacgcc aggtaaattg ggtcaggtcg gtcttctgga caaagcttct    3540
gccctataaa gcgaaatttt ctaataaaag gatgtaggat gttataagcc tccggagtat    3600
atgttggcaa cttaggcccg cctcccttca aattgtgtct gaattttttcc catttttttgg    3660 tttataaatt gtgatgtcaa ttgtttagat gtggcaaaat ttgtggggttt agatcgaaac    3720 gagtttcttt tggtaccagt cagggtcagc ccatatctgc tattttttcct ttttcttact    3780 ttttcgatat ggattaaata tgactacaaa gttaaacatt aaaatggtaa tttaatttat    3840
taataatatc atttatagtt tcatcaaaat gagcaacttt tggtaccaag ttcttgaaag    3900
tgcccgtttg acccattgac ttaattatag atatatattt ttttttgtttt ttttttttttt    3960 ttttgaaata aattgttttt tatggcacag gagttactac aagtgcacaa gcacaggctg    4020
cacagtgaga aaacatgtcg aaagggcatc acatgcccta agatcagtga taacaacata    4080
cgaagggaag cacaaccatg atgtcccagc tgcccgtaac agcagccata acaacaacac    4140
cattcagcct caagttcaaa tgcccgggct atctcgtggt caaaacacca tgcctcggct    4200
cgaaaggcct ccctatggtt tacccaatgg tcagcacctg ggttctgctc caacccatgg    4260
```

```
ctatggttac caaatgaacc aacaaggacc aggagggcta gcccatatgg ccatggccaa   4320
ccaagggaga atgcctgttc ttcctcttca tcactatttg aatcaaccac aacaaatcaa   4380
tgaaatggga ctgatggtgt caaaaggtga gccgaaggtg gagaccatgt ctgatcctgg   4440
cctgaaccta gccagtggtg cagcgattta ccatcagatg atgaaccggt taccgcttgg   4500
acatcagatg taaagtttga tagaagtatg cattcttttt ggcaaagagt agaatattta   4560
aacttgatat cacattatct tttttgttac aactttaggg gttttcttgt tttttaagta   4620
tttatttcaa gaatttgaag ctatattggt agaaggttat tatcatttat acaacagttt   4680
aattttaata gaaattttat gtcagattta acatgagtct gtctgatagt ggcactccat   4740
ttatccttca cagaaatgtg tgggccctcg atgagcaaaa ctgaattgca ccacttttaa   4800
attgcactac gtgaaaataa cgttaaaagc ggcggacggt taatcatgca tcatgtggtg   4860
gcgttagtag ccaaaagaca atgg                                          4884
```

<210> SEQ ID NO 40
<211> LENGTH: 786
<212> TYPE: DNA
<213> ORGANISM: Parthenium argentatum

<400> SEQUENCE: 40

```
atgtctgcac aatcttttca gagtaatgaa gcttttaccc aacctgagga acaatttcag     60
cctcaaaaga gtgaaccggc ccaaatttac tcagacttta ctgaaaggaa gaacttttcg    120
ctacaaatgg ctccatttga agctcgtaat ggcaattctg atctgactca acagcatcat    180
gataaacatc acgatgagat tgacgcagat cagagtataa atggagatat tactaatgct    240
agcagtgcat catctgatga tgggtataat tggagaaaat atggacagaa acaagtaaaa    300
ggaagtgagt atcctagaag ctattataaa tgcactcacc caaattgtac tgttaaaaag    360
aaagtcgagc gttcttttga aggtcatatt actgagatta tctacaaagg ggcccacaat    420
caccctaaag ttgctcctac ccgcagatcg gcgattgggt cctcaagtgt gctgagtgat    480
ataagtgaac taactgggaa tggagttgag ggtggttctg tttgggggac aaatatgcaa    540
cagaagggtg gaggtaattg gggcaagaa agtaattttg aggtgacatc atcggcgatg    600
gttatgcagg gtcagaatgg tcaatatgaa tctagtgatg ctgttgatgg gtcatccact    660
ttttctaatg atgaagaaga tgaccgtgca acacatggca gtgtatcact tggttatgat    720
ggtgaaggag atgaatctga gtctaaaaga aggttcgact gtttttcttt ttgtgctttt    780
tgttaa                                                               786
```

<210> SEQ ID NO 41
<211> LENGTH: 3124
<212> TYPE: DNA
<213> ORGANISM: Parthenium argentatum

<400> SEQUENCE: 41

```
cgaaaaccca tccgagggga ttccgcaccc tcgcgactga aaaccgcggt aatccggacc     60
cgtaaggcgc gtccgaaacg gtcctacata ttatatttct atgtttaaac gacatgttta    120
atactcggtt gtcgtgctta tctttatata cgttttgctc taaatttgtt cgaaaaattt    180
ggtttttgta tacaataact taacttttcc atgattttct aatacaccat cgcgacgtaa    240
ttttttatca tcacgtggag cgcgacgata acttactagt tataagttaa taaccaaaaa    300
aaaaaaatgg ttatgaataa caattattta tgaaaagaaa aaaataggca tcatatacca    360
ataagcataa atcaatacaa cgtttgtttt atcagggatg aatcaacttt ataattttat    420
```

```
atattgagtg attgaattga agactcataa gaggatcaaa tgcaatttat tgttagttag    480
ggaagcaagg tgttattgac ccctaaattc ccaaacggta acacacccca ccccaccccc    540
aacatctctc tctctctctc tctctctctc tctctctctc tctctctctc tccacttttt    600
atataccaat tatccaaaaa ggcaaaaacc ctcttcacac tatactcaaa ataacctct     660 ctttctctcc atctctctct atatatctcc atctatccct aaaataaaga atccatgcct    720
ttgatcagtc catggaaaac aactcagagt caaacaacaa ctcaaacaat tcaaacataa    780
tgacaagcac agcattttcc gatcatattc cggcaaccta tggtggtaac ttttttgata    840
tgttaactta tcaggacgac ggtagctcat gtctctttga tctgcttcaa caacctgctc    900
ctcctttgaa cttggtaccg gaaaataata ataataataa taataataat aataataata    960
ataataataa taataatctt ctaccaccag tggaaatggt gaatacaccg acacaaaact    1020
cttcttccgt atcatgttct tcaaatgatg ttgatcagga gaataaaagc agatctgttc    1080
atgaagaaga tgatgttcat gatggtgatg atgatcaaga aaagagtgct actaataaac    1140
agtaagaaca ctagttttgt ttagttttga acacacacta tcgggtgtgt ttttatgtac    1200
tttgctaact gtgtgttttt cacacactgt ttggtgtttc ttgtgtgtgt tttttacact    1260
taaatgagtt tttatgagtt tgtgtgtgct gtttatcgca tccattattg ctagatttat    1320
attaagaaaa tatcattcta taaaattagc acacacttat ggtggtgtgt gtgtgtgtgt    1380
atttggtgtt tttgtttgtg tttttaacac acatgagttt ttatgagttt gtatgtgttc    1440
ttcatcaaat caatcatgct taatggatat caagaaaata ttttcttca aaactagcac     1500 acacttatgg tgtgttatta tttttttatt tttattttt tgtgtgtgta tatggtgttt     1560
cttgtgtgag ttttcacac acacatgagc ttttatgtgt ttgtatgtgt tcttctttaa     1620
atctatcttg ctaaatgaat attaagaaaa tatctttcta caaaactagc acacactttg    1680
gtgtttgtgt gtttgtgtat tgatgattaa tctttcattt ttctattatt gttggttgtt    1740
cacatacaca tgaacttta tgagttcttc attccttctt cattgccagt aaatgaaatc     1800
aagaatttaa gaaaagttat attccactaa ataagtgtaa ttcctgtgta tttttcaggt    1860
attaaatcag tggtttctgg ccaaaaaaaa aaaaaaaaa aaagaaaaat cattaatttc     1920
ttgtttcaca cttacacgtt ttcttcaagg tctttaattt gaccaagaat agttaggtcc    1980
ttttcacaca catatacaca cccaaaacta gatttgatga ccaggtcttt agtggtgcac    2040
cagttttcta gatttaataa gtctttattc ttctttctcc ttatcgtttt atttcttaca    2100
aaatatttta tcttattctt ctttatata tatatatata tatatattat gtcgtttatt     2160
cttgaactaa aatgtggctg tttcactgtg ttgcgtaggt taaaacccaa aaagaagaat    2220
ccaaagaagc aaaggggacc aagatttgca ttcatgacta agactgatat tgatcacttg    2280
gatgatggtt atagatggag aaagtacggt cagaaagctg tgaaaaacag ccctttttcct   2340 aggtgtatac tctctctttc tctctagatt ccatctcttt ctctctctac acccttgttt    2400
gagttgccct aacatatgac tatatctata tcctttggag tttgatccat tcataccatg    2460
taattaaaga tagttcatac ttcttttatg gttattttca attaaacgag tcgcgttcat    2520
atagatattg atatggtatc gacataaaca cacatcgtgt tgtattagat tgacatggta    2580
taaatttgaa aacacatata tacacaatca tccatcatat atgttaaaga ttgaaccaat    2640
ttttgttgta caaaatagga gttaccatag gtgcacaagt gtggcttgtg gagtgaagaa    2700
gcgagttgaa agatcgtctg atgatccatc gatcgtgatc acaacttacg aaggtaccca    2760
```

| | |
|---|---:|
| cactcatctg catccgatta tgcctcgagg aaacattgag atcttgtcgg agcccaccgg | 2820 |
| tcatggtggt ttcagtggtg gtggtagtaa tagtggtgtt acttcttttc tttttacaca | 2880 |
| gcttcacaac caacaccaac aaccacaact actaccctat gtccatcacc aaaccacacc | 2940 |
| atcatcttct ctaggctttta acaccactat tgatagtgca catcaatcat catactccca | 3000 |
| tttacttcac gaaagacgat ttttcccttc atcttcttct acattgctta gagaccatgg | 3060 |
| actactagag gatgtcatcc aattccagtt tcagaaagat aagcccaaag aagaacagaa | 3120 |
| ctaa | 3124 |

<210> SEQ ID NO 42
<211> LENGTH: 504
<212> TYPE: DNA
<213> ORGANISM: Parthenium argentatum

<400> SEQUENCE: 42

| | |
|---|---:|
| atgttaaaga ttgaaccaat ttttgttgta caaaatagga gttaccatag gtgcacaagt | 60 |
| gtggcttgtg gagtgaagaa gcgagttgaa agatcgtctg atgatccatc gatcgtgatc | 120 |
| acaacttacg aaggtaccca cactcatctg catccgatta tgcctcgagg aaacattgag | 180 |
| atcttgtcgg agcccaccgg tcatggtggt ttcagtggtg gtggtagtaa tagtggtgtt | 240 |
| acttcttttc tttttacaca gcttcacaac caacaccaac aaccacaact actaccctat | 300 |
| gtccatcacc aaaccacacc atcatcttct ctaggctttta acaccactat tgatagtgca | 360 |
| catcaatcat catactccca tttacttcac gaaagacgat ttttcccttc atcttcttct | 420 |
| acattgctta gagaccatgg actactagag gatgtcatcc aattccagtt tcagaaagat | 480 |
| aagcccaaag aagaacagaa ctaa | 504 |

<210> SEQ ID NO 43
<211> LENGTH: 5769
<212> TYPE: DNA
<213> ORGANISM: Parthenium argentatum

<400> SEQUENCE: 43

| | |
|---|---:|
| gtaaaaagaa attttgtatt tttatgtttt tttttcgagt ttttgcgttt tttttctttt | 60 |
| tgttctcacg gttctcacga tatttagtgt tctcaaagta accctcccctt ttatatatat | 120 |
| atatatatat atatatatag acacacacac tctgaagata ggtgattcta gtcatataaa | 180 |
| tgttatcctt tttattgtag gtatgcaaat tgtaaaaaag aatatccatc caatcattta | 240 |
| ttcttaggtt tatatccaat tttgttcaaa accccacctc ccaccacaca tatatcatca | 300 |
| tcattatttc ccttggtgcc aaacctaaga cttctctatc tttctctctt tatgtgtgct | 360 |
| ttttaggtgt tgaatgattg tgggtcattc ttacttcttt gttttagtaa tacaactttg | 420 |
| agcgaaaatg gggagaaagt gctcacactg tggaaacata ggccacaatt caagaacttg | 480 |
| cactagttac aatagaagca atgtcaatag cacaattttg gtaggtggtg ctggaggagg | 540 |
| attaaggcta tttggagttc aacttgactc accacactct atggtcatga agaaatgtct | 600 |
| tagcatggat tgtttgccat ctagctcacc attaccggct tcggtttcat cttcttcttc | 660 |
| ttctttatct tcatcgcggg tctccatcaa tgacctaacc gaaagaata tgtcggttgg | 720 |
| ttatctctca gacggtctca ttgcccgcgc tcaagaaaga aaaaaaggta tgcaaactta | 780 |
| ttatatatct actattagtt acttaaatca tgaatgacta ctaaattggc tatgaaatat | 840 |
| atctttatgt tatgttatgc tatattatgt tatgtcacgt acattgtgat tgacatgcat | 900 |
| gtgtttcatt tcaagattca catgtagaga taaaagaatg tagatttcaa tggtaacata | 960 |

```
taggagggt tgttttatag gtctcccttg gtccgaagac gaacatcgta gatttctagc    1020
cggacttgag aagcttggaa aaggtgattg gagaggaatt tcaagaaact ttgtgaccac    1080
aaggacacct acacaagttg caagtcatgc tcaaaagtac ttcctccgcc aagcgagtct    1140
tgtcaagaag aaacgtcgtt caagcctctt tgacttggta cgtattttg cattgcaatt     1200 gtactttgca attaaaggct tgtacatacc accctcaaac attagtctat tgaaggcctt    1260
tcaccataca atgtttccat ttggccatga ggcttttaaa gcaaggtaca acccataatg    1320
caataggtaa caaccctata atgcaaaaaa gccgtaaatc caaattacgg aaattactaa    1380
accatgtgcg tcttttata tataaagaaa tgtaaagtgt gcctaaatta tagttgcatc     1440
ttggtggtca caggtgaggg acaagaatgg gcaacagaat caaataaaga attgcaatat    1500
gagtcgaaca agctcattcg aggatgaata tgaagaggat cataacaata atctttcttt    1560
gattgatttc ggttctctaa aacaagagaa gggccacttc aatccgatga tcaaatccta    1620
tgaaacatca ttatcatcaa cgtgttatgc gcctccaagt ggtacgcttg atttagaact    1680 taccccttgct gctcccaacc cgatgaatca gaacaaatcg tctaccacct ccctccaact    1740
cggtccgatt attagtgtta tttagggata cgtttgatct gacacttttc atatgttaat    1800
tcatgttgaa caatctaatt atgatcaaat gttgtagata ttttcttgaa ttttgagacc    1860
tttgacacgg gtcttgtact ccggttagat aatattttg taactacaaa tttatatgta     1920
tgtactctat taaattagga taaaatcaag agaataatct ttttttaag ctacaaattt     1980 cacatatcta ttttattttc atatatcatc ataacactca gttttcaaga aaatatatt     2040 agctagatgt gccaaaataa aataaatata tgaatagtag acatacgaat gaaaaagtga    2100
aaatttactt tggtgataag aaaaatatac ttctttcttt tataatgata tccatatcat    2160
ggacccatta ttttatttta ttgtaaaaaa aaggaccca atatcaatgt caatacctaa     2220
ttactctcaa gccatgaaac acgaagttta ctttaaaatt ctcggtgttt aattatttat    2280
atatgtttta gaaactaatg ataaaatagt aataaaacta ctcccaaatt ctaagaagct    2340
taataagaat ttggtgaccg gaaattggtt atctaagggt tatgttttta accaaatgtt    2400
atgtgtgtat tgggggtcct ctataaaatta gtaacatatt tatctaaaaa gactatgcaa    2460
aaagatgcaa cctagaacaa gtgtgttatg catataatct tccaagtcga acgctaatta    2520
gcctcgtctt tggtcctgat taacccggaa acagcactaa agtggaattt tatgcaagaa    2580
ttgaaactaa aaggttgttg gaaaaacaag tgtatgaaaa gatgatacaa tgtaacaaag    2640
gtacctaaac cttggattta gacaagaatt gggtgcagaa atggaccact ttaacaaaga    2700
gttgtaccct ttgtatcaga atttgttcag tatcctgcaa caggaagctg ttaagattaa    2760
gacctaagaa ttgatgtgtg gaccttctta gaggatgaag acaagatgga aagatacaat    2820
caatctgaga aagatttta gatgggtcta gctttataat gcaagcatct gtctcattat    2880
agttcaatcc aacatgatga acaagaatca aagaaagata ttttaggggt ttgaaaatga    2940
tagatacgtt taacttggac aaatttatta attttgatta tctaaaatct aatacccgt    3000 taatcaataa ataaagatct ctttatcaat ctaccatata gtctttgata gatagccagt    3060
gaaagtcagg tatgctagca gttttttgtg cttatttggt cacctttgga aagttggttt    3120 cttgttttata accataggac caccaatacc ccgttaatca ataaataaag taaagtaaaa    3180
agcagcttgc gctagacagc tgatctttga gagagttaag acaacgccgg tggaaactga    3240
attcggatat gagacggcct ccgctgaata cacttaaacg tttactatta agacaccact    3300
```

-continued

```
taataatttt catatttcca ttcaccccta aaattaaatt attcctcaaa tcaagtcttt    3360
ttgttcaata aagccaaact tccataagaa ttaacaatat cgtgtcttca aagttcaaac    3420
cacaaacact aaccccattt gatattttcc catatgtgaa gtaccaactt ggctcatcag    3480
aagttaacca ctctcattaa gtctcttgtt ttattatcat attcttgaat gtgcgctttt    3540
atgaaacagt gacatataaa aaacaaaaa cctctgtctg ctttactaac cgattctagg    3600
atgtctttta ttattttat ttttttattt tcatttgtgt ttgttttcat cttatgtatc    3660
atcatttgta ttcacatgtt tttgtgtgga ggatacacct ttgtcctaac catcaaagta    3720
acggtgtaaa tgaatccaac tcctaagagt tcctcaagat taacatgttt taaggttgaa    3780
tcgattaaac aacttcaagt cgagataatc ataagtaaag ggtactaggg acatcataag    3840
taaagggtac tagggacact acccttaccc taatggctcc gattaataag ggataaccac    3900 ctcatttta atcaaatcca acgtagcact agccaaagca tcctattttt atttattttt    3960 ttcaattta aagattaaaa ctaatatata cttaaaaaca caaatattaa taaatttctt    4020
aactaaaaca agcataacaa agtataaaac attaaaacat aaaaacatct aaaaataaaa    4080
attacaaaaa tgtttaatta atcgccgatg tgcattttg tatcgttgtg aaactctttt    4140
atcatcatca cgtctagacc tcttgcaacc attccgtttt taaagataac tcttcgacat    4200
aagaaacttg aacgaaaagt agcttcatcg tattttggcg ggcgaaataa tcttccatta    4260
gatcctctag agcttttgca tgatcacgtg gcacatttt ttatgttgcc gttgtctact    4320
actttggctt gagcggcaac atccgtgaga atatggaggc tactagatac gcctccgttc    4380
aagtcaaacg catccgatga atcaaatgga agtcataact taagattaat tttgtgatgc    4440
aaagtttgaa tgcaaaatta tttgtagata tgagagtatg aaatcggtat tttgggtgta    4500
caaaagtaaa tggagatgag tttatttag gtgtggtaaa gttggtattt atcaactcat    4560
gagtgaatct tggactttag acagagtttg aaacaaattg cgctcgaatt tcaaaagcca    4620 aacccccta agttaaagga gcggacgcaa cctacacatg ctgacatgct cacttgaaca    4680
aagattcata aattaagttt tattacttat gttgttcttt cctttttata cattacatgt    4740
gttggttcac cagatgtttt acaaggttgt ttttgatgtt ttacccaaca ttgttgtctc    4800
ccacctcttt catttcacct cttcttttt acgtttatct tatttcacat tttcgtttta    4860
taattccgac atcttcatac taattatttt aaaataaatt attcaattca tgtaatacat    4920
cattatacat gggcatctaa cctcgtgtgt gtgcgcacgc acccgctcat gtgtgtatat    4980
atatttagag agagagagag agagagagag agagagagag agagagagag agaagggcgt    5040
tggacggtgg tgccaggtgg cccggggtcc tcctcagtcc tcaccatgag attgtgcggg    5100
atgggaccag ggaggggaca caatgttccc acaagccctg caaggacgtg gaaccttctt    5160
gcgcctttcc ttgaaaccat aacacatggc ctaagttata cctatatctt aaattaattt    5220
aagagactcg ttaatcaatc acaattctca aactatcatg ataattaatt tttgtacgac    5280
atgaaggcgt ttgatatttt tatgaagatt gaattatctg ctaagagagc taagagatac    5340
tgataacact attgtataag tttattccat ataatctata ctatattata atagatttga    5400
ggaaaatgca attgtctttt tttttacatt aattttaag agtttaagga gttaattttt    5460
ttttttttat atatataaaa tatcatcata aaaatgctcg acccacatta ccattactta    5520
acgaggtaaa atgctatcat caacatatct caagattatt tgcaaacaca atgttgtaga    5580
cttaataaac acacgatcgt acatcatatt cacatttctt ttatccgaga tcatcacaga    5640
gtataattgt ttcattttca tttcgtattg tagaaactta tacatacttt attgagagat    5700
```

| | |
|---|---|
| cataatcacc atatgcttat tccttcatag aaatttacat cccaaaatg tatgctttta | 5760 |
| agcactaaa | 5769 |

<210> SEQ ID NO 44
<211> LENGTH: 369
<212> TYPE: DNA
<213> ORGANISM: Parthenium argentatum

<400> SEQUENCE: 44

| | |
|---|---|
| atggtaacat ataggagggg ttgttttata ggtctcccct tggtccgaaga cgaacatcgt | 60 |
| agatttctag ccggacttga aagcttgga aaggtgatt ggagaggaat ttcaagaaac | 120 |
| tttgtgacca caaggacacc tacacaagtt gcaagtcatg ctcaaaagta cttcctccgc | 180 |
| caagcgagtc ttgtcaagaa gaacgtcgt tcaagcctct ttgacttggt acgtattttt | 240 |
| gcattgcaat tgtactttgc aattaaaggc ttgtacatac cacctcaaa cattagtcta | 300 |
| ttgaaggcct ttcaccatac aatgtttcca tttggccatg aggcttttaa agcaaggtac | 360 |
| aacccataa | 369 |

<210> SEQ ID NO 45
<211> LENGTH: 1257
<212> TYPE: DNA
<213> ORGANISM: Artificial Sequence
<220> FEATURE:
<223> OTHER INFORMATION: anti-sense RNA
<220> FEATURE:
<221> NAME/KEY: misc_feature
<222> LOCATION: (1161)..(1161)
<223> OTHER INFORMATION: n is a, c, g, or t

<400> SEQUENCE: 45

| | |
|---|---|
| ccatggccgc gggattcgcc ggaaaagttc aatcacaaac aacctcgtta taagcacggc | 60 |
| aaagtctttt ccggcacatt gtttatttc aactgatcgg actctctgtc tccggcccat | 120 |
| tagaccacca tacgtacttc aacaatgcct cgccatcccc aacgagccga tcagggacat | 180 |
| attcctcagg tcggtcaaat acttttgggt ccttggttgc aaacggttgg tacccgaata | 240 |
| acatttctcc tttttgact tcgaaagtgg cgtcgtgtga ctctatggta aagttgcttt | 300 |
| tggcttttcc atattgcgga ggcactggtg gatccccgg gttaagagga gtccaccatg | 360 |
| agcccagaac gacgcccggc cgacatccgc cgtgccaccg aggcggacat gccggcggtc | 420 |
| tgcaccatcg tcaaccacta catcgagaca agcacggtca acttccgtac ggagccgcaa | 480 |
| gaaccgcaag agtggacgga cgacctcgtc cgtctgcggg agcgctatcc ctggctcgtc | 540 |
| gccgaggtgg acggcgaggt cgccggcatc gcctacgcgg gccctggaa ggcacgcaac | 600 |
| gcctacgact ggacggccga gtcgaccgtg tacgtctccc ccgccacca gcggacggga | 660 |
| ctgggctcca cgctctacac ccacctgctg aagtccctcg aggcacaagg cttcaagagc | 720 |
| gtggtcgctg tcatcgggct gcccaacgac ccgagcgtgc gcatgcacga ggcgctcgga | 780 |
| tatgccccc gcggcatgct gcgggcggcc ggcttcaagc acgggaactg gcatgacgtg | 840 |
| ggtttctggc agctggactt cagcctgccg gtaccgcccc gtccggtcct gcccgtcacc | 900 |
| gagagatctc tagtgattgg atccaccagt gcctccgcaa tatggaaaag ccaaaagcaa | 960 |
| ctttaccata gagtcacacg acgccacttt cgaagtcaaa aaggagaaa tgttattcgg | 1020 |
| gtaccaaccg tttgcaacca aggacccaaa agtatttgac cgacctgagg aatatgtccc | 1080 |
| tgatcggctc gttggggatg acgaggcatt gttgaagtac gtatggtgat ctaatgggcc | 1140 |

```
ggagacacag agtccgatca nttgaaaata aacaatgtgc cggaaaagac tttgccgtgc   1200
ttataacgag gttgtttgtg attgaacttt tccggcgccg cggggagct cggatcc        1257
```